(12) United States Patent
Baudot et al.

(10) Patent No.: US 6,207,883 B1
(45) Date of Patent: Mar. 27, 2001

(54) DNA SEQUENCES CODING FOR A PROTEIN CONFERRING MALE STERILITY

(75) Inventors: Gaelle Baudot, Clermont-Ferrand; Denise Garcia, Beaumont, both of (FR); Rachel Hodge, Leicester (GB); Pascual Perez, Chanonat (FR)

(73) Assignee: Gene Shears Pty. Ltd., Canberra Act (AU)

( * ) Notice: Subject to any disclaimer, the term of this patent is extended or adjusted under 35 U.S.C. 154(b) by 0 days.

(21) Appl. No.: 09/102,528

(22) Filed: Jun. 22, 1998

Related U.S. Application Data

(63) Continuation of application No. PCT/GB96/03191, filed on Dec. 20, 1996.

(30) Foreign Application Priority Data

Dec. 21, 1995 (GB) .................................................. 9526218

(51) Int. Cl.[7] .............................. C12N 15/29; C12N 5/04; C12N 15/82; A01H 1/02; A01H 5/00
(52) U.S. Cl. ........................... 800/303; 800/274; 800/278; 800/287; 536/23.6; 536/24.1; 435/69.1; 435/320.1; 435/419; 435/468
(58) Field of Search ................... 536/23.6, 24.1; 435/69.1, 320.1, 419, 468; 800/274, 278, 287, 303

(56) References Cited

FOREIGN PATENT DOCUMENTS

| WO9213957A | 8/1992 | (WO) . |
|---|---|---|
| WO9425593A | 11/1994 | (WO) . |

OTHER PUBLICATIONS

Hamilton et al. AccessiOn No. U41000, Locus ZMU41000, Nov. 1995.*
San Miguel et al. Science 274:765–768, Nov. 1996.*
Ulmasov et al. Science 276:1865–1868, Jun. 1997.*
Turgut et al. Plant Mol. Biol. 24(1): 97–104, 1994.*
Williams, Mark E. "Genetic engineering for pollination control", Tibtech, vol. 13, Sep. 1995, pp. 344–349.
Sasaki T., et al., "Rice cDNA from shoot" Heidelberg, BRD, AC D40316, Nov. 13, 1994.
Parmentier, Y. et al., "The *Arabidopsis thaliana* transcribed genome: the GDR cDNA program" Heidelberg, BRD AC Z34707, Jun. 25, 1994.

* cited by examiner

*Primary Examiner*—David T. Fox
(74) *Attorney, Agent, or Firm*—John P. White; Cooper & Dunham LLP

(57) ABSTRACT

This invention relates to a gene associated with male fertility, labeled Ms41-A, and a recessive mutant form thereof, labelled ms41-A, which confers male sterility. The Ms41-A gene is isolated from Arabidopsis, while the related gene Zm41-A is isolated from maize. Male-sterile plants are useful for the production of hybrid plants by sexual hybridization.

24 Claims, 35 Drawing Sheets

THE TRANSPOSED 35S Ac ELEMENT IS LINKED TO THE MALE STERILE MUTATION 41-A

41-A MALE STERILE MUTANT LOCUS

FIGURE 3 (I)

```
                                                          EcoRI
TCCTAACTTTCTTTGCGGCATTTCTTATAATACTTCGTCAGTTTTCAGAATTCTTAAATC
      -1780              -1760               -1741

TTTTTGCTGTGTTCTTATAAAGAAACATCATCTATTAAAGTTGTCTTCGTTTGGATTTGG
      -1720              -1700               -1681

TTTTGATGACTTTGGGAAATATTTATGTTTAAGAAGGTTTCATTGGTCATTGACTTTTAT
      -1660              -1640               -1621

ATATTATATCGTAACCATGATGTGATAGTGGGCCTTAGATCAACAAACATGCGAAAAACA
      -1600              -1580               -1561

GAAGCAGAGGCCCGTTTCAACGGAGCATAATAAATTGCATTCTCTGTCTTTTGTTTTTAG
      -1540              -1520               -1501

GTTTTTTTTTTAACTGATAGATGTGCCGTCGAAAATAATATTGATATTTAAAAATTCACA
      -1480              -1460               -1441

ACAAACATTCTTAACTGACCCACCCATCTATCTGCTATTCCCACGCGCCAAGGAAAATAA
      -1420              -1400               -1381

TAATAATAGCGAAATTGATTTTACATTTATTTATTGATAGATAATTTGTGTATTGTTAAG
      -1360              -1340               -1321

ATTAACAGATTTTAAGGGATTAAAGTGGAAAAGGTAAACCGAAGACAACTTGCCATTTAC
      -1300              -1280               -1261

TGATTTACAACAATCCAAATTTAAAAACAAATGGTCCCAGTTTTTAGGGTTGTCACTTAA
      -1240              -1220               -1201

ATTTATCGAAATATTTACACTTTAATTGGGTAAAACATAATGGACAGAAAAACAAATATT
      -1180              -1160               -1141
                                                    HindIII
GTGACAAACAAAAAAACATGTTTTCACCAAGAAAAACAAAAACAAAAAAGATGTAAAGCT
      -1120              -1100               -1081

TTTCTTACATCTGTACAAAATAAAAGCAGACGAAATTGTACTTTATTTTCCTTATTAAAT
      -1060              -1040               -1021

TGTCGGTATGTTTTATATGTTGTGAAAAGTAGAATGGATAACCAAATAAAAATTACTGCA
      -1000              -980                -961
                                                    HindIII
TCTTAATAAAGTTGGTTCAACCGGTTTAAAATGTATTTTTTTAGTGTTAACAACTTAAAG
       -940               -920                -901

CTTTTTTCGATTATCGAATTGCAACAAACAAATATATTAACAGAAAAAAGGAATCATGTA
       -880               -860                -841

TCTATTTCAATATCCTGTTTTTTTTCTTCCATTTGGATATTTAGATCTTTTTCTGAATTT
       -820               -800                -781

ATCTTGTTCTTAAATTAAAACAGAAAAAAAGATTAAAAGTAAGACAGCTTGCTAATGGCA
       -760               -740                -721

ACCGCAACAAACAAGATAATTTTGAAACGGATCCACTTGGATTTTCTTTGATTTTGTAGA
       -700               -680                -661
```

FIGURE 3 (II)

```
AAAATTGACAAATTGCTTTTGTATAAAAACAAAAAATGTACCGTAAAAACACACACATAA
          -640                -620              -601

AAAATAAAAAGTGATAATGACAAACAAATAAAGAGGTATTTTTCTTTTATCTACTAATGT
          -580                -560              -541

GATTATAAAAAAATCGACATTGAAAATTTCAACACATCTTTTTCGCCAAAACCTGAAAAT
          -520                -500              -481

GGTCTTATTATAACATAAATTAGTTTTTTTGTCTTTCTATTATATATTCAATAACTCATC
          -460                -440              -421

CCAACTTGAACAAACCTATAAGTTCCGTAGTGTTCTTTTCTGTTGTGACAAAAAATACTA
          -400                -380              -361

GCTAACGAGGGATAAGCACAAAAACATGATTAATGTTTCTCTAATCATTCTAAAAATCTA
          -340                -320              -301

CAGGAATATTCCCTTTTCAGTTTTTTCTTTCTTAAATGCATTTCTTAGTTCTTCATAATT
          -280                -260              -241

CAGTGAGTTTTAATAACAATAATAAAAAAAAGAGCATCATTAATTGAACCTAAAAATAAT
          -220                -200              -181

GGGAAGAAAAACCAAAAAGATAGAGAGTAAGATGCACGCGCTAAAGATCGAACGGTTAAT
          -160                -140              -121

AGAATCAGGTTAGTGAAGAGAGATATTAAAAGTTTGTTGTCGTGTGGCAAAAACTATAAT
          -100                -80               -61

TTCCTTCACACAAACAAAAAAAATAAAATCAAACACAAAATCCCGTAGCATCGTAACAGT
          -40                 -20               -1

AATTCGCTATTATCTCCTCACCCTCCGCTTTCGCTTCCCTTCTCTGCCCGTTTCAATTCC
1                   20                  40                  60

TTCTAAGACATCACGGTCTCTCTCTATAAAAACAGTACCTACCTCTTCTTCTTCTTCTTC
          80                 100                120

M  S  P  P  S  A  T  A
ATTCGCTGACTTCGTTTACACTGAAAACAAATACCTATGTCACCGCCGTCGGCAACCGCC
          140                160                180

G  D  I  N  H  R  E  V  D  P  T  I  W  R  A  C  A  G  A  S
GGTGACATCAACCACCGTGAAGTAGACCCGACGATCTGGCGCGCTTGTGCTGGAGCCTCC
          200                220                240

V  Q  I  P  V  L  H  S  R  V  Y  Y  F  P  Q  G  H  V  E  H
GTCCAGATCCCTGTCCTTCACTCTAGGGTTTACTACTTTCCACAAGGTCACGTTGAGCAC
          260                280                300

3' 35S-Ac 5'
               ||
 C  S  P  L  L  S  T  L  P  S  S  T  S  P  V  P  C  I  I  T
TGTTGCCCTCTCCTCTCTACTCTTCCTTCCTCCACCTCGCCGGTTCCATGTATCATCACT
          320                340                360
```

FIGURE 3(III)

```
     S  I  Q  L  L  A  D  P  V  T  D  E  V  F  A  H  L  I  L  Q
    TCAATCCAGTTGCTCGCCGATCCGGTTACCGACGAGGTCTTTGCTCACCTTATTCTTCAA
              380                 400                 420

P  I  T  Q  Q  Q  F  T  P  T  N  Y  S  R  F  G  R  F  D  G
    CCGATCACGCAGCAGCAGTTTACTCCGACTAATTATTCACGATTCGGCAGATTCGATGGC
              440                 460                 480

D  V  D  D  N  N  K  V  T  T  F  A  K  I  L  T  P  S  D  A
    GATGTTGATGATAACAACAAGGTGACTACCTTCGCCAAAATTCTCACGCCTTCTGATGCT
              500                 520                 540

N  N  G  G  F  S  V  P  R  F  C  A  D  S  V  F  P  L  L
    AACAATGGAGGTGGCTTCTCCGTTCCTCGTTTCTGTGCTGATTCCGTCTTCCCTCTGCTT
              560                 580                 600

N  F  Q  I  D  P  P  V  Q  K  L  Y  V  T  D  I  H  G  A  V
    AATTTTCAAATCGATCCACCGGTTCAGAAGCTCTACGTCACTGATATCCATGGAGCTGTT
              620                 640                 660

W  D  F  R  H  I  Y  R  G  T  P  R  R  H  L  L  T  T  G  W
    TGGGATTTCAGGCATATCTATCGCGGTACACCGAGGCGTCACTTGCTAACAACGGGATGG
              680                 700                 720

S  K  F  V  N  S  K  K  L  I  A  G  D  S  V  V  F  M  R  K
    AGTAAGTTTGTCAATAGCAAGAAGCTCATCGCTGGAGATTCGGTTGTGTTTATGAGAAAA
              740                 760                 780

S  A  D  E  M  Y  I  G  V  R  R  T  P  I  S  S  S  D  G  G
    TCTGCAGATGAGATGTACATCGGTGTTAGGCGAACTCCGATCTCAAGCAGCGACGGAGGA
              800                 820                 840

S  S  Y  Y  G  G  D  E  Y  N  G  Y  Y  S  Q  S  S  V  A  K
    AGTAGCTATTACGGAGGAGATGAGTATAACGGTTACTACAGTCAGAGTAGCGTTGCCAAG
              860                 880                 900

E  D  D  G  S  P  K  K  T  F  R  R  S  G  N  G  K  L  T  A
    GAAGATGATGGGAGTCCGAAGAAGACGTTTAGGAGATCTGGGAATGGTAAGTTGACTGCT
              920                 940                 960

E  A  V  R  S  I  N  R  A  S  Q  G  L  P  F  E  V  V  F  Y
    GAGGCTGTACGATCGATCAATAGAGCGTCTCAGGGATTACCGTTTGAGGTGGTGTTTTAT
              980                 1000                1020

P  A  A  G  W  S  E  F  V  V  R  A  E  D  V  E  S  S  M  S
    CCGGCTGCTGGATGGTCTGAGTTTGTTGTGAGAGCTGAAGATGTTGAGTCTTCAATGTCT
              1040                1060                1080

M  Y  W  T  P  G  T  R  V  K  M  A  M  E  T  E  D  S  S  R
    ATGTATTGGACTCCTGGGACTCGAGTCAAGATGGCTATGGAGACTGAAGATTCTTCTCGG
              1100                1120                1140

I  T  W  F  Q  G  I  V  S  S  T  Y  Q  E  T  G  P  W  R  G
    ATCACATGGTTTCAAGGCATCGTTTCCTCTACTTATCAGGAGACCGGTCCATGGCGTGGA
              1160                1180                1200
```

FIGURE 3 (IV)

```
   S   P   W   K   Q   L    <---- intron 1
TCTCCATGGAAGCAGCTTCAGGTATATGATGTTTTTGAAATGGTCTTTGCTCTTCTTATC
           1220              1240              1260

TCTGTGATGTTGAGTTAATGGAACAATTCAGAATCGATCTTGTATCTGTTGTGTGCAAGC
           1280              1300              1320

CTTTAAGATGATGTTTAAGTCTCATCCTGGTTATTCAAATGTCAATTGGGTTTTGAATGT
           1340              1360              1380

TGTTTTGATTGCTGTGTTGTTTGTTTTGAAGCTAAATATTGGAAACAGGATAAGTTAAgT
           1400              1420              1440

CATACGAAAATGAATGTTCTGTCTCAGATTCATCTTCTATAAGATGGAATTGAAACTGGA
           1460              1480              1500

AGATTTGGCTTAGTATTGTgTGTgTTGAGCGTCCGTGATGTAGAGTTGTTTTCATTATCC
           1520              1540              1560

TTCTTTGGCCACGCATTGTACATTGTGTTTGTTAAACTAGAGTTCCTCTGATTAGTCTTA
           1580              1600              1620

TGAGATACTCCTTTTTTGCCAATATATTCTACTTCCTCTGATTAGTTCCTTTGTTTTTAA
           1640              1660              1680

------>Q   I   T   W   D   E   P   E   I   L   Q   N   V   K   R   V   N   P
CTTGCGTAGATCACATGGGATGAACCTGAGATTCTGCAAAACGTGAAGAGGGTGAATCCA
           1700              1720              1740

W   Q   V   E   I   A   A   H   A   T   Q   L   H   T   P   F   P   P   A   K
TGGCAAGTGGAAATTGCTGCACATGCAACTCAACTGCATACCCCTTTCCCTCCAGCAAAG
           1760              1780              1800

R   L   K   Y   P   Q   P   G   G   G   F   L   S   G   D   D   G   E   I   L
AGGTTGAAGTATCCACAACCCGGAGGAGGGTTCTTGAGTGGAGATGATGGAGAAATCCTT
           1820              1840              1860

Y   P   Q   S   G   L   S   S   A   A   A   P   D   P   S   P   S   M   F   S
TATCCTCAAAGTGGACTGTCTAGTGCAGCAGCACCTGATCCAAGTCCTTCTATGTTCTCG
           1880              1900              1920

Y   S   T   F   P   A   G   M   Q   G   A   R   Q   Y   D   F   G   S   F   N
TATTCTACATTTCCTGCTGGCATGCAGGGAGCCAGGCAATATGATTTTGGGTCTTTCAAT
           1940              1960              1980

P   T   G   F   I   G   G   N   P   P   Q   L   F   T   N   N   F   L   S   P
CCAACCGGATTCATTGGAGGAAATCCTCCCCAGCTATTCACCAATAACTTCTTAAGTCCG
           2000              2020              2040

L   P   D   L   G   K   V   S   T   E   M   M   N   F   G   S   P   P   S   D
CTTCCTGATTTGGGAAAAGTGTCGACTGAGATGATGAACTTTGGCAGTCCGCCATCAGAT
           2060 SalI         2080              2100

N   L   S   P   N   S   T   T   N   L   S   S   G   N   D   L   V   G   N
AACTTATCGCCTAATAGCAACACCACTAATCTGTCCTCTGGAAATGACCTGGTTGGAAAC
           2120              2140              2160
```

FIGURE 3 (V)

```
      R  G  P  L  S  K  K  V  N  S  I  Q  L  F  G  K  I  I  T  V
    CGAGGCCCCCTTTCAAAGAAAGTTAACTCGATTCAGTTGTTTGGCAAGATCATTACCGTG
              2180                2200                2220

E  E  H  S  E  S  G  P  A  E  S  G  L  C  E  E  D  G  S  K
    GAGGAGCATTCTGAGAGCGGTCCTGCAGAGTCTGGCTTGTGTGAAGAGGATGGCAGCAAA
              2240                2260                2280

E  S  S  D  N  E  T  Q  L  S  L  S  H  A  P  P  S  V  P  K
    GAGTCCAGCGACAATGAGACACAGTTGTCCTTATCACATGCTCCTCCAAGCGTGCCTAAA
              2300                2320                2340

H  S  N  S  N  A  G  S  S  S  Q<------ intron 2
    CATTCCAACAGCAACGCAGGTTCTAGCTCCCAAGGTATATTCCGATCTCTCTCAAGTACA
              2360                2380                2400
                                  HindIII
    ATAATCAATTGAATCAGTTGCTATAAGCTTTTATTACTGTTTTGCACAAGGCAATTTCTC
              2420                2440                2460

TTCCTTTCCCATGAACTATATTATGTAGAGTAGGAAACACAATCATGATTTCTGATATGA
              2480                2500                2520

CTTGACTGATGATGATACTTGTgAAAACTATCTATATATCTCTTCAGTAATCAGTCGCCT
              2540                2560                2580

TGAGGTAATTGGAATTTGGAACTTGAACATTACTTGGATTTTAACTTTTCAATAGCATAA
              2600                2620                2640

GCNTTCCTGTTTCATCATATATGTTTCACTATACTTGTATGCTTTTATTACTGCTGATAT
              2660                2680                2700

TTACTATTCCTGCTATTTTTTTTGGGTCTCGTTAACGGTAATAAGGACACAGAATTGGCT
              2720                2740                2760

CTTTTATCCATCAGAACTAGACATTACTGTACAAGTAGATGAAGAATTATGTGGTTCCAT
              2780                2800                2820
                                  HindIII
    TACAAATTTAATTTGCAGAAAGCTTGAAGCTGCTGCTTATAGACGATTATAATGTTGGAA
              2840                2860                2880

HindIII                              ------->  G  *
    GATCCTGAAGCTTGGAATGATTTGTACTTTTCTTTTGTTTGTGTGTGTTTTGACAGGTTA
              2900                2920                2940

AAAAGTGAAAGAAGTGGTGGATCTTTGCTGGAATCTCCAAGTCCTAAGTAGTAGTAGTAG
              2960                2980                3000

TACATTATATATAATTCTGTTGTTTCTGCAATTGACTTTTCTCTGGCTTTTCTTTGCCAC
              3020                3040                3060

GTGACGATTCCGGTTTTTACTTTCTTTCTTTTTTTTTTATCAATTTCTCAGACACATTTG
              3080                3100                3120

ATGAACATCTCGCTCTCATCTAATCGTTAACTATTTTTATTGGGGTAAATGTCTGGATTT
              3140                3160                3180

GTCTTACCTAAACATGTTTTAAGACTGATGTTTATGCAGAGTGAAAACAGTAAATAATTT
              3200                3220                3240
```

FIGURE 3 (VI)

```
AATGCTTTATTCAATCCCTATGCAATGGATCTCAACTTAACGGCGCCAACCAGAGAGTTT
         3260                    3280                    3300

TACTAACTGTCTTTGCTTTAGTTAATATTCCTAATAAATAAAAGACTGCCAATAATA
         3320                    3340                    3360

AAATCGGACCATTTTATTCTCATAATAAAAGAAGCTCAAGGAGGTCCCTCCTAC
         3380                    3400                    3420

ACTTTTCTGACTCCTTATGTTCTGTTCTCTGTGATTCATTAACGGATCAGCTATAGCAT
         3440                    3460                    3480

TTCCAATTTGTCAGTAAGTTAGGGTTGGTTTGGATTAGCTAATAGCTACCAATGAG
         3500                    3520
```

FIGURE 4

Sequence Range. 1 to 584

|           |            |            |            | 50         |
|-----------|------------|------------|------------|------------|
| MSPPSATAGD | INHREVDPTI | WRACAGASVQ | IPVLHSRVYY | FPQGHVEHCC |

|           |            |            |            | 100        |
|-----------|------------|------------|------------|------------|
| PLLSTLPSST | SPVPCIITSI | QLLADPVTDE | VPAHLILQPI | TQQQPTPTNY |

|           |            |            |            | 150        |
|-----------|------------|------------|------------|------------|
| SRPGRPDGDV | DDNNKVTTPA | KILTPSDANN | GGGPSVPRPC | ADSVPPLLNP |

|           |            |            |            | 200        |
|-----------|------------|------------|------------|------------|
| QIDPPVQKLY | VTDIHGAVWD | FRHIYRGTPR | RHLLTTGWSK | PVNSKKLIAG |

|           |            |            |            | 250        |
|-----------|------------|------------|------------|------------|
| DSVVPMRKSA | DEMYIGVRRT | PISSSDGGSS | YYGGDEYNGY | YSQSSVAKED |

|           |            |            |            | 300        |
|-----------|------------|------------|------------|------------|
| DGSPKKTPRR | SGNGKLTAEA | VRSINRASQG | LPPEVVFYPA | AGWSEPVVRA |

|           |            |            |            | 350        |
|-----------|------------|------------|------------|------------|
| EDVESSMSMY | WTPGTRVKMA | METEDSSRIT | WPQGIVSSTY | QETGPWRGSP |

|           |            |            |            | 400        |
|-----------|------------|------------|------------|------------|
| WKQLQITWDE | PEILQNVKRV | NPWQVEIAAH | ATQLHTPFPP | AKRLKYPQPG |

|           |            |            |            | 450        |
|-----------|------------|------------|------------|------------|
| GGPLSGDDGE | ILYPQSGLSS | AAAPDPSPSM | PSYSTFPAGM | QGARQYDPGS |

|           |            |            |            | 500        |
|-----------|------------|------------|------------|------------|
| PNPTGPIGGN | PPQLPTNNFL | SPLPDLGKVS | TEMMNPGSPP | SDNLSPNSNT |

|           |            |            |            | 550        |
|-----------|------------|------------|------------|------------|
| TNLSSGNDLV | GNRGPLSKKV | NSIQLPGKII | TVEEHSESGP | AESGLCEEDG |

| SKESSDNETQ | LSLSHAPPSV | PKHSNSNAGS | SSQG |

FIGURE 5
LIST OF PRIMERS

Ac11    5' CGTATCGGTTTTCGATTACCGTATT 3'    25-mer
located at position 4419-4443 on Ac sequence

Ac14    5' CGTTTCCGTTTCCGTTTACCGTTTT 3'    25-mer
located at position 145-127 on Ac sequence

W2    5' TGCTTGTGCTGGAGCC 3'    19-mer
located at position 221-237 on 41-a genomic sequence
Concentration : 5296 ng / ul
               1.0633 nmoles / ul

Z3    5' GTTATCATCAACATCGCCATCGAATCTGCCG    31-mer
located at position 495-465 on 41-a genomic sequence
Concentration : 13811 ng / ul
               1.4555 nmoles / ul

G6 5'-11    5' CTGCTGCTGCGTGATCGG    18-mer
located at position 438-421 on 41-a sequence
Concentration : 4943 ng / ul
               0.8828 nmoles / ul

Comments
Lenght of amplification product
     W2/G6 5'-11      217bp
     W2/Ac 11      240bp
     Ac 14/G6 5'-11      265bp

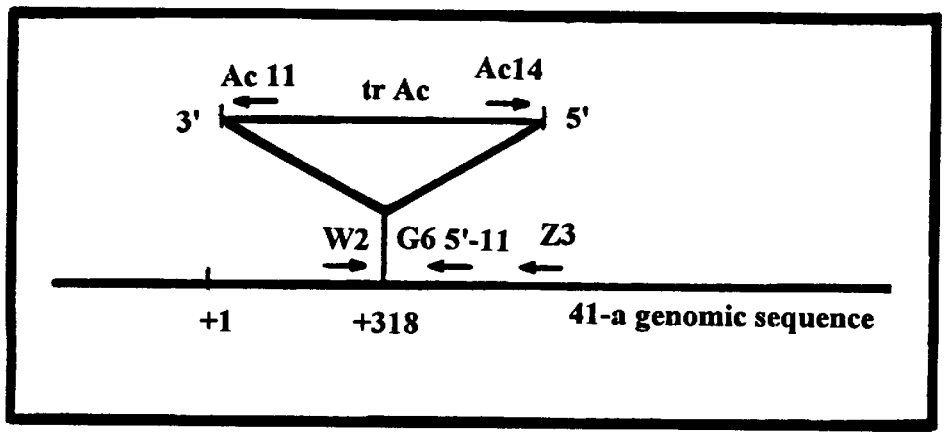

FIGURE 6

| Wild type Sequence | Cys Pro TGC CCT | | | Leu Leu Ser Thr Leu CTC CTC TCT ACT CTT | Alleles |
|---|---|---|---|---|---|
| Female A or B | TGC CCT | CTC CTC TC | (3' Ac 5') C TCC TCT C | TA CTC TT | ms 41:: 35S Ac |
| | TGC CCT | CTC CTC | AG | T CCT CTC TAC TCT T | ms 41-1 (+7 bp) |
| Male parent | TGC CCT | CTC CTC TC | (3' Ac 5') C TCC TCT C | TA CTC TT | ms 41:: 35S Ac |
| | TGC CCT | | | CTC CTC TC T ACT CTT | Ms 41 |
| Revertant H | TGC CCT | | | CTC CTC TC T ACT CTT | Ms 41-R |
| | TGC CCT | CTC CT | | C TCC TCT C TA CTC TT | ms 41-2 (+5 bp) |
| Revertant K | TGC CCT | | | CTC CTC TC T ACT CTT | Ms 41-R |
| | TGC CCT | CTC C | AG | TCC TCT C TA CTC TT | ms 41-3 (+5 bp) |
| Revertant F | TGC CCT | | | CTC CTC TC T ACT CTT | Ms 41-R |
| | TGC CCT | CTC CTC T | G | T CCT CTC TAC TCT T | ms 41-5 (+7 bp) |
| Revertant C | TGC CCT | | | CTC CTC TC T ACT CTT | Ms 41-R |
| | TGC CCT CTC CTC T | | GA G | TC CTC TC T ACT CTT | ms 41-4 (+9bp) |
| Revertant M | TGC CCT CTC | | | CTC CTC TC T ACT CTT | Ms 41-1R (+3 bp) |
| | TGC CCT CTC CTC | | AG | T CCT CTC T ACT CTT | ms 41-1 (+7 bp) |
| Revertant A | TGC CCT CTC | | | CTC CTC TC T ACT CTT | Ms 41-1R (+3 bp) |
| | TGC CCT CTC CTC TC | | (3' Ac 5') C TCC TCT C | TA CTC TT | ms 41:: 35S Ac |
| Revertant L | TGC CCT CTC CTC | | G | T CCT CTC TAC TCT T | Ms 41-2R (+6 bp) |
| | TGC CCT CTC CTC TC | | (3' Ac 5') C TCC TCT C | TA CTC TT | ms 41:: 35S Ac |

Footprints are alleles induced by 35 Sac excision from the ms 41-a locus

FIGURE 7
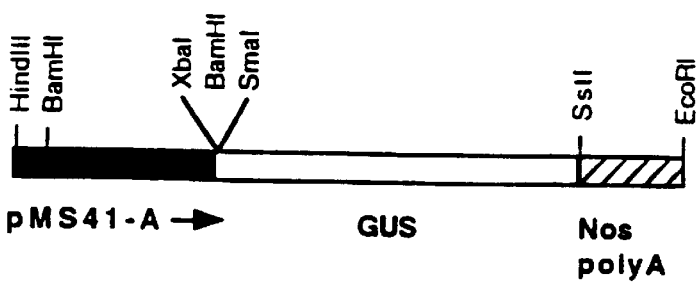
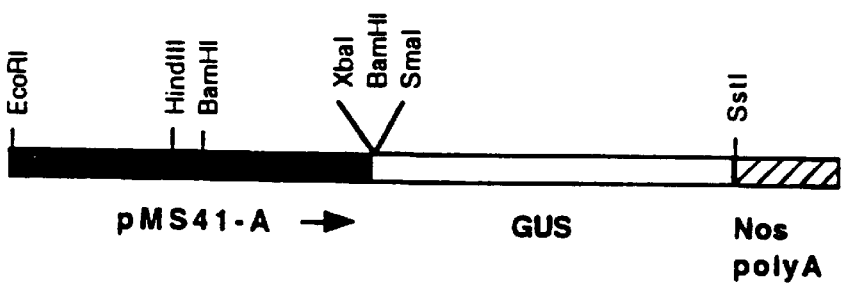
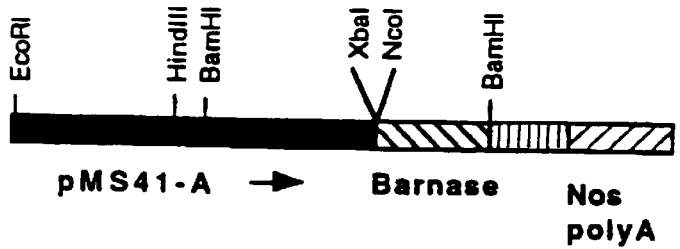

FIGURE 9

Clustal Alignment of 41a related sequences

```
ZmVP1    515 ..........................................LLQKVLKQSDVGS
OSR1187    1 ...........................................EKRLTPSDVGK
ATTS3975   4 LRKHTYNEELEQSKRRRNGNGNMTRTLLTSGLSNDGVSTTGFRSAEALFEKAVTPSDVGK
At41a     73 LADPVTDEVFAHLILQPITQQQFTPTNYSRFGRFDGDVDDNNKVTT--FAKILTPSDANN
OSS2204    1 ..............................AVKRLARIPHMFCKTLTASDTST
Zm41a      1 ....................DGSAEDGVRKGETVKQRFSRMPHMFCKTLTASDTST
                *      .*    .   . *                         . *.  **

|ZmVP1     LGRIVLPKKEAEVHLP----ELKTRDGISIPMEDIGTSRVWNMRYRFWPNNKSRMYLLEN|
|OSR1187   LNRLVIPKQXAERYFXLGGGDSGX-KXCLLLSXEDES-GKPWRFRYSYWTSSQS--YVLXK|
|ATTS3975  LNRLVIPKHHAEKHFPLPSSNVSV-KGVLLNFEDVN-GKVWRFRYSYWNSSQS--YVLTK|
|T21748    LNRLVIPKQHAEKHFPLPSPSPAVTKGVLINFEDVN-RKVWRFRYSYWNSSQS--YVLTK|
|At41a     GGGFSVPRFCADSVFPLL--NFQIDPPVQKLYVTDIHGAVWDFRHIYR--GTPRRHLLTT|
|OSS2204   HGGFSVPRRAAEDCFPPL--DYSLQRPFQELVAKDLHGTEWRFRHIYR--GQPRRHLLTT|
|Zm41a     HGGFSVPRRAAEDCFPPL--DYSQQRPSQELVAKDLHGTEWRFRHIYR--GQPRRHLLTT|
|              ..*.  *. .                                 *  *  ..   .  .*

ZmVP1     T-GEFVRSNELQEGD
ATTS3975  GWSRFVKEKNLRAGD
T21748    -GWSRFVKEKNLRAGN
ATTS1074  1.........................GFSGFLRDDESTTTTSKLM
At41a     GWSKFVNSKXLIAGDSVVFMRKSADEMYI-GVRRTPISSSDGGSSYYGGDEYNGYYSQSS
OSS2204   GWSGFINKKKLVSGDCSAIPQEVKMENFDWGVRRAA-QLKNAISF
Zm41a     GWSAFVNKKKLVSGD
             .*. .* *.         .      *. ****..   .  *  .**        *.

ATTS1074  MMKRNGNNDGNA---AATGRVRVEAVAEAVARAACGQAFEVVYYPRASTPEFCVKAADVR
At41a     VAKEDDGSPKKTFRRSGNGKLTAEAV-RSINRASQGLPFEVVFYPAAGWSEFVVRAEDVE
            .*   ...  ..    *..  ***    ** *  ****.** *.  ** *.* **

ATTS1074  SAMRIRWCSGMRFKMAFETEDSSRISWFMGTVSAVQVADPIRWPNSPWRLLQVAWDEPDL
At41a     SSMSMYWTPGTRVKMAMETEDSSRITWFQGIVSST-YQETGPWRGSPWKQLQITWDEPEI
          *.*  *   * * **.*********.**  *..   *   **.. **  ** .*****..

At41a     LQNVKRVNPWQVEIAAHATQLH-TPFPPAKRLKYPQP--------------GGGFLSGDDG
ATTS1074  LQNVKRVSPWLVELVSNMPTIHLSPFSPRKKIRIPQPPFEFPFHGTKFPIFSPGFANNGGG
          *******.**  *...*.*. .  .* .*.*.* ***                 *.   .*

At41a     EILY--------PQSGLSSAAAPD-----PSPSMFS---YSTFPAG--MQGARQYDFGSF
ATTS1074  ESMCYLSNDNNNAPEGIQGARQAQQLFGSPSPSLLSDLNLSSYTGNNKLHSPAMF-LSSF
          *            .*.*        ****..*   *       .   ..  **

At41a     NPT---------------GFIGGNPPQ-----------------LFTNNFLSPLPDLG
ATTS1074  NPRHHHYQARDSENSNNISCSLTMGNPAMVQDKKKSVGSVKTHQFVLFGQPILTEQQVMN
          **                  ***.                     **    .*.

At41a     KVSTEMMNFGSPPSDNLSPNSNT-----TNLSSGN-------DLVGNRGPLSKKVNSIQL
ATTS1074  RKRFLEEEAEAEEEKGLVARGLTWNYSLQGLETGHCKVFMESEDVGRTLDLSVIGSYQEL
          .        *  . *    * .*       *.*         **     .   * .*

At41a     FGKI---ITVEEHSE-----SGPAESGLCEEDGSKESSD-----NETQLSLSHAPPSVPK
ATTS1074  YRKLAEMFHIEERSDLLTHVVYRDANGVIKRIGDEPFSDFMKATKRLPIKMDIGGDNVRK
          . *.    .  **.*.         .*  * *    **                . * *

At41a     HSNSNAGSSSQG---------------
ATTS1074  TWITGIRTGENGIDASTKTGPLSIFA
                                *
```

FIGURE 10

Zm41a 5 prime DNA sequence and proposed ORF

```
1    AGGACGGCAGCCCGAGGACGGGTACGGAAGGGGAAACCTGAAGCAGCGGTTCTGC      60

TCCTGCCTCCGGGCTCCTGCCATGCCTCCCCTTTGCCACTTCTGTCGCCAAGAGCG     120
       D  G  S  A  E  D  G  V  R  K  G  E  T  V  K  Q  R  F  S  R

61   GGATGCCGCACATGTTCTGCAAGACGCTCACGGCCTCCGACACCAGCACGCACGGGGGTT 120
      M  P  H  M  F  C  K  T  L  T  A  S  D  T  S  T  H  G  G  F

CCTACGGCGTGTACAAGACGTTCTGCGAGTGCCGGAGGCGTGTGCGTGTGCTGCCCCCAA 180
      S  Y  G  V  Y  K  T  F  C  E  C  R  R  R  V  R  V  L  P  Q ???

121  TCTCCGGTGCCGCGCCGCCGAGGACTGCTTCCCGCCTCTGGACTACAGCAGCAGC      180
      S  V  P  R  R  A  A  E  D  C  F  P  P  L  D  Y  S  Q  Q  R

AGAGGCACGCGCCGCCGCCGAGGCCTCGAGGAAGGGCGAGACCTGATGTCGTGTCG    240

181  GACCGTCGCAGGAGCTTGTGGCCAAGGATTGCACGGAACCGAGTGGAGTTCCGCCACA   240
      D  R  R  S  L  V  A  K  D  L  H  G  T  E  W  R  F  R  H  I

CTGGCAGCGTCCTCGAACACCGGTTCCTAAACGTGCCTTGGCTCACCTCCAAGCGGTGT   300
      P  S  Q  E  L  V  A  K  D  L  H  G  T  E  W  R  F  R  H  I  ???

241  TTTATCGAGGCGCCCAGCCCCCAGACACCTTTAACCACTGGATGAGTGCCTTGTCAACA   300

AAATAGCTCCCGTCGGGGTCTGTGGAAAATGGTGACTACCTCACGGAAACAGTTGT      
      Y  R  G  Q  P  R  R  H  L  L  T  T  G  W  S  A  F  V  N  K

301  AGAAGAAGCTTGTCTCAGGGGAC                                     323
     TCTTCTTCGAACAGAGTCCCCTG
      K  K  L  V  S  G  D
```

Dendrogram based on the clustal alignment of 41a related sequences

FIGURE 12 (I)

```
                                                                              70
                                                                               *
aagctttagt gactagtgag agtgatttgt tgtgttcttt tgagctcttg cgcttggatt gctttcttct 140
                                                                               *
ttctcattct ttcttgagat caatactcac ttgtaaccga ggcaagagac accaattgtg tggtggtcct 210
                                                                               *
tgcgggtaag ttttgttccc ggttgatttg agaagagaaa gctcactcgg tccgagggac cgtttgaaag 280
                                                                               *
agggaagggg ttgaaaaaga cccggccttt gtggcctcct caatggggag taggtttgcg aaaaccgaac 350
                                                                               *
ctcggtaaaa caaatccgcg tgtcacactt cttatctgct tgcgatttgt ttttcaccct ctctcgcgga 420
                                                                               *
ctcgattata tttctaacgc taacccgact tgtagttgtg attaactttg taaatttcag tttcgcccta 490
                                                                               *
ttcaccgccc tctatgcgac tttcagtagt tcatctatcc catgttttac ccctatttgc ttggatctga 560
                                                                               *
gctgattgcg acttagagac taaactgctg aacttatgaa cctgtaaata aaatactaag taaactagtt 630
                                                                               *
agtccgaatg tttgtgatag tcatcaagca ccaaaatcaa tataaaaatg gtttaaggcc aatttccttt 700
                                                                               *
cgcaaagata tggaatgtca taccccgtca atccttcatg taacaatggt cgtgcgttcc ctcaaccata 770
                                                                               *
caaagggaca tggccgcact gaaaaggcag acacacatag ttttacatat tttctacgct agcacaatag 840
                                                                               *
cctcgttctc cactctgcaa ctcacgaaaa cagtaacaaa aacttcaaca acatactagg catattttct 910
                                                                               *
ctccaaactg gtctaaaaac tctcttcaaa ctcacttcga gcaaggtaat cgggacatta gcaccgcaat 980
                                                                               *
cccttccta aactccaatc tacttgtcat ggggttgaaa tcacgatagt taatgtgcta ggtaaggggt 1050
                                                                               *
atggcgcgtt gcatttagct ttcgatggga ttcgatcgtt ttcccatgac gccttcactc tcgaaaccaa
```

FIGURE 12 (II)

```
                                                                            1120
                                                                              *
tgtcacattt tgagatcttg gactttgttt ccaccaaggg attgcgccat gcagctcctc acccgcgtcc 1190
                                                                              *
ggacggtagc acacgagagg aaccatgaag gcgccttcga catgcgggcc ttggatgggt cgacgaaaaa 1260
                                                                              *
ggtcctaggt tcgcggccta atgtcgcacg acccgatgct tcgtacaagg tctatagaac ggttagggca 1330
                                                                              *
taagggcacc tagttcaaaa aactcaaaag ggcccaaccg agggtagggt tggcagcggg cgacgaagcg 1400
                                                                              *
aatatagccg cacgtgccac cacacaaaat gagggctaat cttcgatgtc gcaccgtcta ggacccatca 1470
                                                                              *
tgcatgtagg atccatcttc gatgtcaatc acgatccctc atgctcttac gacctcctcg acacgccttc 1540
                                                                              *
gtgcgattgc tagaggacat tgtcgacgga atatccctc tttgccctgt gacttggatg attatacatt 1610
                                                                              *
tatggtaggt gttatggatg ttataaatgg atgtatatga atgtgtgtgt atctatgtgt tgtggatgaa 1680
                                                                              *
tataaataat tattttctaa ctggtaagaa tcatttctgg tgactaggtt cagtcgataa aaattagtat 1750
                                                                              *
gtctaatttg tgtattatgt ctatgaaaat tagttaattt tagtttatta atcttcaaaa gttacagacc 1820
                                                                              *
gacgaaaact agactatcag tcacaactgg taagaaggaa caacgacaac agagatgcca agttactggc 1890
                                                                              *
ttactgcagc aagctaccgt tttctgcccg cgtgtacatt gaagcacagg tgcgtctaca ctctacgctc 1960
                                                                              *
tcgagtccaa tataaaata gactgttggg cacctattgt acccgtaccc ctgttcctgc tcctgccgca 2030
                                                                              *
gtactgaatt ctgctgctgc tacactcctc tgtccgcatc catccacgtc tctctcctct gccgccgcc 2100
                                                                              *
tgcgccaccc atcactgtgc gcgtctcccg catcgtccgc tctctttctt tttcacccct tcccggccca
```

FIGURE 12 (III)

```
                                                                      2170
                                                                       *
tcttctcttt ttacatctgc aacggcaggc cggctgcggc agcggcagcg gcagctgacc agtgaccgac 2240
                                                                       *
cacccccaca ccactccggc gccccaatcc tccccttct tcttttcac tactactact gtactgcacg 2310
                                                                       *
gtcgccaagc gccagaacgc agtggagaac gggggcagg actccaacaa gcgttgattt ctgccggcac 2380
                                                                       *
gcacggcacg ggcacgggca cgggcacggg cgtccccct cactcacgca ccctgcgtct tttccggctg 2450
                                                                       *
ccgctgctgg ctggctggct ctggctcaca gctacaggct acagtgaccg ccacgcaacc cacactgtct 2520
                                                                       *
ctgtcctcgt ctccctctcc cctcctagct ctagctggat aggtgggctc tggggaggag gaggagggta 2590
                                                                       *
gctaggtagt agctgcctat aggcctcggc cccattcat ggccattacc acgatgtgtc accccaccac 2660
                                                                       *
accgccctct ccgatgctgc ctccctcatg ataaccctct ccctggtggt tgttctttgc cttgttgccg 2730
                                                                       *
tgcagcctcc accccaccc tcctcattaa tcacttgcta gctccctgcc tccctcccgg ctcccgctcc 2800
                          ◆                                            *
cccttctcgt gcttcgcgcc cccgcagcag ccATGGCGGG GATCGACCTC AACGACACCG TGGAGGAGGA 2870
                                                                       *
CGAGGAGGAG GCGGAGCCCG GCAACGCCTG CTCCCAGCAG AGCCGGACCA GCTCCGCGGC CACGTTCCCG 2940
                                                                       *
CCGCCGCCGC CGAACCAGCC GAGGCCGAGC GCCGCGGTGT GCCTCGAGCT GTGGCACGCC TGCGCCGGCC 3010
                                                                       *
CCGTCGCGCC GCTGCCGAGG AAAGGGAGCG TCGTGGTGTA CCTCCCGCAG GGACACATCG AGCACCTCGG 3080
                          ⁕                                            *
CGACGCCGCG GCCGCCGGCG GAGGCGCGCC GCCGCCCGTC GCCCTGCCGC CCACGTCTT CTGCCGCGTC 3150
                                                                       *
GTCGACGTCA CTCTCCATgt gcgcgcgccg gttcctactc aatgcgtgcg tgtgtggatt gcccgtgccg
```

FIGURE 12 (IV)

```
                                                                   3220
                                                                    *
gtgtgcggct tccactgact ctgtccctct tgcgctcgtt gcagGCGGAC GCGTCCACGG ACGAGGTGTA 3290
                                                                    *
CGCCCAGCTC GCCCTCGTCG CCGAGAACGA Ggtgcgcgca agccacagtg ctccaccggc attggattcg 3360
                                                                    *
gcttggtttt ctccttgcgt ccacagagac gagatttggg ctgatttggt gtttcttgtg gcgcttgctt 3430
                                    ▼                               *
cgtgcagGAT GTCGCGAGGC GGCTGCGCGG ACGGTCGGAG GACGGCAGCG CCGAGGACGG CGACGAAGGG 3500
                                                                    *
GAAACCGTGA AGCAGCGGTT CTCGCGGATG CCGCACATGT TCTGCAAGAC GCTCACGGCC TCCGACACCA 3570
                                                                    *
GCACGCACGG CGGCTTCTCC GTGCCACGCC GCGCCGCCGA GGACTGCTTC CCGCCTCTGg tacgcttgcg 3640
                                                                    *
ttggcttgga aagcttccat cttttgggtg cccggtgct gctctcaagt gcgattctga atcatctgct 3710
                                                                    *
cttggggcgt gcagGACTAC AGCCAGCAGC GACCGTCGCA GGAGCTTGTG GCCAAGGATT TGCACGGAAC 3780
                                                                    *
CGAGTGGAGG TTCCGCCACA TTTATCGAGg tacatgaaca aataatgaga tacaagacga gcacatctac 3850
                                                                    *
ctatttcttt agcaaactta tgtgcttgct cgccctgaat cattcagtgt cagcgaatga tgtcaatggc 3920
                                                                    *
tgcacttcag ttggtgattg ttagcgtttt tttacaggat ttgcattact tgtttggatt gagcacttgg 3990
                                                                    *
gaatgcttca tctttgctca cttaagtcca ggatttgaag tcattgttca gtcactcttt tgctatatat 4060
                                                                    *
gtcaccatta tgtgatcaga actactaatg gttatatgtt gagagagata tacaaactat gtcaatgttt 4130
                                                                    *
cctgctgtct gcatttgcaa ccttgtgcgc tatgctcagc atttctcatg tcattggtta gttattgtag 4200
                                                                    *
tcgtacttaa aatttaccat tttgtccatg aaaaatcatc tgattatatG TTCAGGAGTT CTGGTCCCGT
```

FIGURE 12 (V)

```
                                                                              4270
                                                                                *
TTTAAGGAAT GTAAAAGAAC AAACATGAGA AGCTATGTCA TGTGTGGTCC TTGGTTTCTG ATGAATCTGC
                                                                              4340
                                                                                *
ATCTGAATGT GATGCAGGGC AGCCCCGCAG ACACCTTTTA ACCACTGGAT GGAGTGCCTT TGTCAACAAG
                                                                              4410
                                                                                *
AAGAAGCTTG TCTCAGGGGA CGCCGTACTA TTTTTGAGgt aggccacagc taacattgga gataattatc
                                                                              4480
                                                                                *
acatgttggt gttggccctt tctgaagatt cctcataatt ttcagGGGTG ATAATGGGGA GCTAAGACTT
                                                                              4550
                                                                                *
GGAGTGCGCC GTGCAGCTCA GCTTAAAAAT GGATCTGCTT TTCCAGCTCT TTATAACCAG TGCTTAAATC
                                                                              4620
                                                                                *
TTGGTTCACT ACCTAATGTT GCACATGCTG TGGCCACCAA AAGTGTGTTC CACATCTACT ACAACCCCAG
                                                                              4690
                                                                                *
gtgatgatga atatagcggt ttcacttaa tgcttttgca tgttcaattg ttcatgttgt tggcactctt
                                                                              4760
                                                                                *
ttagatgatg tgaactgaaa tgtgctatta actatactct ttcaattgac ggcgatttga aattgtgtca
                                                                              4830
                                                                                *
ttttgtgtga tatcatttcc tgagttgttt cgaactatgt aattcatgat tcttactgca attcaacatt
                                                                              4900
                                                                                *
aagtgatata taattacttt ttgaattgat attgtcactt acatttggac ccttcaatat aatatagttc
                                                                              4970
                                                                                *
cacagctctt tttttagata tcatgacaag tacgcaagta gatctttggt tccttatgta tctcatgtgc
                                                                              5040
                                                                                *
atttttacct tcttggaccc tgatgtgttg ctgcaagcct tacctttta tccaccaaca atgatggccc
                                                                              5110
                                                                                *
tgatggcaat tattgctttc caaaaatctt acagATTAAG CCAATCTGAA TTCATTATAC CATTTTCGAA
                                                                              5180
                                                                                *
GTTTATCAAG AGCTTCAGTC AACCATTTTC TGCTGGTTCG AGGTTCAAAG TGAAATATGA GAGTGATGAT
                                                                              5250
                                                                                *
GCTTCTGAAA GAAGgttggt gtgctacagt tctcatcttt tacatagatt tatgatggtt gacacatgag
```

FIGURE 12 (VI)

```
                                                                    5320
     agtattatgc agATGCACAG GGATCATAGC AGGAATTGGT GATGCTGACC CCATGTGGCG TGGTTCGAAA 5390
TGGAAATGTT TGATGgtatg ttgcctttta agctttaatg attcactttc tgtataactt ttcaggtggt 5460
aaatttgtgt tacatatgaa aataatccat gttagataca tgttgaatat aacatgtttc tttatacaga 5530
acactaggcg tgtgcatcat gtagctgccg ttgccatcta tttgcactat ttgcttgcta ataaaccaat 5600
aagcaatctt gcatatctat ccaataatac aatgcacaac aaatgttgaa aattgcaatt gagagcctac 5670
tatgcatccc gtgctccctg agctgtctct gtttgatgta caagtttaat tgtaatgaca catttttttt 5740
gcatgtaagt agttctcctt ctccagagca cattctttga tgagcctcat cttagaggca tgttgtatct 5810
ttatctaaaa gagactgcct tgtgccagcc tggtttcctt gatcagggct ctaagtaaat aagttcattt 5880
cattttggtt tcttattgcc ctgcccctga gtgcacattg tagggtaca taatacctc ttgacttagt 5950
aagccagttc taaattgccg caatcttaat cctcttgatg accttacata ttttgtatat aaaccaatgg 6020
ttcatttttg cagGTTCGAT GGGATGACGA TGTAGATTTT CGTCAACCAA ACAGGATTTC TCCTTGGGAG 6090
ATTGAGCTGA CTAGTTCAGT TTCAGGATCT CACATGTCTG CACCAAATGC AAAGAGACTG AAACCATGTC 6160
TTCCCCATGT TAATCCAGAC TACCTAGTTC CAAgtatgcc ctgttctgcc cagatgttcg cttaatgatt 6230
attttgttag cttccgtcat gaataatatt ttcattttga tagATGGAAG CGGTCGTCCT GATTTTGCGG 6300
AATCTGCCCA ATTCCACAAG GTCTTGCAAG GTCAAGAATT ACTGGGTTAT AGAACTCATG ACAATGCTGC
```

FIGURE 12 (VII)

```
                                                                    6370
                                                                      *
TGTTGCAACT TCTCAGCCAT GCGAAGCAAC GAACATGCAG TACATTGATG AACGAAGTTG CTCCAACGAT
                                                                    6440
                                                                      *
GCGAGTAACA TTATCCCGGG GGTTCCAAGA ATTGGTGTCA GAACACCACT CGGAAGCCCT AGGTTTTCCT
                                                                    6510
                                                                      *
ACCGTTGCTC AGGCTTTGGG GAGTCTCCAA GATTCCAAAA GGTCTTGCAA GGTCAAGAAG TATTTCATCC
                                                                    6580
                                                                      *
CTACAGAGGA ACTCTGGTCG ATGCAAGCTT GAGTAATAGT GGCTTCCATC AGCAAGATGG TTCTCATGTG
                                                                    6650
                                                                      *
CCTACTCAGG CCAGCAAGTG GCACGCACAG CTACATGGAT GTGCTTTTCG TGGCCAACAA GCACCAGCTG
                                                                    6720
                                                                      *
TTCCATCTCA ATCCTCATCC CCACCATCTG TCCTGATGTT TCAACGAGGT GATCCAAAGA TGTCCCCATT
                                                                    6790
                                                                      *
TGAATTTGGG CATTTCCACG TGAATAAGAA AGAGGATAGA CGCGCAATGT TTGTCCATGC TGGAGGCATC
                                                                    6860
                                                                      *
GGAGGAACTG AGCAAACGAC GATGCTCCAG GCTCATCATG TTTCTGGAGG AACGGAAAC AGAGATGTGA
                                                                    6930
                                                                      *
CCGTTGAGAA ATCTCATCCC GCTGTTGCCG CTGCTTCAGA CAACAGGGAA GTTAGCAAAA ACAGTTGCAA
                                                                    7000
                                                                      *
AATATTTGGC ATATCTTTGA CCGAGAAGGT TCCAGCAATG AAAGAAAAGG GCTGTGGTGA CATCAACACC
                                                                    7070
                                                                      *
AACTATCCAT CCCCCTTCCT GTCTTTGAAG CAACAAGTGC CGAAATCGCT GGGCAACAGC TGTGCCACCg
                                                                    7140
                                                                      *
tgagtgtcct acaccatgta gcacccttga tgtctttctc gagtgaagta actcttaact attataaaat
                                                                    7210
                                                                      *
cctgcacGTT CATGAGCAGA GGCCTGTTGT TGCTAGGGTG ATTGACGTTT CAACAGTGGA TATGATGATC
                                                                    7280
]                                                                     *
TGATGTATTG GAAAACTGTC CTGGAGgtga agtcatgcta gtaccacctc tgtcttcatg ctagtgacca
                                                                    7350
                                                                      *
tgaacagcat caaagcattt taagctgact gttcttaagc acatcgctta ttgttgttgc cttgtgtttt
```

FIGURE 12 (VIII)

```
tgcaggCTGT GTTGCGTAGT GTGGACAGTG TCGGTTTGAT GGTTCGGTAT CGTGAAGACG GGATTTGATT
                                                                              7420

GAGGATCTGG CCAGATTTGT ATCCTAGTTG TAGCTGTTAG AGCACTTTGT ATGACAACCG TGAGTGCTCC
                                                                              7490

GTGTTATCAG CACTAGTTGC TGCTCACAAC TTGCCTCTAT GTTCATAATC TGTATGCCAT GTCAGACCCA
                                                                              7560

TTTATAGAGG GTTTGTTTGC TTGGCATAGT TCTAGACTTA AAGCATTATT ATGAGAACAA ATTTGCTCTG
                                                                              7630

Caccgtatct ttcttacttt caagttggca acggattaac ggtggaggag atgatctgag aggttagttg
                                                                              7700 tgcgacgtat taatggtgtt acatatatta tgcttaggag cattctgcca gctcattat catatacatg
                                                                              7770 tcagcacttg atttgttaag tgtagttagt agccttgcac tttgg
                                                                              7810
```

FIGURE 14

```
Z31      MAGIDLNDTVEEDEEEAEPGNACSQQSRTSSAATFPPPPPNQPRPSAAVC
Zm41-A   --------------------------------------------------

Z31      LELWHACAGPVAPLPRKGSVVVYLPQGHIEHLGDAAAAGGGAPPPFVALPP
Zm41-A   --------------------------------------------------

Z31      HVFCRVVDVTLHADASTDEVYAQLALVAENEDVARRLRGRSEDGSAEDGD
Zm41-A   -----------------------------------------DGSAEDGD
                                                  ********

Z31      EGETVKQRFSRMPHMFCKTLTASDTSTHGGFSVPRRAAEDCFPPLDYSQQ
Zm41-A   EGETVKQRFSRMPHMFCKTLTASDTSTHGGFSVPRRAAEDCFPPLDYSQQ
         **************************************************

Z31      RPSQELVAKDLHGTEWRFRHIYRGQPRRHLLTTGWSAFVNKKKLVSGDAV
Zm41-A   RPSQELVAKDLHGTEWRFRHIYRGQPRRHLLTTGWSAFVNKKKLVSGDAV
         **************************************************

Z31      LFLRGDNGELRLGVRRAAQLKNGSAFPALYNQCLNLGSLPNVAHAVATKS
Zm41-A   LFLRGDNGELRLGVRRAAQLKNGSAFPALYNQCSNLGSLPNVAHAVATKS
         ********************************* ****************

Z31      VFHIYYNPRLSQSEFIIPFSKFIKSFSQPFSAGSRFKVKYESDDASERRC
Zm41-A   VFHIYYNPRLSQSEFIIPFSKFIKSFSQPFSVGSRFKVRYESDDASERRC
         *******************************.******.***********

Z31      TGIIAGIGDADPMWRGSKWKCLMVRWDDDVDFRQPNRISPWEIELTSSVS
Zm41-A   TGIIAGIGDADPMWRGSKWKCLMVRWDDDVDFRQPNRISPWEIELTSSVS
         **************************************************

Z31      GSHMSAPNAKRLKPCLPHVNPDYLVPNGSGRPDFAESAQFHKVLQGQELL
Zm41-A   GSHMSAPNAKRLKPCLPHVNPDYLVPNGSGRPDFAESAQFHKVLQGQELL
         **************************************************

Z31      GYRTHDNAAVATSQPCEATNMQYIDERSCSNDASNIIPGVPRIGVRTPLG
Zm41-A   GYRTHDNAAVATSQPCEATNMQYIDERSCSNDASNIIPGVPRIGVRTPLG
         **************************************************

Z31      SPRFSYRCSGFGESPRFQKVLQGQEVFHPYRGTLVDASLSNSGFHQQDGS
Zm41-A   SPRFSYRCSGFGESPRFQKVLQGQEIFHPYRGTLVDASLSNTGFHQQDGS
         *************************.***************.*******

Z31      HVPTQASKWHAQLHGCAFRGQQAPAVPSQSSSPPSVLMFQRGDPKMSPFE
Zm41-A   HVPTQASKWHAQLHGCAFRGPQAPAVPSQSSSPPSVLMFQRGDPKMSPFE
         ******************** *****************************

Z31      FGHFHVNKKEDRRAMFVHAGGIGGTEQTTMLQAHHVSGGTGNRDVTVEKS
Zm41-A   FGHFHVNKKEDRRPMFVHAGGIGGTEQTTMLQAHHVSGGTGNRDVTVEKS
         *************.************************************

Z31      HPAVAAASDNREVSKNSCKIFGISLTEKVPAMKEKGCGDINTNYPSPFLS
Zm41-A   HPAVATASDNREFSKNSCKIFGISLTEKVPAMKEKGCGDINTNINTNY--
         *****.******.************************************
```

FIGURE 15 (I)

```
                                                                    70
                                                                     *
gaattcaagg gagaagatga tttatcagca ggctctatga gcacagctgc aaagtcaaga cataattctt 140
                                                                     *
gggcctctgc aggtgattct caccectact ctgacattgc ttgcccttca aaatattca gtcaagacaa 210
                                                                     *
aaaagaactt actaatcaaa tgtcattatc agtcaatact ttaagataag tagaatcgat gtcccatacg 280
                                                                     *
acattctagc cacgcactta aacatgtgcc agatatgttc agatcttgtg attcaacaga cctcgacgcc 350
                                                                     *
gactttcatg tatatctttt aggttgaagc ttttgcttag ttcagtgttg ctatcagaaa gctaaaatta 420
                                                                     *
ttttcttgcc acctcctctg catttttac tgcttcagct cctggtgctt ctaatcgagt actatagaaa 490
                                                                     *
gcatctccct tgataaatcg ttgtgtgcaa ataggggtg cttatataat ccatcattag agtatgaggc 560
                                                                     *
gtgctttatt ctatgtgctt cccacaaaaa gagtagccta ttataaactt tgtattagag cacatgacgt 630
                                                                     *
tctaagtttt gaccacattt ctctactatt atattgcagc cataaagatt caatttttat gttgggcacc 700
                                                                     *
ataaagatgt ttggcaccat tcttcccaaa catttatcta ctattataat gcatgcttta ttcaattttt 770
                                                                     *
agtattgtta ggggtgaagt cttagtctca agatagcata ttgttgtttg cctactccga cgactctgac 840
                                                                     *
gaggctgctg cccgcgcca ggagggaggt caagaagcct aagaagccca agGTGAAGCA ACGATTCTCG 910
                                                                     *
CGGATGCCGC ACATGTTCTG TAAGACGCTC ACGGCCTCCG ACACCAGCAC ACACGTCGGC TTCTCCGTGT 980
                                                                     *
CGCGCaagga cagagcaagc tatgtCATGT GAAGCTATGT CATGTGTGGT CCTTGGTTTC TGATGAATAT 1050
                                                                     *
GCATATGAAT GTGATGCAGG GCAGCCCCGC AGACACCTTT TAACCACTGG ATGGAGTGCC TTTGTCAACA
```

FIGURE 15 (II)

```
                                                              1120
                                                                *
AGAAGAAGCT TGTCTCAAGG GACGCCGTAC TATTTTTGAG gtaggccaca actaacattg gagataatta 1190
                                                                *
tcacatgttg gtgttggccc tttctgaagg ttcctcataa ttttcagGGG TGATAATGGG GAGCTAAGAC 1260
                                                                *
TTGGAGTGCG CCGTGCAGCT CAGCTTAAAA ATGGATCTGC TTTTCCAGCT CTTTATAACC AGTGCTCAAA 1330
                                                                *
TCTTGGTTCA CTACCTAATG TTGCACATGC TGTGGCCACC AAAAGTGTGT TCCACATCTA CTACAACCCT 1400
                                                                *
AGgtgatgat gaatatagcg gtttcacttt aatgttttg catgttcaat tgttcatgtg gttggcactc 1470
                                                                *
ttttagatga tgtgaattga aatgtgctta ttaactactc tttcaattga cggggaattt gaaattgtgt 1540
                                                                *
cattgtgtgt gatatcattt cctgagttgt ttcgagctat gtaattcatg attcttactg caattcaaca 1610
                                                                *
ttaagtgata tataattact ttttgaattg atattgtcac ttacatttgg acccttcaat ataaatcttt 1680
                                                                *
ccaattaatg ctctttttat ccactctttg ttgtcaagtt tctgcaattt agaagtatgc tttcttttgt 1750
                                                                *
atttaattct ttttaggcca cagattgtta tttcttcatg ccataatttc tctgttttat tagtcatagt 1820
                                                                *
aacagaaata tttttcaatt gttgtggcgg ctggccttga ctgctatggc ggtggccgga ctggccagcg 1890
                                                                *
atggcggtgg ccggatagca ccgcgagagc aacgtccaga ggctagcagt tcgttggttg ttgagatttg 1960
                                                                *
taccaatgat tatctatatt tagagttgtt gttggataca cccatccatt tagtccttgt ctatctttta 2030
                                                                *
cacaaccatc taaactataa atttagctag gattataaat aagctgttgg agttgctctt aggtggctcc 2100
                                                                *
tccaatatag gattagtcca tttttctaca aactttgatg tgaattgagt ttctgccaat catgttatat
```

FIGURE 15 (III)

```
atgcatatgt gatgtgaatt gagattcatt gagcaacaca aggattctgt gttggagatg gggtcttaat     2170
                                                                                    *
atttctatca tgtaatatct tttggtagct tgcatcatat taataaaata tcttiggtgg cctcaggtct     2240
                                                                                    *
ggtggtaatg cttatgtgat tggtgattct gcaaagcctg agcagaagtg gcacgcctac tatgccacta     2310
                                                                                    *
ctgagcaccc ctgaggagct tgttgttact cttaacatgt gcatgactgg gctggacaag aagagagctt     2380
                                                                                    *
ctgtcttctt ctaggcttct gctgatggtt acacatcttg tgctaaggag atgaccaagc tctcaggtat     2450
                                                                                    *
ctcggacatt atcctataga cagagatctg cgactaattt gttaggttgg ttcttcatca tttgtagat      2520
                                                                                    *
                                                                     2580
                                                                        *
gcccttcctt ctcgctacat gaactaacta atgacagagg gtggaagtga cccatgaagc tt
```

FIGURE 16 (I)

```
                                                                              70
                                                                               *
gtcgacctgc aggtcaacgg atctattgaa ccagcagtct ttgcaattga gatttgactg ccggatttgg
                                                                             140
                                                                               *
tttcagcatg gatgcaccac cccacatcat gtggttctag agcatatagt ggtcttgtag cgcctaaaag
                                                                             210
                                                                               *
ttttagtagc atcaaatgtc agaaatatat cttcatctcc agaaaatatt agtacttcat aggatgaaaa
                                                                             280
                                                                               *
ttgttcaacc tgaaataatt tatttcttgc atccttcagg ttgtatgcga aaccactaga ttgaataatt
                                                                             350
                                                                               *
caagaaatct acagaggcag tcgtgaacaa ctatatatgc gcaagattga gcctaaggtt tgtagaccct
                                                                             420
                                                                               *
ttaattcata caagggcatt gccatttccc ccgtaatttc gatgcagctc ctttagccat ataacaatga
                                                                             490
                                                                               *
aaaccaacga tcctgcaatc ctgaaagggt gaatttatgg gagaagcgta caactccttt agccaatgat
                                                                             560
                                                                               *
tccaatgaag caccagccta caagaataag atagataaat taacagggta taaaaatgat actaatcaca
                                                                             630
                                                                               *
tgtagtaaaa gaaacttaat ccttccactg catcacgtat atgtgagtgc tccctggttt ttcattacag
                                                                             700
                                                                               *
tcttgtgatt tccattttat gctcgatgta ggtataggca tctgatggag gacgttttgt ctctactccc
                                                                             770
                                                                               *
gcatgtgaag aaggacaacc aggacaaggt cgagtccaag cagagcaagg gaacacgct gaacaagttg
                                                                             840
                                                                               *
cttgagttca ggagctgctt cagctgcctt tcttcgaggt atagatattc tactgtgcct ccacacagct
                                                                             910
                                                                               *
ggtggaaatt ttgttatcat agatacgatg gcggctgctt acatgtggga atcttacact gtataagtca
                                                                             980
                                                                               *
gtggcgcaaa tcaaatctcc aacttgggtt tggtccacct tcgtgaaat gaatgttttc tgggctttca
                                                                            1050
                                                                               *
ggtattgagt aaggagctcc cattttgctc tggtgccaaa ttctctacta ggcaattgac gttttactg
```

FIGURE 16 (II)

```
                                                                        1120
                                                                         *
catttgtgac atctgccttc ccacaattat aattgttcaa tatatgtatg cattagactt atcaatttta
                                                                        1190
                                                                         *
ttaacttatt gaattgtatg tgcatgaagt tttttctttc atgtattaca ccacatgaca tagttcttta
                                                                        1260
                                                                         *
actaatggca gtgtaccttt tttaaccttt agatggctaa attcaaggga gaagatgatt tattagcagg
                                                                        1330
                                                                         *
ctctatgagc acagctgcac agtcaagaca taattcttgg gcctctgcag gtgattctca ccctacgct
                                                                        1400
                                                                         *
gacattgctt ggccttcaaa aatattcagt caagacaaaa agaacttact aatcaaatgt cattatcagt
                                                                        1470
                                                                         *
caatactta agataagtag aatcgatgtc ccatacgaca ttctagccac gcacttaaac atgtgccaga
                                                                        1540
                                                                         *
tatgttcaga tcttgtgatt cagcagacct tgacgccgag cgggcctccg cggaggcagt agccagatct
                                                                        1610
                                                                         *
ggccattgag tgcccgacg ccgctgctta ctcatccatc gccgcggtga cctgctcccc ctcgggcata
                                                                        1680
                                                                         *
tctgtccatt gacaccaagc atgttctttc ctgaactgtt ctaaaagttc agtttcatgg ttgtttattc
                                                                        1750
                                                                         *
ttttgatcag gaaggagaga aagggagaat cagttagaag aaagaagagt ctgaaagctg agtaatttac
                                                                        1820
                                                                         *
ctcaacttta ctacccatgt tattaagatc tattgatgat cgtcccactt actcctatga tgcacagact
                                                                        1890
                                                                         *
taatggatca tggactgaca tatttatcac gggttttggg ttgtcttcct tcccagtttt gttttaccag
                                                                        1960
                                                                         *
tggagacacg aagattggag gacataaggg cgcaacacag gactacagcg aggggaagg ccagatcaag
                                                                        2030
                                                                         *
caggagacaa caagaggtgg gttgctgctc attcacaatt tgatatgttt gttttttcgt tgttatagct
                                                                        2100
                                                                         *
gaactgcaca tgcagtttga aacatgttgt tactgatgtg tttgtctatt acaggatgtg atagatggtg
```

FIGURE 16 (III)

```
                                                                          2170
                                                                            *
     atctctgtga gcagtatccc tccctcctag ctgatatgca gaggaagatt gctgatgagc tggacagaag 2240
                                                                            *
     tccgacgcct gcagcactgc ttggtgagga ttgccaagga ggaagactag aacaagcaag agcagcgtta 2310
                                                                            *
     atcagtgaca gagcatgatg ccatccagat gggacaagat aagtaagcag tcttatatag tctgcccact 2380
                                                                            *
     cgagttttgt atatattta ggttgaagct tttgcttagt tcagtgttgc tatcggaaag ctaaaattat 2450
                                                                            *
     tttcttgcca cctcctctgc attgttttgc tgcttcagct cctggtgctt ctaatcgagt actatagaaa 2520
                                                                            *
     gcatctctct tgataaatcg ttgtgtgcaa atataggtg cttatataat ccatcattag agtatgaggc 2590
                                                                            *
     gtgttttatt ctgtgtgctt cccacaaaaa agagtagcct attataaact ttgtattaga gcacatgacg 2660
                                                                            *
     ttctaagttt tgaccacatt tctctactat tataatgcag ccataaagat tcaattttta tgttgggcac 2730
                                                                            *
     cataaagatg tttggcacca ttcttcccaa acatttatct actattataa tgtgtgcttt attcaatttt 2800
                                                                            *
     tagtattgtt aggggtgaag tcttagtctc aagatagcat attgttgttt gcctactccg acgactctga 2870
                                                                            *
     cgaggctgct gccccgcgcc aggagggagg tcaagaagcc taagaagccc aaggtgaaga agcccaagGT 2940
                                                                            *
     GAAGCAACGA TTCTCGTGGA TGCCGCACAT GTTCTGCAAG ACGCTCATGG CCTCCGACAC CAGCATGCAC 3010
                                                                            *
     GTCGGCTTCT CTGTGCTGNG CCGCTCCGCC GAGGACTGCT TCCCGCCTCT Agtacgcttg cgttggnttg 3080
                                                                            *
     gaaagcttcc atcttttcgg tgcccgggtg ctgctctcaa ggtgtgattc tgaatcatct gctcttgggg 3150
                                                                            *
     cgtgcagGAC TACAGCCAGC AGCGATCGTC GCAGGAGCTT GTGGCCAAGG ATTTGCACGG AACCGAGTGG
```

FIGURE 16 (IV)

```
                                                                    3220
                                                                      *
AGGTTCCGCC ACATTTATCG AGgtacatga acaaatactg agatacaagc cgagcacatc tacctatttc 3290
                                                                      *
tttagcaaac ttatgtgctt gctcgccctg aatcattcag tgtcagcgaa tgatgtcaat ggctgcactt 3360
                                                                      *
cagttgatga ctgttagcgc tttttacagg atttgcatta cttgtttgga ttgagcactt aggaatgctt 3430
                                                                      *
catctttgct cacttaagtc caggatttga agtcattgtt cagccactct tttgctatat atgtcaccat 3500
                                                                      *
tatgtgatca gaactaataa tggttatatg tcgagagaga tatacaaact atgtcaatgt ttcctgttgt 3570
                                                                      *
ctgcatttgc agccttgtgc gctatgctca gcatttctca tgtcattggt tagttattgt agttgtactt 3640
                                                                      *
aaaaattacc attttgtcca tgaaaaatca tctgattata tgtTCAGGAG TTCTGGTCCC GTTTAAAGGA 3710
                                                                      *
ATGTAAAAGA ACAAACATGA GAAGCTATGT CATGTGTGGT CCTTGGTTTC TGATGAATAT GCATCTGAAT 3780
                                                                      *
GTGATGCAGG GCAGCCCCAC AGACACCTTT TAACCACTGG ATGGAGTGCC TTTGTCAACA AGAAGCTTGT 3850
                                                                      *
CTCAAGGGAC GCCGTACTAT TTTTGAGgta ggccacaact aacattggag ataattatca catgttggtg 3920
                                                                      *
ttggcccttt ctgaaggttc ctcgtaattt tcagGGGTGA TAATGGGGAG CTAAGACTTG GAGTGCGCCG 3990
                                                                      *
TGCAGCTCAG CTTAAAAATG GATCTGCTTT TCCAGCTCTT TATAACCAGT GCTCAAATCT TGGTTCACTA 4060
                                                                      *
CCTAATGTTG CACATGCTGT GGCCACCAAA AGTGTGTTCC ACATCTACTA CAACCCCAGg tgatgatgaa 4130
                                                                      *
tatagcggtt tcactttaat gcttttgcat gttcaattgt tcatgttgtt ggcactcttt tagatgatgt 4200
                                                                      *
gaactgaaat gtgcttatta actactcttt caattgacgg ggatttgaaa ttgtgtcatt gtgtgtgata
```

FIGURE 16 (V)

```
                                                                            4270
                                                                              *
tcatttcctg agttgtttcg agctatgtaa ttcatgattc ttactgcaat tcaacattaa gtgatatata 4340
                                                                              *
attactttt gaattgatat tgtcacttac atttggaccc ttcaatataa atctttccaa ttattgctct 4410
                                                                              *
ttttatccac tctttgttgt caagtttctg caatttagaa gtatgctttc ttttgtattt aattctttt 4480
                                                                              *
aggccacaaa ttgttatttc ttcatgccat aatttctctg ttttattagt catagtaaca gaaatatttt 4550
                                                                              *
tcaattgttg tggcggctag ccttgactgc tatggcggtg gccggactgg cctgagatgg cggtggccgg 4620
                                                                              *
atagcaccgc gagagcaacg tccagaggct agcagttcat tggttgttga gatttgtacc aatgattatc 4690
                                                                              *
tatatttaga gttgttgttg gatacaccca tccatttagt ccttgtttat cttttacaca gccatctaaa 4760
                                                                              *
ctctaaattt agctaggatt ataaataagc tgttggatgc tcttaggtgg ctcctccaat ataggattag 4830
                                                                              *
tccattttc tacagatggg gtgatagcat gcacattcta gcatacacat gcccttggcc tggtaatgct 4900
                                                                              *
tggattttt tctcacgcaa aagaatatac cggttcgttg aattatgtga tgtcattttc tactttctg 4970
                                                                              *
tttttagcc gatcatccga aggctaatga atattaccct gacccaagat tagtagcata tgttgtaccc 5040
                                                                              *
tatgcaccta tcctatcgtg gtatcactaa tccttctaaa tttgatatca tcttatctga ttcagcttgt 5110
                                                                              *
tacttgattt aatttggctc cttgttaaca gtacggatgc tgcaaaaaat tccctgagga gaaaggttga 5180
                                                                              *
aatcttaaaa ttgaagcctc attggtccaa agcttacttc tatttgtggg atgaggtgcg ttattttacc 5250
                                                                              *
ttttctgcta tgtcctgatt tcaggggaca ccagtgcaga tgcatgtagg gagaaacttg ttgcagttac
```

FIGURE 16 (VI)

```
agaaatggtt tccaatatct actcttgcaa ttgaagatat ggagttactc cttgggttct ccttttagtt    5320
                                                                                  * ttattatgct cgtccagtag acatgctcct gtagtaaact tatattcatg cttgtaattc cattacaat      5390
                                                                                  * gtgaatattg tgtatagtag ccatgacatg ataatagatt gttaggtca ctcatcaaat attactatgt      5460
                                                                                  * gccgtcacaa atatgggcac tccactaggg tttaggtttt tacctgttgt gcccagttag ggtcactcat     5530
                                                                                  * caaatattac agagggtatg ttccattac agttggagta gatacgcatg acgggggcgc acatgagtta      5600
                                                                                  * ttagtcttgt cgggatctca tgagtctgat tgacgtattt cggatggctc tcgacgtgcg ggtcgacgac     5670
                                                                                  * ggaacacttg cagcgcccat gttcggatgc agcgacagcc tccttgtgtc ttcgaactcg cgacgagaga     5740
                                                                                  * gagtggtatt caggactgct tgcttacagg agagaaataa gctaatttct cagaatctta gaagctgatt     5810
                                                                                  * ttacaacagg attgcttgct tacagagttg atcaactaaa aagcgctat ggttcagaat tc              5870
                                                                                  *
```

DNA SEQUENCES CODING FOR A PROTEIN CONFERRING MALE STERILITY

This application is a continuation of PCT International Application No. PCT/GB96/03191, filed Dec. 20, 1996, designating the United States of America and claiming priority of Great Britain Patent Application No. 9526218.4, filed Dec. 21, 1995.

FIELD OF THE INVENTION

This invention relates to recombinant, isolated and other synthetic DNA useful in male-sterility systems for plants. In particular, the invention relates to a gene associated with male fertility, labelled Ms41-A, and a recessive mutant form thereof, labelled ms41-A, which confers male sterility. Male-sterile plants are useful for the production of hybrid plants by sexual hybridisation.

Hybrid plants have the advantages of higher yield and better disease resistance than their parents, because of heterosis or hybrid vigour. Crop uniformity is another is advantage of hybrid plants when the parents are extensively homozygous; this leads to improved crop management. Hybrid seed is therefore commercially important and sells at a premium price.

Producing a hybrid plant entails ensuring that the female parent does not self-fertilise. There have been many prior proposals, mechanical, chemical and genetic, for preventing self-pollination. Among the genetic methods is the use of anther-specific genes or their promoters to disrupt the normal production of pollen grains. An anther-specific promoter, for example, can be used to drive a "male-sterility DNA" at the appropriate time and in the right place. Male sterility DNAs include those coding for lytic enzymes, including those that lyse proteins, nucleic acids and carbohydrates. Glucanases are enzymes which break down carbohydrates.

WO-A-9302197 describes recombinant or isolated DNA encoding a glucanase called callase.

Aarts et al, (Nature, 363:715–717 (7993)) have described a gene required for male fertility, isolated from Arabidopsis, which has been labelled Ms2.

We have now identified and isolated from Arabidopsis another gene linked to male fertility. This gene has been labelled Ms41-A. Its mutant, recessive, form is labelled ms41-A and is capable of conferring male sterility. This gene would appear to offer advantages over Ms2 when used to produce male sterile plants.

SUMMARY OF THE INVENTION

Thus, in a first aspect the present invention provides recombinant or isolated Nucleic acid which:
 a) encodes the Ms41-A protein from Arabidopsis;
 b) encodes a Ms41-A like protein;
 c) encodes the ms41-A protein from Arabidopsis;
 d) encodes a ms41-A like protein;
 e) comprises a promoter sequence which regulates expression of the Ms41-A protein from Arabidopsis or a promoter sequence which regulates expression of a Ms41-A like protein; or
 f) hybridises under stringent conditions to Nucleic acid a), b), c), d) or e) or would do so but for the degeneracy of the genetic code.

In one embodiment of a) above, the Nucleic acid encodes a protein having an amino acid squence as shown in FIG. 4. Although FIG. 4 relates only to a protein of Arabidopsis, those skilled in the art will readily be able to identify equivalent proteins from other members of the family Brassicaceae or indeed similar proteins from other commercially important plant families, ie Ms41-A like proteins.

In turn the equivalent genes may be identified by hybridisation studies, restriction fragment length polymorphism (RFLP), degenerate PCR and other methods known in the art. Genes or other DNA sequences, whether natural, engineered or synthetic, encoding closely equivalent proteins may for example hybridise under stringent conditions (such as at approximately 35° C. to 65° C. in a salt solution of approximately 0.9 molar) to the Arabidopsis gene, or fragments of it of, for example, 10, 20, 50 or 100 nucleotides. A 15–20 nucleotide probe would be appropriate under many circumstances.

In the context of the present invention, "Nucleic acid which encodes" includes all nucleic acid, eg DNA sequences which will, when expressed, give rise to the protein. Examples of such DNA sequences include, but are not limited to, ones which comprise non-coding regions, e.g introns, sequences which include leader sequences and/or signal sequences, or simply comprise a coding sequence for the protein. The skilled person will also appreciate that, due to codon degeneracy, there will, for example, be a number of DNA sequences capable of coding for the Ms41-A protein or a Ms41-A like protein.

In general, the Nucleic acid of the invention will comprise at least a direct coding sequence for the protein as well as a promoter and transcription termination sequence. The promoter can itself comprise only chose sequences, or elements, necessary for the correct initiation of transcription (which regions can be described as transcription initiation regions, or instance), or, alternatively, it can include regions or sequence which are not directly involved in the initiation of transcription, i.e. a complete promoter can be employed.

A preferred coding sequence described in this specification is from Arabidopsis and can be isolated by methods known in the art, for example by (a) synthesising cDNA from mRNA isolated from Arabidopsis, (b) isolating this cDNA. This cDNA can, in turn, be used (c) as a probe to identify regions of the plant genome of a chosen member of another plant species, eg Maize, that encode mRNA of interest and (d) identifying the upstream (5') regulatory regions that contain the promoter of this DNA.

A particularly preferred DNA sequence is that shown in FIG. 3, and more particularly, the sequence shown in FIG. 3 which commences with the base pair labelled 1, as will subsequently be described in the examples. Those skilled in the art will, with the information given in this specification, be able to identify with sufficient precision the coding regions and to isolate and/or recombine DNA containing them.

The Nucleic acid of the invention can be used to confer male sterility on plants. For instance, the recessive form of the gene, ie ms41-A can be used to transform a plant. Alternatively, the dominant form, ie Ms41-A can be down-regulated in some way.

As discussed herein, the Nucleic acid can include a promoter, and to increase the likelihood of male sterility being conferred it is possible to use promoters which drive expression in particular plant tissues which are involved in the control of fertility. Examples of such promoters are those which are tapetum-specific, for example a Brassicaceae A3 or A9 promoter, described in WO-A-9211379, and the A6 promoter described in WO-A-9302197. Both WO-A-9211379 and WO-A-9302197 are hereby incorporated by reference.

Because of the natural specificity of the regulation of expression of the Ms41-A or Ms41-A like gene, it is not necessary for the Ms41-A promoter to be linked to specific disrupter DNA to provide a useful male-sterility system (although it can be); non-specific disrupter DNA can be used.

Ms41-A like promoters from other plant species, eg from Maize, and modified Ms41-A promoters can be used, and if necessary located or identified and isolated as described above or the Ms41-A coding sequences, mutatis murandis. Ms41-A or Ms41-A like promoter-containing DNA in accordance with the invention can, as indicated above, be used to confer male sterility on plants, particularly those belonging to the family Brassicaceae, in a variety of ways as will be discussed below. In an important embodiment of the invention, therefore, a promoter as described above is operatively linked to DNA which, when expressed, causes male sterility.

Since an effective sterility system is complete, propagation of the seed parent must proceed either by asexual means or via the pollination of the male-sterile by an isogenic male-fertile line, and the subsequent identification or selection of male sterile plants among the offspring. Where vegetative propagation is practical, the present invention forms a complete system for hybrid production. Where fertility restoration is necessary to produce a seed crop, the present invention forms the basis of a new male sterility system. In some seed crops where the level of cross pollination is high, seed mixtures may enable restoration to be bypassed. The male sterility will be particularly useful in crops where restoration of fertility is not required, such as in the vegetable Brassica spp., and such other edible plants as lettuce, spinach, and onions.

Nucleic acid in accordance with the invention and incorporating the Ms41-A or Ms41-A like promoter can drive male sterility DNA thereby producing male sterile plants, which can be used in hybrid production.

A construct comprising a promoter operatively linked to a male sterility DNA can be transformed into plants (particularly those of the genus Brassica, but also other genera such as Nicotiana and Hordeum) by methods which may be well known in themselves. This transformation results in the production of plants, the cells of which contain a foreign chimeric DNA sequence composed of the promoter and a male sterility DNA. Male-sterility DNA encodes an RNA, protein or polypeptide which, when produced or over-produced in a stamen cell of the plant, prevents the normal development of the stamen cell. The Ms41-A or Ms41-A like promoter may be used to drive a variety of male sterility DNA sequences which code for RNAs, proteins or polypeptides which bring about the failure of mechanisms to produce viable male gametes. The invention is not limited by the sequence driven, but a number of classes and particular examples of male sterility promoter-drivable sequences are preferred.

For example, the drivable male sterility DNA may encode a lytic enzyme. The lytic enzyme may cause degradation of one or more biologically important molecules, such as macromolecules including nucleic acid, protein (or glycoprotein), carbohydrate and (in some circumstances) lipid.

Ribonuclease (such as RNase T1 and barnase) are examples of enzymes which cause lysis of RNA. Examples of enzymes which lyse DNA include exonucleases and endonucleases, whether site-specific such as EcoRI or non-site-specific.

Actinidin is an example of a protease, DNA coding for which can be suitable male sterility DNA. Other examples include papain zymogen and papain active protein.

Lipases whose corresponding nucleic acids may be useful as male sterility DNAs include phospholipase $A_2$.

Male sterility DNA does not have to encode a lytic enzyme. Other examples of male sterility DNA encode enzymes which catalyse the synthesis of phytohormones, such as isopentyl transferase, which is involved in cytokinin synthesis, and one or more of the enzymes involved in the synthesis of auxin. DNA coding for a lipoxygenase or other enzymes having a deleterious effect may also be used.

As mentioned above, one way to confer male sterility will be to downregulate the Ms41-A or Ms41-A like gene. This could he achieved by the use of antisense DNA. Introducing the coding region of a gene in the reverse orientation to that found in nature can result in the down-regulation of the gene and hence the production of less or none of the gene product. The RNA transcribed from antisense DNA is capable of binding to, and destroying the function of, a sense RNA version of the sequence normally found in the cell thereby disrupting function.

It is not crucial for antisense DNA solely to be transcribed at the time when the natural sense transcription product is being produced. Antisense RNA will in general only bind with its sense complementary strand, and so will only have its toxic effect when the sense RNA is transcribed. Antisense DNA corresponding to some or all of the DNA encoding the Ms41-A or Ms41-A like gene product may therefore be produced not only while the gene is being expressed. Such antisense DNA may be expressed constitutively, under the control of any appropriate promoter.

It is also the case that one may wish to restore male fertility in later generations, this can also be achieved using antisense nucleic acid, eg nucleic acid which is antisense For a DNA molecule encoding ms41-A.

Thus, in a second aspect, the present invention provides Antisense nucleic acid which includes a transcribable strand of DNA complementary to at least a part of a DNA molecule of the invention.

In one embodiment of this aspect the antisense nucleic acid is under the control of a constitutive promoter, such as the CaMV35S promoter.

A still further example of male sterility DNA encodes an RNA enzyme (known as a ribozyme) capable of highly specific cleavage against a given target sequence (Haseloff and Gerlach *Nature* 334 585–591 (1988)). Like antisense DNA, ribozyme DNA (coding in this instance for a ribozyme which is targeted against the RNA encoded by the Ms41-A or Ms41-A like gene) does not have to be expressed only at the time of expression of the Ms41-A or Ms41-A like gene. Again, it may be possible to use any appropriate promoter to drive ribozyme-encoding DNA, including one which is adapted for constitutive expression.

According to a further aspect of the invention, there is therefore provided DNA encoding a ribozyme capable of specific cleavage of RNA encoded by a DNA molecule of the invention. Such ribozyme-encoding DNA would be useful in conferring male sterility on members of, eg the family Brassicaceae.

In addition, there are other useful methods which can be employed for the downregulation of the Ms41-A or Ms41-A like DNA sequences. Some examples of these are as follows:
  i) expression of an antibody or antibodies, domains or fragments thereof against the Ms41-A or a Ms41-A like protein;
  ii) expression of mutant versions of the Ms41-A or of a Ms41-A like protein which may interfere with the function of the normal protein;
  iii) by creation of mutations in the Ms41-A sequence or the the Ms41-a like sequence with the result that mutant plants can be used in the recessive AMS system as hereinbefore described; and iv) expression of mRNA binding proteins that will interfere specifically with Ms41-A or Ms41-A like transcription.

In preferred embodiments of DNA sequences of this invention 3' transcription regulation signals, including a polyadenylation signal, may be provided. Preferred 3' transcription regulation signals are derived from the Cauliflower Mosaic Virus 35S gene. It should be recognised that other 3' transcription regulation signals could also be used.

Recombinant DNA in accordance with the invention may be in the form of a vector. The vector may for example be a plasmid, cosmid or phage. Vectors will frequently include one or more selectable markers to enable selection of cells transfected (or transformed: the terms are used interchangeably in this specification) with them and, preferably, to enable selection of cells harbouring vectors incorporating heterologous DNA. Appropriate start and stop signals will generally be present. Additionally, if the vector is intended for expression, sufficient regulatory sequences to drive expression will be present; however, DNA in accordance with the invention will generally be expressed in plant cells, and so microbial host expression would not be among the primary objectives of the invention, although it is not ruled out. Vectors not including regulatory sequences are useful as cloning vectors.

Cloning vectors can be introduced into *E. coli* or another suitable host which facilitate their manipulation. According to another aspect of the invention, there is therefore provided a host cell transfected or transformed with DNA as described above.

DNA in accordance with the invention can be prepared by any convenient method involving coupling together successive nucleotides, and/or ligating oligo- and/or polynucleotides, including in vitro processes, but recombinant DNA technology forms the method of choice.

Ultimately, DNA in accordance with the invention (whether (i) Ms41-A gene, ms41-A gene, Ms41-A like gene or ms41-A like gene (ii) antisense DNA to any option listed in i), ribozyme DNA targeted to RNA for any option listed in i) or DNA comprising a promoter as described herein used to drive expression of a disrupter sequence, eg encoding Barnase) will be introduced into plant cells, by any suitable means.

According to a further aspect of the invention, there is provided a plant cell including DNA in accordance with the invention as described above.

Preferably, DNA is transformed into plant cells using a disarmed Ti-plasmid vector and carried by Agrobacterium by procedures known in the art, for example as described in EP-A-0116718 and EP-A-0270822. Alternatively, the foreign DNA could be introduced directly into plant cells using an electrical discharge apparatus. This method is preferred where Agrobacterium is ineffective, for example where the recipient plant is monocotyledenous. Any other method that provides for the stable incorporation of the DNA within the nuclear DNA of any plant cell of any species would also be suitable. This includes species of plant which are not currently capable of genetic transformation.

Preferably DNA in accordance with the invention also contains a second chimeric gene (a "marker" gene) that enables a transformed plant containing the foreign DNA to be easily distinguished from other plants that do not contain the foreign DNA. Examples of such a marker gene include antibiotic resistance (Herrera-Estrella et al. *EMBO J.* 2, 987–995 (1983)), herbicide resistance (EP-A-0242246) and glucuronidase (GUS) expression (EP-A-0344029). Expression of the marker gene is preferably controlled by a second promoter which allows expression in cells other than the tapetum, thus allowing selection of cells or tissue containing the marker at any stage of regeneration of the plant. The preferred second promoter is derived from the gene which encodes the 35S subunit of Cauliflower Mosaic Virus (CaMV) coat protein. However any other suitable second promoter could be used.

A whole plant can be regenerated from a single transformed plant cell, and the invention therefore provides transgenic plants (or parts of them, such as propagating material) including DNA in accordance with the invention as described above. The regeneration can proceed by known methods. When the transformed plant flowers it can be seen to be male sterile by the inability to produce viable pollen. Where pollen is produced it can be confirmed to be nonviable by the inability to effect seed set on a recipient plant.

Preferred features of each aspect of the invention are as for each other aspect mutatis mutandis.

BRIEF DESCRIPTION OF THE DRAWINGS

FIG. 3: (SEQ ID NO:11) shows the genomic DNA sequence of the MS41-A gene. The sequence is numbered from the putative transcriptional start point of the MS41-A message. The predicted amino-acid sequence of MS41-A is shown together with the restriction sites;

FIG. 4: (SEQ ID NO:12) shows the predicted amino acid sequence of MS41-A;

FIG. 5: (SEQ ID NOS:13–17) shows the oligonucleocides used to examine excision events of 35S-Ac from the ms41-A locus;

FIG. 6: shows DNA sequences left by 35S-Ac excision events at the ms41-A locus;

FIG. 7: shows a diagram of the MS41-A promoter-GUS and MS41-A promoter-Barnase chimeric genes;

FIG. 9: (SEG ID NOS:18–25) shows sequence alignments of proteins related to MS41-A;

FIG. 10: (SEG ID NOS:26–27) shows a partial DNA sequence and predicted amino acid translation of Zm41-A;

FIG. 12: (SEQ ID NO:28) shows the nucleotide sequence of the Z31 Zm41-A gene. The portion of the sequence corresponding to putative coding region is shown in bold type capital letters. ♦ indicates putative first methionine deduced in frame with cDNA Zm41-A and 5'RACE products. * indicates the start of the longest 5'RACE product. ▼ indicates the start of Zm41-A cDNA. 12 exons are present and the translation is stopped in exon 11, the stop codon is TGA (☐). Non spliced DNA present in some RACE products is underlined;

FIG. 14: (SEQ ID NOS:29–30) shows clustal V alignment between the protein deduced from the Zm41-A cDNA and from the genomic longest open reading frame of Z31;

FIG. 15: (SEQ ID NO:31) shows the nucleotide sequence of the Z33 Zm41-A gene. The portion of the sequence corresponding to DNA transcription is shown in bold type capital letters. Non spliced DNA present in some RACE products is underlined. This gene is truncated and only exons 3,5 and 6 are present; and FIG. 16: (SEQ ID NO:32) shows the nucleotide sequence of the Z35 Zm41-A gene. The portion of the sequence corresponding to DNA transcription is shown in bold type capital letters. Non spliced DNA present in some RACE products is underlined. This gene is truncated and only exons 3,4,5 and 6 are present.

DETAILED DESCRIPTION OF THE INVENTION

EXAMPLE 1

Figure 1:
FIG. 1: shows a Southern Blot of HindIII-cut genomic DNA from 21 ms41-A plants demonstrating linkage of the 35S-Ac element to ms41-A.

Isolation of a Gene Required for Male Fertility in *Arabidopsis thaliana* i) Isolation and Phenotype of the ms41-A Male Sterile Mutant.

The method used to identify a gene required for male fertility in *Arabidopsis thaliana* was transposon tagging. This method is a powerful technique for isolating genes which encode unknown products, allowing genes identified only by their mutant phenotype, to be cloned. *Arabidopsis thaliana* is a widely used model species that is an ideal plant for transposon tagging of genes, since it is a transformable diploid with a very small genome. Thus the chance of tagging desired genes is maximised. Additionally Arabidopsis is a Brassicaceae and is thus very closely related to important crop plants such as *Brassica napus* (Oil Seed Rape).

Transposon tagging was achieved by transformation of C24 Arabidopsis roots with modified autonomous Ac elements from Maize: D Ac and 35S Ac inserted into the leader of the GUS reporter gene in the reverse orientation (Constructs described in Finnegan et al., *Plant Molecular Biology*, 22:625–633 (1993) (As this work was in progress the first reports of gene tagging with similar Ac elements in heterologous plant species were published; a pH controlling gene from Petunia: Chuck et al., *Plant Cell*, 5:371–378 (1993)); the Arabidopsis DRL1 locus: Bancroft et al., *Plant Cell*, 5:631–638 (1993)) and the *Arabidopsis Albino* gene (Long et al., *Proceedings of the National Academy of Sciences U.S.A.*, 90:10370–10374 (1993)).

Transformed plants were regenerated and the T2 progeny analysed for GUS activity and by molecular analysis. This demonstrated that the 35S Ac transposed quite efficiently (in 30% to 40% of progeny). The T3 progeny families derived from 279 selected T1 plants were then visually screened for mutants affected in male sterility.

A few fertility-reduced or sterile plants were recovered, some possessing additional abnormalities. A male sterile mutant (ms41-A) which appeared in family 41 had collapsed anthers with empty locules. Only one sterile plant was recovered from more than 2000 T3 siblings in this family. After cross-pollination with wild type pollen, elongation of siliques was observed, confirming that female fertility is unaffected by the mutation.

From the above cross 21 F1 individuals were grown and allowed to self pollinate to produce F2 seed ; all the F1 plants were completely fertile suggesting that the mutation is recessive. The first analysis of 6 different F2 populations confirmed the recessive character of the mutation, as male sterility reappeared in a small proportion of each F2 population, with all other siblings presenting a wild type phenotype. Moreover, the vegetative development of the male sterile plants was identical to wild type C24 Arabidopsis. The observed frequency of male transmission of the mutation suggests a non-classical mendelian inheritance for a single recessive mutation—the frequencies of mutant plants in the F2 populations were: 16.8; 13.0; 11.9; 12.7; 15.4 and 17.0%. The expected frequency of mutant plants is 25% or a 3 to 1 ratio of wild type to mutant plants. In this case there is a ratio of approximately 7 to 1 wild type to mutant plants. A homogeneity test on the data of the 6 F2 populations presented concludes that there is homogenous transmission of the male sterile phenotype (Chi square with 5 degrees of freedom=8.69, 0.10<P<0.20).

Proof of reduced transmission of Ms41-A through the male gametophyte was obtained by genetic mapping of Ms41-A. The hypothesis was that markers genetically linked to Ms41-A but present on the homologous chromosome (in repulsion) on a F1 cross with an Ms41-A plant should be over-represented in the derived F2 population. The F1 crosses were made with 5 tester lines, one for each chromosome, constructed by Marteen Korneef (described in; O'Brian S. T. (ed) Genetic maps of complex genomes, Book 6, Plant Cold Spring Harbor Laboratory Press, Cold Spring Harbor, N.Y., pp 94–97 (1990)), and linkage of Ms41-A was demonstrated with markers on the lower part of chromosome 1. Compiled recombination data of 2 populations (476 and 540 individuals) were analysed by the Maps Maker software version 2 (Lander et al., *Genetics*, 121:174–181 (1987))).

Ms41-A is between apetala 1 (8.1 cM) and glabra 2 (9.8 cM) and 40.2 cM away from than chlorina 1. In the first F2 population, the deficit of Ms41-A plants was observed as before (14.7% of plants were male sterile) and it was correlated with the expected increase of apetala 1 and glabra 2 plants (29% and 31.5% respectively); the most distal marker, chlorina 1 behaves quite normally (22.3%). In the second F2, where the penetrance of the Ms41-A is less affected (18.3%), the over representation is not as prevalent (as expected); only the proportion of glabra 2 plants appears co be slightly increased (27.2%).

Microscopic observations of microsporogenesis in the male sterile Ms41-A plants revealed that the tetrads release abnormal microspores which degenerate rapidly. By aniline blue staining the tetrads appear abnormal with irregular shaped cells and with great variation in cell size. Moreover there is a mixed population of meiocytes, dyads (a stage not usually observed in Arabidopsis) and tetrads in the same anther. The defect apparently lies just before or during meiosis. Cytological observations on fixed young anther buds reinforce this finding, since at meiosis the meiocytes are affected but the tapetum behaves normally. No differences were observed cytologically between the Ms41-A heterozygote and wild type plants.

One other gene required for male-fertility (also in Arabidopsis) has been described previously (Aarts et al., *Nature*, 363:715–717 (1993)). Plants with a mutation in this gene (Ms2) were grown together with Ms41-A plants. In certain conditions , especially after the plants had been flowering for a long time the ms2 but not the Ms41-A plants reverted to male fertility.

ii) Linkage of a Transposed 35S Ac with the Mutant Phenotype

To determine if the Ms41-A mutation was due to the insertion of a 35S-Ac element, HindIII-cut DNA from five Ms41-A F1 individuals was analysed by Southern blotting using a 5'Ac fragment (2.5 Kb EcoR I fragment from pBGS335RI (Finnegan et al., *Plant Molecular Biology*, 22: 625–633 (1993)) as a probe. Two identical Ac bands were present in the five mutant plants:

the internal Ac Hind III 1.6 kb band and a junction 3' Ac band of approximately 2.8 kb, which differs from the expected non-transposed 35S Ac (2.1 kb).

This indicates the presence of only one 35S Ac element which has transposed in the parental male sterile plant, or more likely in its parents. To determine linkage between this 35S Ac element and the Ms41-A phenotype, 24 Ms41-A plants from each of 6 different F2 populations were analysed by PCR for the presence of the Ac element using oligo-nucleocides:

5' H (5'AAGGATCCTGGCAAAGACATAAATC 3') (SEQ ID NO:1) and

Ac12 (5'AGATGCTGCTACCCAATCTTTTGTGC 3') (SEQ ID NO:2). The results were as follows

| F2 41-A-A | 23 positives out of 24 |
|---|---|
| F2 41-A-B | 5 " |
| F2 41-A-C | 23 " |
| F2 41-A-D | 10 " |
| F2 41-A-E | 24 " |
| F2 41-A-F | 3 " |

If the Ac element is linked to Ms41-A all male sterile plants should have the Ac element, however if the Ac is not linked only ¾ of Ms41-A plants should have the Ac element. The results obtained indicate complete linkage only in the 41-A-E population. The lack of linkage in the other populations may be due to frequent imprecise excision of the Ac element from the Ms41-A locus leaving a mutation in Ms41-A.

To confirm linkage, the most stable population, 41-A-E, was analysed by Southern blotting with a probe that contained both a region of the transposed Ac element and 3' flanking plant DNA. To generate this probe DNA from a Ms41-A plant was digested with SspI, religated and amplified by PCR using Ac oligonucleotides:

Ac 11 (5'CGTATCGGTTTTCGATTACCGTATT 3') (SEQ ID NO:3) and

Ac 12 (5'AGATGCTGCTACCCAATCTTTTGTGC 3') (SEQ ID NO:4). The 1.1 kb inverse PCR (IPCR) fragment generated contained 500 bp of Ac and the remainder consisted of 3' flanking Arabidopsis DNA.

DNA from plants of the F2 population 41-A-E was digested with HindIII and probed with the 3' IPCR fragment. 21 new F2 mutant individuals and 28 male fertile F2 plants were analysed, the selfed progenies of the latter were checked for the presence of mutant plants revealing that 15 of the 28 were heterozygous for Ms41-A. All of the 21 mutant plants (FIG. 1) and those heterozygotes segregating the mutation in the F3 showed the same transposed 35S Ac revealed by the 2.8 kb specific band and the Ac internal 1.6 kb band. A 3.3 kb band, corresponding to the wild type allele is detectable in most of the F2 mutants; this is probably due to to somatic excision of Ac and confirms that the transposed Ac element is still active. These results confirm that the 35S Ac is located in or in the vicinity of the Ms41-A gene.

iii) Genomic Clones and cDNAs of the Ms41-A Gene

Figure 2:
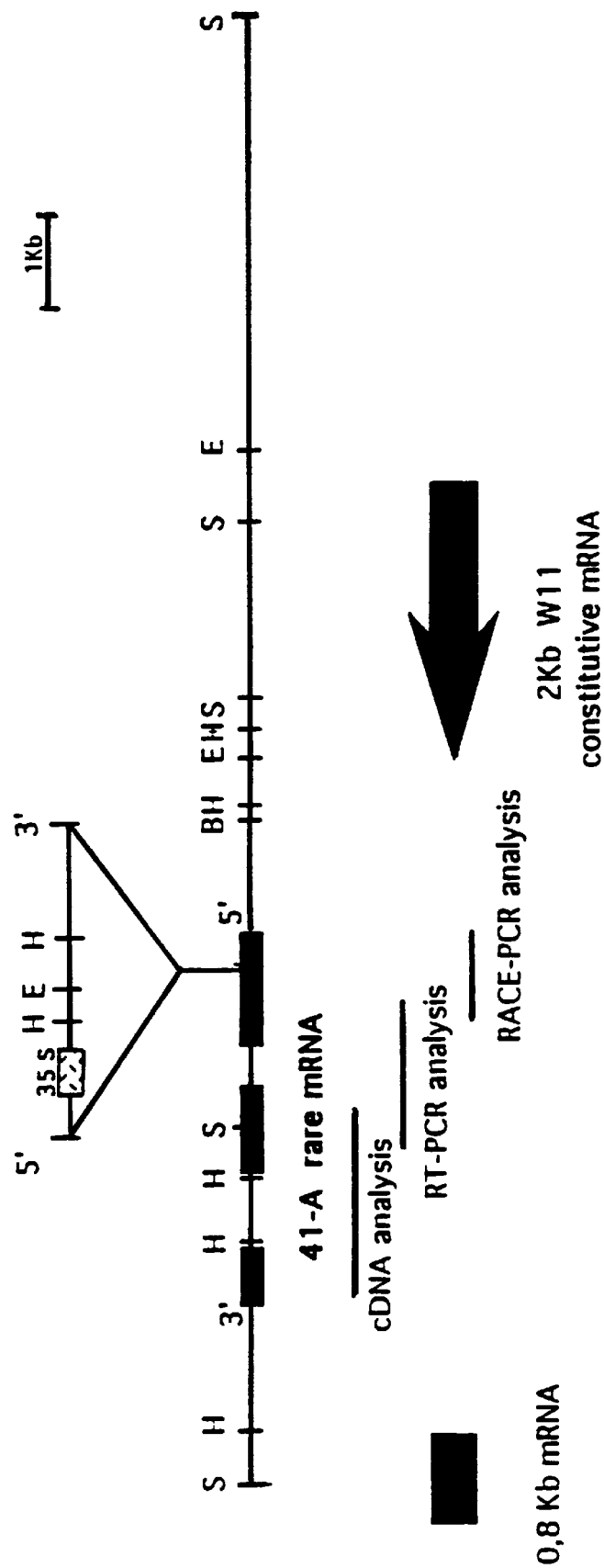
FIG. 2: shows a schematic diagram of the region containing the MS41-A locus cloned in lambda MSE3. The position of insertion of the 35S-Ac is indicated; B, BamHI; E, EcoRI; H, HindIII; S, SaeI.

Two different genomic libraries—one MboI partial library in EMBL 3A ( Clontech) and one HindIII partial in Lambda Dash II ( T. Pelissier, S.Tutois and G. Picard, unpublished) were screened with the 3' IPCR cloned product. Four different clones spanning the mutated region, were characterised by Southern analysis. One of them, lambda MSE3, which spans the transposon insertion site, was used for fine mapping. It contains the IPCR hybridising fragments detected on a genomic Southern (HindIII 3.3 kb, SspI 1.8 kb and PstI 4 kb). The entire plant DNA insert in MSE3 is contained on 4 SalI fragments; S1 (5 kb), S2 ( 4.9 kb), S3 (4.3 kb) and S4 (2.3 kb) (FIG. 2). The S3 fragment contains the plant DNA from the IPCR product.

After sequencing the IPCR product to determine the plant sequence 3' of the Ac element, more than 5000 bp of genomic sequence was obtained from MSE3 (3100 bp from the 5' Ac flanking region and 1900 bp at the 3'). The genomic sequence is presented in FIG. 3 and is indexed according to the putative transcription initiation site determined by 5' RACE (see below). One of the SalI sites of the fragment S3 is positioned at 2061 bp the other one is situated 5' upstream an EcoRI site (−1753 bp) and has not been sequenced. The transposon is inserted at position +318 bp.

To identify mRNAs expressed in the region of the transposon insertion site, three Arabidopsis cDNA libraries were probed with either the S1 or S3 fragments; a developing flower buds library (young buds) (Weigel et al., *Cell*, 69:843–859 (1992)), a library from flowers at late stages (after stage 10) (Hofte et al., *Plant Journal*, 4:1051–1061 (1993)) and an immature siliques library (Giraudat et al., *Plant Cell*, 4:1251–1261 (1992)).

Two classes of cDNAs were recovered with the S3 fragment as a probe and characterised.

a 1.9 kb cDNA (W11), isolated from the developing flower buds library. Its 3' end is located 1.5 kb upstream of the 3' 35S Ac end, suggesting that it is not linked to the Ms41-A phenotype. Sequencing of the extremities revealed that the EcoRI site (−1753 bp in FIG. 3) is present in the 3' part of this mRNA.

a 0.8 kb cDNA (G6), isolated from the immature siliques library but also present in the developing flower buds library. Comparison of G6 and genomic sequences shows that the transposon insertion site is 1440 bp upstream of the 5' end of the longest G6 cDNA (861 bp). In addition, the lack of a methionine codon in the 5' sequence of G6 indicated that this cDNA was not full-length. Further attempts at obtaining longer cDNAs from the three libraries were unsuccessful.

Another cDNA (A6) of approximately 1 Kb was isolated using the S1 fragment as a probe. It maps downstream of the G6 message.

Out of the 3 transcription units in the vicinity of the transposon insertion site, the best candidate for the Ms41-A mRNA was that corresponding to G6. To obtain a full-length G6 cDNA, primers were designed to the 5' end of the longest G6 cDNA and used in a 5' RACE reaction (5' AmpliFinder kit, Clontech). This proved unsuccessful, probably due to the 5' end of G6 lying far upstream of the longest cDNA obtained. Therefore primers were designed to regions of the genomic sequence that were upstream of the 5' end of the longest G6 cDNA. These, in combination with primers designed to the G6 cDNA, were used in RT-PCR reactions to define the extent of the G6 transcribed region. Results obtained suggested that the G6 message was at least 1 kb longer than the longest G6 cDNA obtained, and that the upstream sequence contained an intron of about 450 bp.

The G6 transcriptional start site was finally mapped by 5' RACE using primers Z3
(5'TTATCATCAACATCGCCATCGAATCTGCCG 3', (SEQ ID NO:5) positions 494–464 bp in FIG. 3);
and W1 (5'AAAGTAGTAAACCCTAGAG 3', (SEQ ID NO:6) positions 279–260 bp). RT-PCR was then used to recover a nearly full-length G6 message. Comparison of the G6 and genomic sequences shows that the first ATG is situated at position 157 bp; thus G6 putatively encodes a protein of 584 amino acids (FIG. 4). Over the region of overlap the cDNA and genomic DNA sequences were identical. This deduced protein has no significant homology to proteins of known function on the Genebank, EMBL and NBRF databases. The coding sequence consists of three exons, the first of which has been disrupted by the insertion of the 35 Ac element at amino acid position 54 in the Ms41-A mutant. This is strong evidence that G6 corresponds to Ms41-A. Final confirmation was obtained by analysis of phenotypes and DNA sequences around the Ac insertion site in Ms41-A progeny plants in which the 35S Ac element has excised.

To induce somatic exision of the 35S Ac element, plants were regenerated from liquid root cultures from single individuals derived from two different test-crosses. These crosses where between plants (A and B) that had only one Ac element but were still male sterile due to imprecise exision of the other Ac element, and male fertile plants that were heterozygous for Ms41-A: 35S Ac. This material was chosen because of the higher percentage of male sterile plants (40% instead of 20%, 50% instead of 25%?) than in a normal F2 population. Regenerants from clones representing male sterile plants were scored for male fertility. Numerous completely fertile plants were obtained from some individuals, however from 5 different regenerated plants from 4 different individuals, 7 different "revertant siliques" were obtained.

DNA from revertant plants or from progeny from "revertant siliques" was analysed by PCR for excision of the Ac element and PCR products cloned to determine the sequence left by the Ac element (footprint). The oligonucleotides presented in FIG. 5 were used:Ac 11 with W2 for the presence of the 3' junction, Ac 14 with G6 5'-11 for the 5' junction and W2 with G6 5'-11 or with Z3 for the excision allele(s). The PCR fragments derived from W2 with G6 5'-11 or with Z3 were cloned in the pGEM-T vector (Promega) and sequenced for all revertants. Previously junction products were sequenced confirming the presence of the typical target duplicated sequence of 8 base pairs:CTCCTCTC (positions 311 to 318 in FIG. 3).

The genotypes of 7 revertant plants or sectors were determined and are presented in FIG. 5. For all of them an allele restoring the open reading frame is observed which is the same as the wild type in 4 cases , a 3 bp insertion in 2 cases and a 6 bp insertion in one case. Footprints destroying the coding phase are observed in different revertants and also in the female parents (2 different 7 bp insertions and 2 different 5 bp insertion, and one with the addition of a 9 bp insertion which also introduces an in frame, TGA, stop codon). Their presence is always associated with segregation of male sterile individuals in the progeny. These results demonstrate that the Ms41-A protein has a determinant role in male fertility and that the Ms41-A gene has been tagged with the 35S Ac element.

iv) Ms41-A Genetic Mapping

Classical genetic mapping of Ms41-A with visual phenotypic markers has been described previously in section i) of this example. It places the Ms41-A locus near the bottom of chromosome 1. To determine if the Ms41-A mutation has been isolated previously in Arabidopsis the mutation was mapped more precisely using recombinant inbred lines made by Caroline Dean (Lister et al., Plant Journal, 4:745–750 (1993)). This method requires the identification of restriction enzyme fragment length polymorphisms (RFLPs) between the two parental lines (Columbia and Landsburg erecta) which are in, or near the Ms41-A locus. Polymorphisms were not found in Ms41-A or 5' of it, however the downstream cDNA, 6A, gives a HhaI polymorphism. Results, processed by MapMaker version 2, have positioned Ms41-A near the marker m532 (1.3 cM) and marker g17311 (4.6 cM). Those RFLP markers are situated on chromosome 1 close to the ADH locus, and map in the vicinity of glabrous 2 and apetala 1 on the integrated Arabidopsis genetic map (Hauge et al., Plant Journal, 3:745–754 (1993)).

Ms41-A is a new male-sterile mutant. It is not allelic to ms1 (Van der Veen and Wirtz, Euphytica, 17: 371-XXX (1968)) ms3, ms5, ms10, ms11 or ms12 (Chaudhury 1993). It is also different to the Ms2 gene (Aarts et al., supra).

v) Abundance of the Ms41-A Message

Ms41-A is expressed in 7 day old seedlings, in young floral buds and in immature siliques (cDNA libraries and RT-PCR data). The mRNA could not be detected in these tissues by Northern blotting using poly A+ mRNA which had been used successfully in RT-PCR analysis for the Ms41-A message. Thus the Ms41-A message appears to be of very low abundance; approximately 10 fold lower than another message required for male ferility in Arabidopsis, Ms2, in the same cDNA library (1 out of 12000 plaques for Ms2 (Aarts et al., supra) versus 1 out of 125000 for Ms41-A).

EXAMPLE 2

Isolation of the Ms41-A Promoter and Fusion to the β-Glucuronidase (GUS) Resorter Gene To attempt to determine the extent of utility of the Ms41-A promoter in male sterilty systems putative Ms41-A promoter fragments were linked to the reporter gene GUS and transformed into Arabidopsis and tobacco. This will reveal more precisely the spatial and temporal expression patterns of the Ms41-A gene and determine whether the low abundance of the Ms41-A transcript is due to weak expression or transcript instability.

Two promoter fragments, −903 (Hind III) to +79 (Short promoter) and −1753 (EcoR I) to +79 (Long promoter), have been fused to the GUS gene (transcriptional fusions) to produce the binary vectors pBIOS 176 and pBIOS 177 (FIG. 7).

These plasmids were constructed as follows:
The primers Y7 (positions −1799 to −1782 in FIG. 3) 5'CCTAACTTTCTTTGCGGC 3' (SEQ ID NO:7)
and W3 Xba (positions 84 to 59 in FIG. 3)
5' GATCTAGACCGTGATGTCTTAGAAGG 3' (SEQ ID NO:8)
were used in a PCR to recover a 1883 bp Ms41-A promoter fragment. This was cloned into the vector pGEM-T (Promega) forming p511. This plasmid was introduced into a dam, dcm minus E.coli strain (SCS 110) thus allowing the XbaI restriction enzyme to cleave the XbaI site. The 985 bp HindIII, XbaI fragment of p511 was cloned between the HindIII and XbaI sites of pBI121 (replacing the 35S CaMV promoter of this plasmid) forming plasmid pBIOS176. The 1853 bp EcoRI, XbaI fragment of p511 was cloned between the EcoRI and XbaI sites of pBIOS4 (a derivative of pBI121), replacing the 35S CaMV promoter of this plasmid, forming plasmid pBIOS177.

To construct pBIOS4, pBI121 was digested with EcoRI, the ends filled using Klenow polymerase and then religated forming pBIOS5. This plasmid was digested with HindIII, the ends filled using Klenow and an EcoRI sinker ligated into the destroyed HindIII site, forming pBIOS4.

pSIOS176 and pBIOS177 were transformed into Arabidopsis and tobacco. The larger promoter fragment is predicted to is contain the entire Ms41-A promoter region since the EcoRI site lies with the 3' end of the W11 transcript.
Arabidopsis Results:

a) Short promoter: Histochemical staining reveals that GUS activity is observed in most tissues and is especially high in callus, (strong blue staining is detectable after a few hours in X-GLUC (5-bromo-4-chloro-3-indolyl glucuronide).

b) Long promoter: GUS activity was seen in callus, but no obvious blue staining was observed in the vegetative parts of primary transformants. However 75% of the 40 transformants had significant GUS activity in anthers. In the floral buds observed, GUS expression is detected just after the breakdown of the callose wall (floral stage 10); expression appears to be located initially in the tapetum and subsequently in the microspores. GUS activity is still present in mature pollen. However it is possible that there is also GUS activity in the microsporocytes and tetrad microspores since the GUS substrate may not pentrate the thick callose wails surrounding the microsporocytes and tetrads.

Similar staining experiments were done with plants containing the 3 tapetum-specific promoter fusions—TA29 (Koltunow et al., *Plant Cell*, 2:1201–1224 (1990)), A6 (Hird et al., *Plant Journal*, 4:1023–1033 (1993)) and A9 (Paul et al., *Plant Molecular Biology*, 19:611–622 (1992)) and with the microspore/pollen promoter LAT 52 (Twell et al., *Molecular and General Genetics*, 217:240–245 (1989)).

A9 is definitely the earliest and with the A6 promoter, GUS is expressed when tetrads are visible; by contrast the TA 29 promoter gives expression at roughly at the same time as Ms41-A; the latter also shows earlier expression in microspores than LAT 52. In seedlings of 5 out of 7 transformed plants, very low levels of GUS expression is detected in aerial parts.
Tobacco Results:

a) Short promoter: GUS expression appears to be constitutive.

b) Long promoter: Results were similar to those observed in Arabidopsis, ie expression is largly confined to the tapetum, microspores and pollen of the anther. Very low GUS expression was seen in the aerial parts of seedlings, however no expression was detected in callus.

It appears that expression from the long promoter matches that of the Ms41-A gene, with very low level "constitutive" expression. Expression in the anther is much stronger than predicted by the abundance of Ms41-A transcript in floral parts indicating that the Ms41-A message may be very unstable. Higher level constitutive expression observed from the short promoter suggests that there a constitutive silencer is present in the upstream region of the promoter between posititions −1635 to −900 bp. The conserved pattern of expression of the long promoter between tobacco and Arabidopsis suggests that the long promoter will be useful in male sterility systems in a wide range of plant species. Examples 3 and 4 below demonstrate the use of the long Ms41-A promoter in male sterility systems.

EXAMPLE 3

Expression of Barnase from the Ms41-A Promoter in Tobacco and Maize

The timing of expression of the Ms41-A promoter in the tapetum is similar to that seen from the tobacco TA29 promoter, thus fusion to cytotoxins such as Dipthera toxin A (Thorsness et al., *Developmental Biology*, 143: 173–184 (1991)) and Barnase (Mariani et al., *Nature*, 347: 737–741 (1990)) will ablate the anther tapetum leading to complete male sterility. Thus the long Ms41-A promoter is linked to Barnase. A 1 kb XbaI, HindIII (filled) fragment encoding Barnase is excised from pWP127 (Paul et al., supra) and cloned between the XbaI and SstI (filled) sites of pBIOS177 forming pBIOS 177-Barnase (FIG. 7).

This plasmid is used to regenerate tobacco and Maize transformants that are male sterile. Although the weak "consitutive" expression of the Ms41-A promoter should prevent recovery of such plants, it is likely that these plants have reduced Ms41-A promoter expression. Thus no significant expression of Barnase occurs in vegetative tissues whereas expression is sufficient to cause tapetal cell death and male sterility.

EXAMPLE 4

Expression of Antisense Ms41-A from the Ms41-A Promoter in Arabidoysis

The Ms41-A promoter can be used to downregulate the expression of genes essential for tapetal function thus causing complete male sterility. Downregulation can be achieved by expression from the Ms41-A promoter of antisense or sense fragments of the target gene or by expression of ribozymes which will cleave the target gene transcript. Such a target gene is Ms41-A. To construct an Ms41-A promoter-Ms41-A antisense chimeric gene, RT-PCR is used to generate a 1923 bp Ms41-A fragment from young Arabidopsis floral buds mRNA. The primers used are:

W3 Bam, 5' CGGATCCTTCTAAGACATCACG 3' (SEQ ID NO:9) (positions 54–75, FIG. 3) and 3'2, 5' AATG-TACTACTACTACTACTTAGGAC 3' (SEQ ID NO:10) (positions 3001–2976, FIG. 3).

Figure 8:
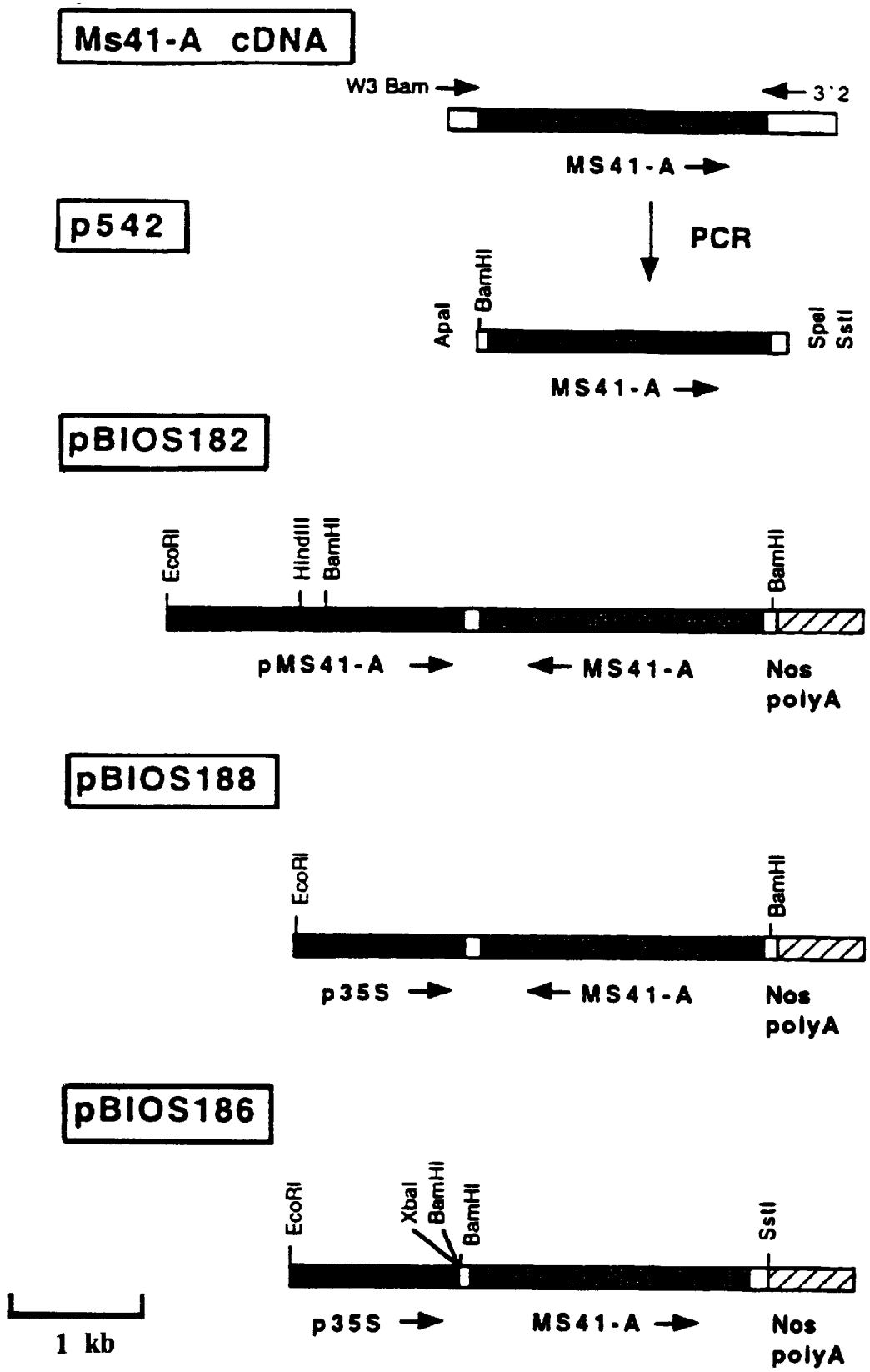
FIG. 8: shows a diagram of the MS41-A promoter-antisense MS41-A and CaMV 35S promoter-antisense and sense MS41-A chimeric genes.

This PCR fragment is cloned into pGEM-T forming p542, such that the 5' end of MS41-A is adjacent to the ApaI site of pGEM-T (FIG. 7). The MS41-A SpeI, ApaI (filled using T4 DNA polymerase) fragment is cloned between the XbaI and SstI (filled) sites of pBIOS177, thus replacing the GUS gene of pBIOS177 and forming pBIOS182 (FIG. 8). This plasmid is used to transform Arabidopsis. A proportion of transformants are male sterile with a phenotype that resembled that of the original Ms41-A mutant. Examples 5 and 7 below describe the use of the Ms41-A transcribed region in male sterility systems.

EXAMPLE 5

Expression of a 35S CAMV Promoter- Ms41-A Antisense Chimeric Gene and a 35S CaMV Promoter Ms41-A Sense Chimeric Gene in Arabidopsis As described in Example 4, downregulation of the Ms41-A gene by expression of Ms41-A antisense fragments, sense fragments or ribozymes, each driven from the Ms41-A promoter will lead to male sterility. However any promoter that has the appropriate pattern of expression, ie is active in microsporocyte and/or tapetal cells of the anther at the time of Ms41-A expression, may be used to downregulate Ms41-A and cause male sterility. Thus a CaMV 35S promoter is linked to an antisense Ms41-A fragment and to a sense Ms41-A fragment. The antisense construct is obtained by cloning the ApaI (filled), SpeI p542 MS41-A fragment between the XbaI and SstI (filled) sites of pBIOS4 forming pBIOS188 (FIG. 8).

The sense construct is obtained by cloning the ApaI (filled), SstI p542 MS41-A fragment between the SmaI and SstI sites of pBIOS4 forming pBIOS186 (FIG. 8). These plasmids are transformed into Arabidopisis. A proportion of the antisense and sense transformants are male sterile with a phenotype similar to that of the original Ms41-A mutant plant.

EXAMPLE 6

Isolation of a Ms41-A Orthologue from Maize

Most methods to use the coding region of the Ms41-A in a male sterilty system require the isolation of the orthologous sequence either from the crop species of interest or from a close evolutionary relative. Such methods include antisense and sense supression and the use of ribozymes. The degree of evolutionary conservation between orthologous protein sequences is variable and is probably dependant on constraints on protein function. Athough orthologous protein sequences may be highly conserved, codon usage may be quite different, producing orthologous mRNA sequences that may have low homology. Thus, in order co downregulate the Maize version of Ms41-A, it is probably necessary to isolate the Maize version of Ms41-A. Given the Arabidiopsis Ms41-A mRNA sequence, several approaches are possible for the isolation of the Maize orthologue. Some of which are outlined below:

The Ms41-A cDNA can be used as a probe on a Maize Northern or Southern at low stringency to see if a mRNA or genomic band hybridises. This was unsuccessful indicating that these sequences are widely diverged. The Arabidopsis sequence can be used as a probe in more closely related species and the orthologues in turn used as further probes until the version in Maize is identified. The cloning and sequencing of such orthologues may also result in the identification of conserved areas that can be used in a degenerate PCR approach.

Antibodies to Ms41-A may also be useful since protein sequences and epitopes are generally more conserved than RNA/DNA sequences.

The approach used was to screen the Genebank and EST (Expressed Sequence Tag) databases for sequences that showed homology to the Arabidopsis Ms41-A DNA sequence. Four groups of sequences were identified according to the degree of sequence similarity. Alignments of these sequences are presented in FIG. 9.

Group 1

This group contains the Arabidopsis Ms41-A cDNA and an EST sequence from rice OSS2204 (D40316) which was cloned from a shoot cDNA library (prepared from etiolated 8 day old seedlings).

Group 2

In this group are two pairs of almost identical Arabidopsis EST sequences (ATTS3975 (Z37232) and T43470) and (T21748 and R30405) which are presumably derived from the same transcripts and can be considered as two sequences. The R30405, T21748 and T43470 cDNAs were isolated from a library prepared using a mixture of RNA from various tissues. The ATTS3975 cDNA is from a library prepared from cell suspension culture. In addition, in this group is a rice cDNA isolated from a root cDNA library (seedling stage) OSR1187 (D24087).

Group 3

In this group are 3 EST sequences and 1 cDNA sequence ATTS1074 (isolated from a cycling cells cDNA library). A partial EST sequence for ATTS 1074 is on the database (Z25611) and after identification of this sequence as similar to Ms-41A the cDNA clone was obtained and the sequence completed. The other 3 sequences are all identical or almost identical to the ATTS1074 sequence.

The cDNA clones R65265 and T44526 were isolated from a mixed RNA library. ATTS2424 is a 3' sequence EST sequence from the same cDNA clone as ATTS1074, this clone (TAI231) was isolated from a cDNA library prepared from a cell suspension culture containing cycling cells.

Group 4

This group contains sequences of 4 closely related plant transcription factors; Viviparous-1 from maize (McCarty et al., *Cell*, 66:895–905 (1991)) and rice (Hattori et al., *Plant Molecular Biology*, 24:805–810 (1994)), ABI 3 from Arabidopsis (Giraudat et al., *Plant Cell*, 4:1251–1261 (1992)) and a *Phaseolus vulgaris* embryo-specific acidic transcriptional activator PvAlf (Bobb er al., *Plant Journal* In press (1995)).

There is some amino-acid similarity between a region in the N-terminal of the Ms41-A protein and the proposed DNA binding domain of maize Viviparous-1. This region is highly conserved between the 4 transcription factors (>80% amino-acid identity between all 4 sequences). This suggests that the Ms-41A protein may have DNA binding activity, although the MS41-A protein might be sorted via the ER, perhaps to be secreted, since Ms41-A has a putative signal peptide and 6 putative N glycosylation sites.

The most closely related sequence to Ms41-A identified by this analysis is the rice OSS2204 sequence. This was obtained from the rice sequencing project and used to probe a Maize cDNA library made in Lambda UniZap (Stratagene) from polyA+ RNA. isolated from pre-meiotic to meiotic-stage male inflorescences. The cDNA isolated, Zm41-A, is approximately 2.2 kb in length and has a poly A tail at it's 3' end. Approximately 300 bp of 5' prime sequence is shown in FIG. 10.

This sequence shows strong similarity to the rice OSS2204 cDNA sequence (84% identity) but is only 53% identical to the Arabidopsis sequence. The ORF indicated underneath the DNA sequence is similar to both the proposed OSS2204 ORF (89% identical, 94% similar) and the Arabidopsis Ms41-A protein sequence (54% identical, 65% similar).

Figure 11:
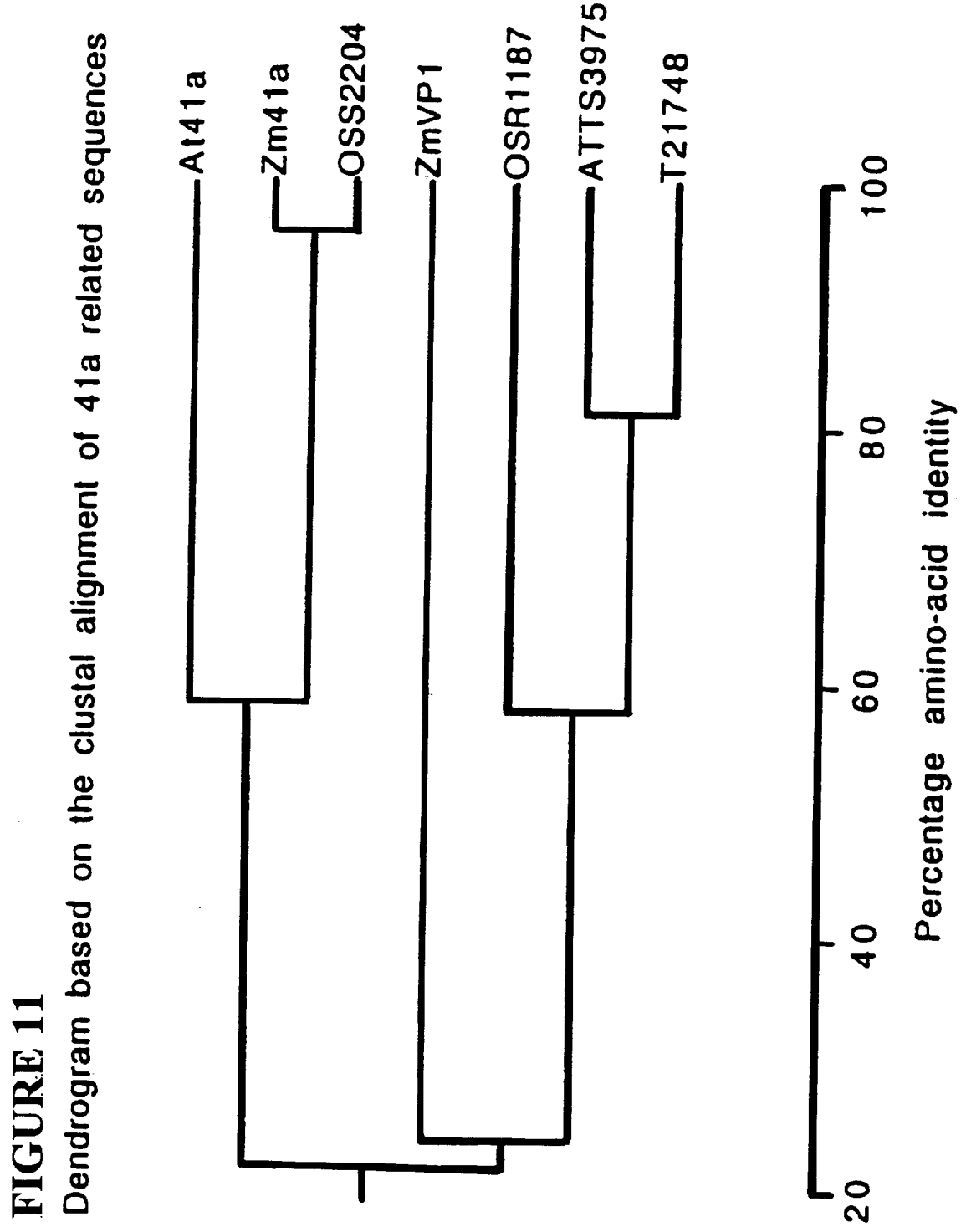
FIG. 11: shows a dendrogram of MS41-A related sequences.

A dendrogram of the Ms41-A related sequences indicates that the Zm41-A sequence falls into group 1 (FIG. 11). This indicates that this cDNA is a good candidate for the maize orthologue of the Arabidopsis MS41A gene.

EXAMPLE 7

Expression of an Actin Promoter- Zm41-A Antisense Chimeric Gene in Maize

The Zm41-A cDNA is linked in an antisense orientation to a rice actin promoter. The entire Zm41-A cDNA is excised from pBluescript SK– (Stratagene) as an XhoI (filled), PstI fragment and cloned into PstI, SmaI-cut pCOR113 (McElroy et al., *Molecular and General Genetics*, 231: 150–160). This plasmid is used to transform Maize by a particle bombardment technique. A proportion of the transformants are male-sterile with a phenotype similar to that of the Arabidopsis Ms41-A mutant. This suggests that the Zm41-A sequence is the functional orthologue of Ms41-A and indicates that any sequence that falls within group 1 (FIG. 11) is likely to encode a functional orthologue of Ms41-A.

EXAMPLE 8

Molecular Characterisation of Zm41-A Gene(s)

a) Zm41-A Gene Transcription

BY RT-PCR this transcript has been shown to be abundant in anther RNA; in leaf and tassel RNA populations it is detected at a lower level.

After comparison of the maize and Arabidopsis sequences it was thought that the cDNA was unlikely to be a full length clone. With the "Marathon cDNA amplification" kit (Clontech, Palo Alto, Calif., USA) 5'RACE experiments were conducted on mRNA extracted from maize anthers at the meiosis stage, which yielded additional 5' sequence. Two types of 5'RACE products were obtained and sequenced, the first contained approximately 150 bp of additional 5' sequence as well as a 108 bp insertion at position 244 in the cDNA. The second RACE product contained approximately 130 bp of additional 5' sequence. It is believed that the first RACE product may be the result of differential or incomplete splicing of the transcript resulting in a 36 amino acid insertion in the predicted peptide sequence as well as the 52 additional amino acids at the N terminal of the protein. Even with these additional sequences the full length transcript is likely to be longer at the 5' end, based on comparison with the Arabidopsis protein and the maize genomic sequence.

b) Isolation of and Characterisation of Maize Genes which are Orthologs to Ms41-A The Zm41-A cDNA was used to screen two different maize genomic lambda libraries. The first was a commercial library (Clontech, Palo Alto, Calif., USA) elaborated with DNA fragments from maize line 373 plantlets. DNA was partially digested with MboI enzyme and the fragments were cloned into the BamHI site of EMBL-3 (Frischauf et al, *J.Mol.Biol.*, 170:827 (1983)). The insert DNA can be excised from the clone by the enzyme SalI. The second was a lambda library kindly provided by R. Mache (Universite Joseph Fourrier, URA 1178, Grenoble, France) elaborated with DNA fragments from the Mo 17 maize line. DNA was partially digested with the enzyme MboI and the fragments were cloned into the BamHI site of EMBL-4 (Frischaul et al, supra). The insert DNA was excised by the enzyme EcoRI. The genomic libraries screening was performed following the instructions of Sambrook et al (Molecular cloning: a laboratory manual, cold Spring Harbour Laboratory Press, New York, 1989). $10^6$ recombinant Lambda per library were screened and three rounds of screening were performed. Fourteea positive lambda clones were isolated one of which was obtained from the library provided by R. Mache.

DNA from positive lambda clones was extracted and purified using Qiagen columns (Chatsworth, Calif., USA) according to the manufacturer's instructions. Then the clones were characterised by Southern analysis (*J.Mol.Biol.*, 98:503–517 (1975)) in order to establish classes. DNAs from the Clontech library were restricted with HindIII and EcoRI and double restricted with HindIII/SalI. DNAs from the Mache library were restricted with HindIII and EcoRI and double restricted with HindIII/EcoRI. DNA fragments were separated on agarose gel, denatured and blotted onto Hybond N+ membrane (Amersham, Buckinghamshire, UK). The blots were hybridised with $^{32}$P-labelled Zm41-A cDNA isolated after digestion with BamHI and XhoI (the resulting fragment is 2.1 kb long).

Ten lambda clones were different and were distributed in three classes:

class A comprising 5 clones (Z9, Z23, Z27, Z35 and Z36);
class B comprising 4 clones (Z7, Z28, Z29 and Z33); and
class c with only one clone, Z31, isolated from the R. Mache library.

In order to study the sequence of these three classes, the sub-cloning of three different genomic phages (Z31, Z33 and Z35) in the plasmid pBSII SK+ (Stratagene, Lajolla, Calif., USA) was performed according to the classical cloning method (Sambrook et al, supra). Hybridizing fragments were firstly slected. After the sequencing of the fragments' extremities with universal primers, oligonucleotides were designed and the sequencing was chieved using the walking primer method.

Figure 13:
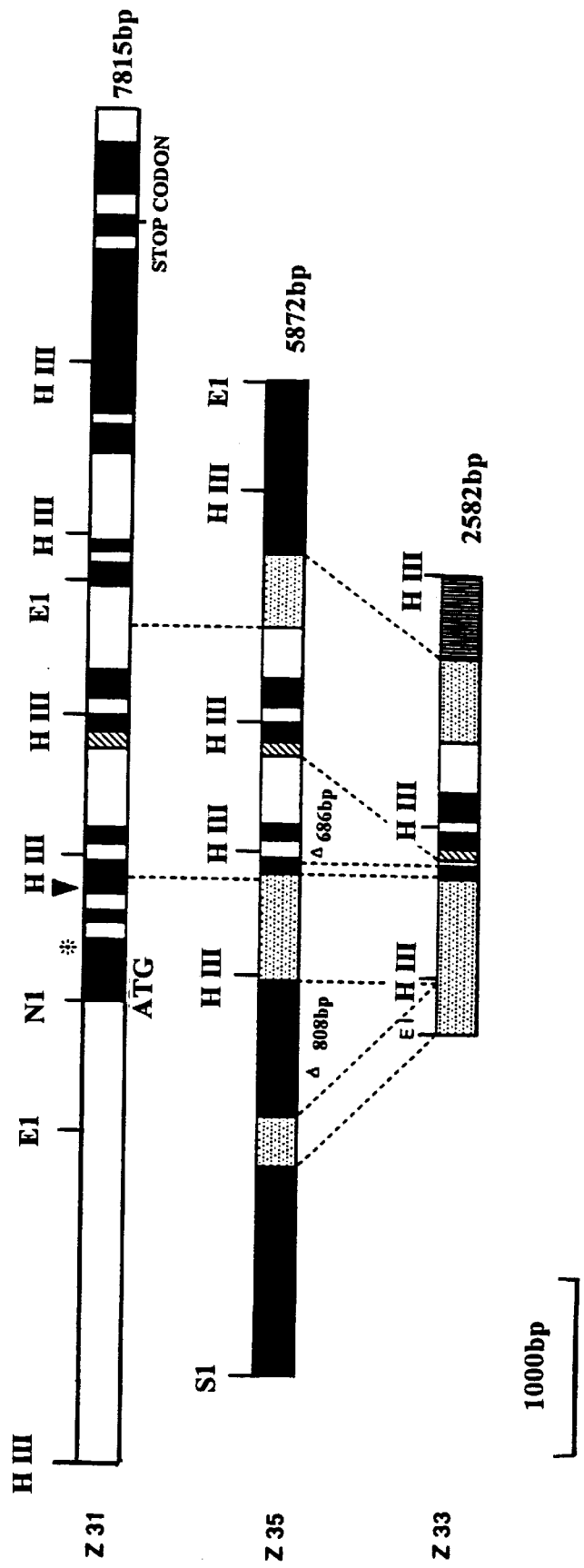
FIG. 13: snows restriction maps of Z31, Z33 and Z35 genomic clones isolated with cDNA of Zm41-A. EI, HIII, NI and SI indicate restriction sites of endonucleases EcoRI, HindIII, NcoI and SalI, respectively. * indicates the start of the longest RACE product. ▼ indicates the start of Zm41-A cDNA. Dotted lines indicate homologous regions and Δ indicates deletions.

With the clone Z31, 7.8 kb of continuous sequence data were obtained (see FIG. 12). To determine the complete gene structure, we have sequenced the entire Zm41-A cDNA. This is 2109 bp in length and encodes a putative peptide of 587 amino acids. The comparison between the genomic sequence and the cDNA and 5'RACE sequences indicated that this gene contains at least 12 exons. The insertion reported in the longest RACE products corresponds to the end of intron 4. Thus, the two families of cDNAs might be explained by the presence of two splicing sites in this intron. In the genomic sequence upstream of the end of the RACE products, there was detected the continuation of the open reading frame of 270 bp before an initiation codon at a NcoI restriction site. AAsuming that this initiation site is the right one, the length of the fragment which might contain the promoter sequence was 2.7 kb from the HindIII site where the sequence starts to the NcoI site. Therefore the translation of the Zm41-A Z31 gene should give a putative protein of 736 amino acids. The Z31 gene structure is depicted in FIG. 13.

With the addition of the unspliced sequence (homologous to the end of intron 4) a longer protein might be obtained. Indeed, the longest open reading frame deduced from the genomic sequence Z31 including this insertion sequence exhibits two stop codons in frame. It is also worthwhile noting that there is a clear polymorphism here since the RACE products do not show these stop codons. The missplicing phenomenon may be a regulatory mechanism for the expression of the the Zm41-A related proteins as has recently been demonstrated in maize for another gene (Burr et al, *The Plant Cell*, 8:1249–1259 (1996)). Therefore, either this gene codes for two proteins (736 aa and 131 aa) or it codes for the 736 aa and 772 aa proteins.

Moreover, a slight difference was observed between the Zm41-A cDNA and the Z31 genomic sequence in exon ten where a small addition is present (15 bp replaced by 36 bp); this is also in agreement with genetic polymorphism between maize lines. The maize lines used to study the mRNA and the genomic sequence are divergent (A188, B73 and Mo17 respectively). In FIG. 14 there is provided the alignment of the Z31 protein (736 aa) deduced from the longest open reading frame, with the protein deduced from the Zm41-A cDNA (587 aa). We found 15 amino acid changes as well as an additional 7 amino acids for the Z31 protein, these additional amino acids being located at position 556 of the Zm41-A cDNA protein.

For the other two genes, Z33 and Z35, 2.9 Kb and 5.8 Kb were respectively sequenced (see FIGS. 15 and 16). Z35 contains exon 3 in part and the complete exons 4, 5 and 6 from the Zm41-A cDNA. Z33 is similar to Z35 but it has a deletion of exon 4 and the 3' end of exon 3 the two have the insertion sequence found in the longest 5' RACE products. In addition, the comparison of the Z33 and Z35 sequences indicates at two deletions in the Z33 gene with respect to the Z35 gene. The first one is 686 bp long and starts in the 3' end of exon 3 and extends to the end of exon 4 (with reference to the Z31 gene structure). The latter is located upstream of the sequence homologous to Z31 and the Zm41-A cDNA and is 808 bp long (see FIG. 13). Moreover, these two genes differed in their 3' sequenced regions.

Due to the high level of conservation between these 3 sequences it is possible that the Z35 gene derived from Z31 via genetic rearrangements, deletions and/or insertions. Z33 has subsequent deletions from Z35.

EXAMPLE 9

Genetic Mapping of Zm41-A loci 58 single seed descent (SSD) maize lines derived from the cross A188xHD7 (Murigneux et al, *Theor.Appl.Genet.*, 87:278–287 (1993)) were used for genetic mapping by RFLP technology. Hybridisation was performed with radio-labelled Zm41-A cDNA (BamHI-XhoI fragment, 2.1 Kb) on blots containing DNA from SSD lines and parental lines, digested with HindIII or EcoRI. Linkage analysis with the other RFLP markers mapped on this population was done using the Mapmaker version 2.0 computer program for Macintosh (Lander et al, *Genomics*, 1:174–181 (1987)) and map distances were calculated with Kosambi function.

Many polymorphic bands between parental lines were revealed: one or two major bands and a few faint bands. Three loci, named Zm41-A.A, Zm41-A.B and Zm41-A.C were found located on two different chromosomes. Zm41-A.A locus corresponding to major bands, was located on the long arm of chromosome 6 at 26 cM from the RFLP marker umc132 and at 2 cM from the rflp marker umc62 (Maize Genetics Cooperation Newsletters (MNL) (August 1995) 69:248). Zm41-A.B and Zm41-A.C loci, corresponding to faint bands were located on chromosome 2 and were separated from each other by 19 cM. The Zm41-A.B locus lies near the centomere between umc131 (6 cM) and umc055 (3 cM) markers (MNL, supra). The Zm41-A.C locus was on the longchromosomic arm between umc055 (16 cM) and umc022 (6 cM) (MNL, supra). According to the mutant maize genetic map, no obvious male sterile mutant is mapped in those regions. One dominant male sterile mutant, Ms21, discovered in 1950 has been assigned on chromosome 6 but not very precisely. This mutation gives sterility only in the presence of the sks1 mutation. Interestingly, this mutation maps on chromosome 2, in the vicinity of the Zm41-A.B. Hybridisation on the blots containing DNA from SSD lines, with a Z31 gene specific probe, demonstrated that the Z31 gene corresponds to the Zm41-A.A locus on chromosome 6.

What is claimed is:

1. An isolated nucleic acid molecule which comprises nucleotides having a sequence which:
   a) encodes a Ms41-A protein from Arabidopsis;
   b) encodes the Z31 protein (SEQ ID NO:29) or the Zm1-A protein (SEQ ID NO:30) of FIG. 14;
   c) comprises the sequence of FIG. 15 (SEQ ID NO:31);
   d) comprises the sequence of FIG. 16 (SEQ ID NO:32);
   e) comprises the sequence of FIG. 12 (SEQ ID NO:28), or a sequence which codes for the same amino acid sequence as the sequence of FIG. 12;
   f) hybridizes under highly stringent conditions to the nucleic acid of a), b), c), or d), with the proviso that the hybridizing sequence is not the EST sequence from rice having Genbank Accession No. D40316; or
   g) hybridizes under highly stringent conditions to the coding region of the nucleic acid sequence of FIG. 12, with the proviso that the hybridizing sequence is not the EST sequence from rice having Genbank Accession No. D40316.

2. The nucleic acid molecule of claim 1 a), wherein the nucleic acid molecule encodes a protein having an amino acid sequence as shown in FIG. 4 (SEQ ID NO:12).

3. The nucleic acid molecule of claim 1 having the sequence shown in FIG. 12 (SEQ ID NO:28), FIG. 15 (SEQ ID NO:31), or FIG. 16 (SEQ ID NO:32), or the coding regions thereof.

4. The nucleic acid molecule of claim 1 derived from the family Brassicaceae or Maize.

5. The nucleic acid molecule of claim 1 which further comprises a promoter, a coding region and a transcription termination region.

6. The nucleic acid molecule of claim 5 having at least twenty (20) consecutive nucleotides of the nucleotide sequence shown in FIG. 3 (SEQ ID NO:11).

7. The nucleic acid molecule of claim 6 having a portion of the nucleotide sequence shown in FIG. 3 (SEQ ID NO:11) commencing with the nucleotide labeled 1.

8. The nucleic acid molecule of claim 1 further comprising a promoter sequence which drives expression in a plant tissue involved in the control of fertility.

9. The nucleic acid molecule of claim 8 wherein the promoter is a tapetum-specific promoter.

10. The nucleic acid molecule of claim 9 wherein the promoter is the A3, A6 or A9 promoter derived from Brassicaceae.

11. The nucleic acid molecule of claim 1 further comprising a 3'-transcription regulation signal.

12. A vector comprising the nucleic acid molecule of claim 1.

13. A host cell transformed with the nucleic acid molecule of claim 1.

14. A process for preparing the nucleic acid molecule of claim 1, the process comprising coupling together successive nucleotides, and/or ligating oligo- and/or polynucleotides.

15. A plant cell transformed with the nucleic acid molecule of claim 1 or comprising the vector of claim 12.

16. A whole plant, or part of a plant, comprising the plant cell of claim 15.

17. A method for the production of a transgenic plant which comprises the step of transforming plant propagating material with the nucleic acid molecule of claim 1.

18. The nucleic acid molecule of claim 8, wherein the promoter is a Ms41-A promoter.

19. The nucleic acid molecule of claim 8, wherein the promoter drives expression in the anthers.

20. The nucleic acid molecule of claim 1 comprising nucleotides having a sequence that encodes a protein having an amino acid sequence as shown in FIG. 4 (SEQ ID NO:12), or nucleotides having a sequence that hybridize thereto under stringent conditions.

21. The nucleic acid molecule of claim 1 comprising nucleotides having 1) the sequence shown in FIG. 12 (SEQ ID NO:28), FIG. 15 (SEQ ID NO:31) or FIG. 16 (SEQ ID NO:32); 2) a sequence corresponding to the coding regions thereof; or 3) a sequence which hybridizes under highly stringent conditions to the coding regions thereof.

22. A plant cell comprising a transposon in a gene thereby inactivating the gene, wherein the gene comprises nucleotides having the sequence shown in FIG. 3 (SEQ ID NO:11), FIG. 12 (SEQ ID NO:28), FIG. 15 (SEQ ID NO:31), or FIG. 16 (SEQ ID NO:32); or a coding sequence which hybridizes under highly stringent conditions to the sequence shown in FIG. 3 (SEQ ID NO:11), FIG. 15 (SEQ ID NO:31) or FIG. 16 (SEQ ID NO:32); or a sequence which hybridizes under highly stringent conditions to the coding region of the sequence shown in FIG. 12 (SEQ ID NO:28).

23. The plant cell of claim 22, wherein the transposon is an Ac element.

24. A plant comprising the plant cell of claim 22.

* * * * *

SEQUENCE LISTING (1) GENERAL INFORMATION:

(iii) NUMBER OF SEQUENCES: 32

(2) INFORMATION FOR SEQ ID NO: 1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

AAGGATCCTG GCAAAGACAT AAATC                                      25

(2) INFORMATION FOR SEQ ID NO: 2:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 2:

AGATGCTGCT ACCCAATCTT TTGTGC                                    26

(2) INFORMATION FOR SEQ ID NO: 3:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 3:

CGTATCGGTT TTCGATTACC GTATT                                      25

(2) INFORMATION FOR SEQ ID NO: 4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

AGATGCTGCT ACCCAATCTT TTGTGC                                     26

(2) INFORMATION FOR SEQ ID NO: 5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

TTATCATCAA CATCGCCATC GAATCTGCCG                                 30

(2) INFORMATION FOR SEQ ID NO: 6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

AAAGTAGTAA ACCCTAGAG                                             19

(2) INFORMATION FOR SEQ ID NO: 7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

CCTAACTTTC TTTGCGGC                                              18

(2) INFORMATION FOR SEQ ID NO: 8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

GATCTAGACC GTGATGTCTT AGAAGG                                     26

(2) INFORMATION FOR SEQ ID NO: 9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

| CGGATCCTTC TAAGACATCA CG | 22 |

(2) INFORMATION FOR SEQ ID NO: 10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

| AATGTACTAC TACTACTACT TAGGAC | 26 |

(2) INFORMATION FOR SEQ ID NO: 11:

(i) SEQUENCE CHARACTERISTICS:
        (A) LENGTH: 5336 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION:1957..3018

(ix) FEATURE:
        (A) NAME/KEY: CDS
        (B) LOCATION:3487..4173

(ix) FEATURE:
        (A) NAME/KEY: CDS
        (B) LOCATION:4736..4741

(ix) FEATURE:
        (A) NAME/KEY: intron
        (B) LOCATION:3019..3486

(ix) FEATURE:
        (A) NAME/KEY: intron
        (B) LOCATION:4174..4735

(xi) SEQUENCE DESCRIPTION: SEQ ID NO: 11:

| TCCTAACTTT CTTTGCGGCA TTTCTTATAA TACTTCGTCA GTTTTCAGAA TTCTTAAATC | 60 |
| TTTTTGCTGT GTTCTTATAA AGAAACATCA TCTATTAAAG TTGTCTTCGT TTGGATTTGG | 120 |
| TTTTGATGAC TTTGGGAAAT ATTTATGTTT AAGAAGGTTT CATTGGTCAT TGACTTTTAT | 180 |
| ATATTATATC GTAACCATGA TGTGATAGTG GGCCTTAGAT CAACAAACAT GCGAAAAACA | 240 |
| GAAGCAGAGG CCCGTTTCAA CGGAGCATAA TAAATTGCAT TCTCTGTCTT TTGTTTTTAG | 300 |
| GTTTTTTTTT TAACTGATAG ATGTGCCGTC GAAATAATA TTGATATTTA AAAATTCACA | 360 |
| ACAAACATTC TTAACTGACC CACCCATCTA TCTGCTATTC CCACGCGCCA AGGAAAATAA | 420 |
| TAATAATAGC GAAATTGATT TTACATTTAT TTATTGATAG ATAATTTGTG TATTGTTAAG | 480 |

```
ATTAACAGAT TTTAAGGGAT TAAAGTGGAA AAGGTAAACC GAAGACAACT TGCCATTTAC     540

TGATTTACAA CAATCCAAAT TTAAAAACAA ATGGTCCCAG TTTTTAGGGT TGTCACTTAA     600

ATTTATCGAA ATATTTACAC TTTAATTGGG TAAAACATAA TGGACAGAAA AACAAATATT     660

GTGACAAACA AAAAAACATG TTTTCACCAA GAAAAACAAA AACAAAAAAG ATGTAAAGCT     720

TTTCTTACAT CTGTACAAAA TAAAAGCAGA CGAAATTGTA CTTTATTTTC CTTATTAAAT     780

TGTCGGTATG TTTTATATGT TGTGAAAAGT AGAATGGATA ACCAAATAAA AATTACTGCA     840

TCTTAATAAA GTTGGTTCAA CCGGTTTAAA ATGTATTTTT TTAGTGTTAA CAACTTAAAG     900

CTTTTTTCGA TTATCGAATT GCAACAAACA AATATATTAA CAGAAAAAAG GAATCATGTA     960

TCTATTTCAA TATCCTGTTT TTTTTCTTCC ATTTGGATAT TTAGATCTTT TTCTGAATTT    1020

ATCTTGTTCT TAAATTAAAA CAGAAAAAAA GATTAAAAGT AAGACAGCTT GCTAATGGCA    1080

ACCGCAACAA ACAAGATAAT TTTGAAACGG ATCCACTTGG ATTTTCTTTG ATTTGTAGA     1140

AAAATTGACA AATTGCTTTT GTATAAAAAC AAAAAATGTA CCGTAAAAAC ACACACATAA    1200

AAAATAAAAA GTGATAATGA CAAACAAATA AAGAGGTATT TTTCTTTTAT CTACTAATGT    1260

GATTATAAAA AAATCGACAT TGAAAATTTC AACACATCTT TTTCGCCAAA ACCTGAAAAT    1320

GGTCTTATTA AACATAAAAT TAGTTTTTTT GTCTTTCTAT TATATATTCA ATAACTCATC    1380

CCAACTTGAA CAAACCTATA AGTTCCGTAG TGTTCTTTTC TGTTGTGACA AAAAATACTA    1440

GCTAACGAGG GATAAGCACA AAAACATGAT TAATGTTTCT CTAATCATTC TAAAAATCTA    1500

CAGGAATATT CCCTTTTCAG TTTTTTCTTT CTTAAATGCA TTTCTTAGTT CTTCATAATT    1560

CAGTGAGTTT TAATAACAAT AATAAAAAAA AGAGCATCAT TAATTGAACC TAAAAATAAT    1620

GGGAAGAAAA ACCAAAAAGA TAGAGAGTAA GATGCACGCG CTAAAGATCG AACGGTTAAT    1680

AGAATCAGGT TAGTGAAGAG AGATATTAAA AGTTTGTTGT CGTGTGGCAA AAACTATAAT    1740

TTCCTTCACA CAAACAAAAA AAATAAAATC AAACACAAAA TCCCGTAGCA TCGTAACAGT    1800

AATTCGCTAT TATCTCCTCA CCCTCCGCTT TCGCTTCCCT TCTCTGCCCG TTTCAATTCC    1860

TTCTAAGACA TCACGGTCTC TCTCTATAAA AACAGTACCT ACCTCTTCTT CTTCTTCTTC    1920

ATTCGCTGAC TTCGTTTACA CTGAAAACAA ATACCTATGT CACCGCCGTC GGCAACCGCC    1980

GGTGACATCA ACCACCGTGA AGTAGACCCG ACGATCGGC GCGCTTGTGC TGGAGCCTCC     2040

GTCCAGATCC CTGTCCTTCA CTCTAGGGTT TACTACTTTC CACAAGGTCA CGTTGAGCAC    2100

TGTTGCCCTC TCCTCTCTAC TCTTCCTTCC TCCACCTCGC CGGTTCCATG TATCATCACT    2160

TCAATCCAGT TGCTCGCCGA TCCGGTTACC GACGAGGTCT TGCTCACCT TATTCTTCAA     2220

CCGATCACGC AGCAGCAGTT TACTCCGACT AATTATTCAC GATTCGGCAG ATTCGATGGC    2280

GATGTTGATG ATAACAACAA GGTGACTACC TTCGCCAAAA TTCTCACGCC TTCTGATGCT    2340

AACAATGGAG GTGGCTTCTC CGTTCCTCGT TTCTGTGCTG ATTCCGTCTT CCCTCTGCTT    2400

AATTTTCAAA TCGATCCACC GGTTCAGAAG CTCTACGTCA CTGATATCCA TGGAGCTGTT    2460

TGGGATTTCA GGCATATCTA TCGCGGTACA CCGAGGCGTC ACTTGCTAAC AACGGGATGG    2520

AGTAAGTTTG TCAATAGCAA GAAGCTCATC GCTGGAGATT CGGTTGTGTT TATGAGAAAA    2580

TCTGCAGATG AGATGTACAT CGGTGTTAGG CGAACTCCGA TCTCAAGCAG CGACGGAGGA    2640

AGTAGCTATT ACGGAGGAGA TGAGTATAAC GGTTACTACA GTCAGAGTAG CGTTGCCAAG    2700

GAAGATGATG GGAGTCCGAA GAAGACGTTT AGGAGATCTG GAATGGTAA GTTGACTGCT     2760

GAGGCTGTAC GATCGATCAA TAGAGCGTCT CAGGGATTAC CGTTTGAGGT GGTGTTTTAT    2820

CCGGCTGCTG GATGGTCTGA GTTTGTTGTG AGAGCTGAAG ATGTTGAGTC TTCAATGTCT    2880
```

```
ATGTATTGGA CTCCTGGGAC TCGAGTCAAG ATGGCTATGG AGACTGAAGA TTCTTCTCGG    2940
ATCACATGGT TTCAAGGCAT CGTTTCCTCT ACTTATCAGG AGACCGGTCC ATGGCGTGGA    3000
TCTCCATGGA AGCAGCTTCA GGTATATGAT GTTTTTGAAA TGGTCTTTGC TCTTCTTATC    3060
TCTGTGATGT TGAGTTAATG GAACAATTCA GAATCGATCT TGTATCTGTT GTGTGCAAGC    3120
CTTTAAGATG ATGTTTAAGT CTCATCCTGG TTATTCAAAT GTCAATTGGG TTTTGAATGT    3180
TGTTTTGATT GCTGTGTTGT TTGTTTTGAA GCTAAATATT GGAAACAGGA TAAGTTAANT    3240
CATACGAAAA TGAATGTTCT GTCTCAGATT CATCTTCTAT AAGATGGAAT TGAAACTGGA    3300
AGATTTGGCT TAGTATTGTN TGTNTTGAGC GTCCGTGATG TAGAGTTGTT TTCATTATCC    3360
TTCTTTGGCC ACGCATTGTA CATTGTGTTT GTTAAACTAG AGTTCCTCTG ATTAGTCTTA    3420
TGAGATACTC CTTTTTTGCC AATATATTCT ACTTCCTCTG ATTAGTTCCT TTGTTTTTAA    3480
CTTGCGTAGA TCACATGGGA TGAACCTGAG ATTCTGCAAA ACGTGAAGAG GGTGAATCCA    3540
TGGCAAGTGG AAATTGCTGC ACATGCAACT CAACTGCATA CCCCTTTCCC TCCAGCAAAG    3600
AGGTTGAAGT ATCCACAACC CGGAGGAGGG TTCTTGAGTG GAGATGATGG AGAAATCCTT    3660
TATCCTCAAA GTGGACTGTC TAGTGCAGCA GCACCTGATC CAAGTCCTTC TATGTTCTCG    3720
TATTCTACAT TTCCTGCTGG CATGCAGGGA GCCAGGCAAT ATGATTTTGG GTCTTTCAAT    3780
CCAACCGGAT TCATTGGAGG AAATCCTCCC CAGCTATTCA CCAATAACTT CTTAAGTCCG    3840
CTTCCTGATT TGGGAAAAGT GTCGACTGAG ATGATGAACT TTGGCAGTCC GCCATCAGAT    3900
AACTTATCGC CTAATAGCAA CACCACTAAT CTGTCCTCTG GAAATGACCT GGTTGGAAAC    3960
CGAGGCCCCC TTTCAAAGAA AGTTAACTCG ATTCAGTTGT TTGGCAAGAT CATTACCGTG    4020
GAGGAGCATT CTGAGAGCGG TCCTGCAGAG TCTGGCTTGT GTGAAGAGGA TGGCAGCAAA    4080
GAGTCCAGCG ACAATGAGAC ACAGTTGTCC TTATCACATG CTCCTCCAAG CGTGCCTAAA    4140
CATTCCAACA GCAACGCAGG TTCTAGCTCC CAAGGTATAT TCCGATCTCT CTCAAGTACA    4200
ATAATCAATT GAATCAGTTG CTATAAGCTT TTATTACTGT TTTGCACAAG GCAATTTCTC    4260
TTCCTTTCCC ATGAACTATA TTATGTAGAG TAGGAAACAC AATCATGATT TCTGATATGA    4320
CTTGACTGAT GATGATACTT GTNAAAACTA TCTATATATC TCTTCAGTAA TCAGTCGCCT    4380
TGAGGTAATT GGAATTTGGA ACTTGAACAT TACTTGGATT TTAACTTTTC AATAGCATAA    4440
GCNTTCCTGT TTCATCATAT ATGTTTCACT ATACTTGTAT GCTTTTATTA CTGCTGATAT    4500
TTACTATTCC TGCTATTTTT TTTGGGTCTC GTTAACGGTA ATAAGGACAC AGAATTGGCT    4560
CTTTTATCCA TCAGAACTAG ACATTACTGT ACAAGTAGAT GAAGAATTAT GTGGTTCCAT    4620
TACAAATTTA ATTTGCAGAA AGCTTGAAGC TGCTGCTTAT AGACGATTAT AATGTTGGAA    4680
GATCCTGAAG CTTGGAATGA TTTGTACTTT TCTTTTGTTT GTGTGTGTTT TGACAGGTTA    4740
AAAAGTGAAA GAAGTGGTGG ATCTTTGCTG GAATCTCCAA GTCCTAAGTA GTAGTAGTAG    4800
TACATTATAT ATAATTCTGT TGTTTCTGCA ATTGACTTTT CTCTGGCTTT TCTTTGCCAC    4860
GTGACGATTC CGGTTTTTAC TTTCTTTCTT TTTTTTTTAT CAATTTCTCA GACACATTTG    4920
ATGAACATCT CGCTCTCATC TAATCGTTAA CTATTTTTAT TGGGTAAAT GTCTGGATTT     4980
GTCTTACCTA AACATGTTTT AAGACTGATG TTTATGCAGA GTGAAAACAG TAAATAATTT    5040
AATGCTTTAT TCAATCCCTA TGCAATGGAT CTCAACTTAA CGGCGCCAAC CAGAGAGTTT    5100
TACTAACTGT CTTTTGCTTT TAGTTAATAT TCCTAATAAA TAAAAAGACT GCCAATAATA    5160
AAATCGGACC ATTTTTATTC TCATAATAAA TAAAAGAAGC TCAAGGGAGG TCCTCCTAC     5220
```

```
ACTTTTCTGA CTCCTTTATG TTCTGTTCTC TGTGATTCAT TAACGGATCA GCTATAGCAT        5280

TTCCAATTTG TCAGTAAGTT AGGGTTGGTT TGGATTAGCT AATAGCTACC AATGAG           5336
```

(2) INFORMATION FOR SEQ ID NO: 12:

(i) SEQUENCE CHARACTERISTICS:
        (A) LENGTH: 584 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

```
Met Ser Pro Pro Ser Ala Thr Ala Gly Asp Ile Asn His Arg Glu Val
1               5                   10                  15

Asp Pro Thr Ile Trp Arg Ala Cys Ala Gly Ala Ser Val Gln Ile Pro
            20                  25                  30

Val Leu His Ser Arg Val Tyr Tyr Phe Pro Gln Gly His Val Glu His
        35                  40                  45

Cys Cys Pro Leu Leu Ser Thr Leu Pro Ser Ser Thr Ser Pro Val Pro
50                  55                  60

Cys Ile Ile Thr Ser Ile Gln Leu Leu Ala Asp Pro Val Thr Asp Glu
65                  70                  75                  80

Val Phe Ala His Leu Ile Leu Gln Pro Ile Thr Gln Gln Phe Thr
                85                  90                  95

Pro Thr Asn Tyr Ser Arg Phe Gly Arg Phe Asp Gly Asp Val Asp Asp
                100                 105                 110

Asn Asn Lys Val Thr Thr Phe Ala Lys Ile Leu Thr Pro Ser Asp Ala
            115                 120                 125

Asn Asn Gly Gly Gly Phe Ser Val Pro Arg Phe Cys Ala Asp Ser Val
130                 135                 140

Phe Pro Leu Leu Asn Phe Gln Ile Asp Pro Pro Val Gln Lys Leu Tyr
145                 150                 155                 160

Val Thr Asp Ile His Gly Ala Val Trp Asp Phe Arg His Ile Tyr Arg
                165                 170                 175

Gly Thr Pro Arg Arg His Leu Leu Thr Thr Gly Trp Ser Lys Phe Val
                180                 185                 190

Asn Ser Lys Lys Leu Ile Ala Gly Asp Ser Val Val Phe Met Arg Lys
            195                 200                 205

Ser Ala Asp Glu Met Tyr Ile Gly Val Arg Arg Thr Pro Ile Ser Ser
    210                 215                 220

Ser Asp Gly Gly Ser Ser Tyr Tyr Gly Gly Asp Glu Tyr Asn Gly Tyr
225                 230                 235                 240

Tyr Ser Gln Ser Ser Val Ala Lys Glu Asp Asp Gly Ser Pro Lys Lys
                245                 250                 255

Thr Phe Arg Arg Ser Gly Asn Gly Lys Leu Thr Ala Glu Ala Val Arg
                260                 265                 270

Ser Ile Asn Arg Ala Ser Gln Gly Leu Pro Phe Glu Val Val Phe Tyr
            275                 280                 285

Pro Ala Ala Gly Trp Ser Glu Phe Val Val Arg Ala Glu Asp Val Glu
        290                 295                 300

Ser Ser Met Ser Met Tyr Trp Thr Pro Gly Thr Arg Val Lys Met Ala
305                 310                 315                 320

Met Glu Thr Glu Asp Ser Ser Arg Ile Thr Trp Phe Gln Gly Ile Val
                325                 330                 335
```

Ser Ser Thr Tyr Gln Glu Thr Gly Pro Trp Arg Gly Ser Pro Trp Lys
        340                 345                 350

Gln Leu Gln Ile Thr Trp Asp Glu Pro Glu Ile Leu Gln Asn Val Lys
        355                 360                 365

Arg Val Asn Pro Trp Gln Val Glu Ile Ala Ala His Ala Thr Gln Leu
        370                 375             380

His Thr Pro Phe Pro Pro Ala Lys Arg Leu Lys Tyr Pro Gln Pro Gly
385                 390                 395                 400

Gly Gly Phe Leu Ser Gly Asp Asp Gly Glu Ile Leu Tyr Pro Gln Ser
                405                 410                 415

Gly Leu Ser Ser Ala Ala Ala Pro Asp Pro Ser Pro Ser Met Phe Ser
            420                 425                 430

Tyr Ser Thr Phe Pro Ala Gly Met Gln Gly Ala Arg Gln Tyr Asp Phe
            435                 440             445

Gly Ser Phe Asn Pro Thr Gly Phe Ile Gly Gly Asn Pro Pro Gln Leu
        450                 455                 460

Phe Thr Asn Asn Phe Leu Ser Pro Leu Pro Asp Leu Gly Lys Val Ser
465                 470                 475                 480

Thr Glu Met Met Asn Phe Gly Ser Pro Pro Ser Asp Asn Leu Ser Pro
                485                 490                 495

Asn Ser Asn Thr Thr Asn Leu Ser Ser Gly Asn Asp Leu Val Gly Asn
                500                 505             510

Arg Gly Pro Leu Ser Lys Lys Val Asn Ser Ile Gln Leu Phe Gly Lys
            515                 520                 525

Ile Ile Thr Val Glu Glu His Ser Glu Gly Ser Pro Ala Glu Ser Gly
530                 535                 540

Leu Cys Glu Glu Asp Gly Ser Lys Glu Ser Ser Asp Asn Glu Thr Gln
545                 550                 555                 560

Leu Ser Leu Ser His Ala Pro Pro Ser Val Pro Lys His Ser Asn Ser
                565                 570                 575

Asn Ala Gly Ser Ser Ser Gln Gly
            580

(2) INFORMATION FOR SEQ ID NO: 13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

CGTATCGGTT TTCGATTACC GTATT                                                  25

(2) INFORMATION FOR SEQ ID NO: 14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

CGTTTCCGTT TCCGTTTACC GTTTT                                                  25

(2) INFORMATION FOR SEQ ID NO: 15:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

TGCTTGTGCT GGAGCC                                      16

(2) INFORMATION FOR SEQ ID NO: 16:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

GTTATCATCA ACATCGCCAT CGAATCTGCC G                    31

(2) INFORMATION FOR SEQ ID NO: 17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

CTGCTGCTGC GTGATCGG                                    18

(2) INFORMATION FOR SEQ ID NO: 18:

(i) SEQUENCE CHARACTERISTICS:
        (A) LENGTH: 83 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..83
        (D) OTHER INFORMATION:/note= "Figure 9, sequence of
            ZmVP1"

(xi) SEQUENCE DESCRIPTION: SEQ ID NO: 18:

```
Leu Leu Gln Lys Val Leu Lys Gln Ser Asp Val Gly Ser Leu Gly Arg
1               5                   10                  15

Ile Val Leu Pro Lys Lys Glu Ala Glu Val His Leu Pro Glu Leu Lys
                20                  25                  30

Thr Arg Asp Gly Ile Ser Ile Pro Met Glu Asp Ile Gly Thr Ser Arg
            35                  40                  45

Val Trp Asn Met Arg Tyr Arg Phe Trp Pro Asn Asn Lys Ser Arg Met
    50                  55                  60

Tyr Leu Leu Glu Asn Thr Gly Glu Phe Val Arg Ser Asn Glu Leu Gln
65                  70                  75                  80
```

Glu Gly Asp (2) INFORMATION FOR SEQ ID NO: 19:

(i) SEQUENCE CHARACTERISTICS:
        (A) LENGTH: 67 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..67
        (D) OTHER INFORMATION:/note= "Figure 9, sequence of
            OSR1187"

(xi) SEQUENCE DESCRIPTION: SEQ ID NO: 19:

```
Glu Lys Arg Leu Thr Pro Ser Asp Val Gly Lys Leu Asn Arg Leu Val
 1               5                  10                  15

Ile Pro Lys Gln Xaa Ala Glu Arg Tyr Phe Xaa Leu Gly Gly Gly Asp
            20                  25                  30

Ser Gly Xaa Lys Xaa Leu Leu Leu Ser Xaa Glu Asp Glu Ser Gly Lys
            35                  40                  45

Pro Trp Arg Phe Arg Tyr Ser Tyr Trp Thr Ser Gln Ser Tyr Val
 50                  55                  60

Leu Xaa Lys
 65
```

(2) INFORMATION FOR SEQ ID NO: 20:

(i) SEQUENCE CHARACTERISTICS:
        (A) LENGTH: 131 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..131
        (D) OTHER INFORMATION:/note= "Figure 9, sequence of
            ATTS3975"

(xi) SEQUENCE DESCRIPTION: SEQ ID NO: 20:

```
Leu Arg Lys His Thr Tyr Asn Glu Glu Leu Gln Ser Lys Arg Arg
 1               5                  10                  15

Arg Asn Gly Asn Gly Asn Met Thr Arg Thr Leu Leu Thr Ser Gly Leu
            20                  25                  30

Ser Asn Asp Gly Val Ser Thr Thr Gly Phe Arg Ser Ala Glu Ala Leu
            35                  40                  45

Phe Glu Lys Ala Val Thr Pro Ser Asp Val Gly Lys Leu Asn Arg Leu
 50                  55                  60

Val Ile Pro Lys His His Ala Glu Lys His Phe Pro Leu Pro Ser Ser
 65                  70                  75                  80

Asn Val Ser Val Lys Gly Val Leu Leu Asn Phe Glu Asp Val Asn Gly
                85                  90                  95

Lys Val Trp Arg Phe Arg Tyr Ser Tyr Trp Asn Ser Ser Gln Ser Tyr
                100                 105                 110

Val Leu Thr Lys Gly Trp Ser Arg Phe Val Lys Glu Lys Asn Leu Arg
                115                 120                 125
```

```
Ala Gly Asp
    130
```

(2) INFORMATION FOR SEQ ID NO: 21:

(i) SEQUENCE CHARACTERISTICS:
        (A) LENGTH: 512 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..512
        (D) OTHER INFORMATION:/note= "Figure 9, sequence of
            At41a"

(xi) SEQUENCE DESCRIPTION: SEQ ID NO: 21:

```
Leu Ala Asp Pro Val Thr Asp Glu Val Phe Ala His Leu Ile Leu Gln
1               5                   10                  15

Pro Ile Thr Gln Gln Gln Phe Thr Pro Thr Asn Tyr Ser Arg Phe Gly
            20                  25                  30

Arg Phe Asp Gly Asp Val Asp Asp Asn Asn Lys Val Thr Thr Phe Ala
        35                  40                  45

Lys Ile Leu Thr Pro Ser Asp Ala Asn Asn Gly Gly Phe Ser Val
50                  55                  60

Pro Arg Phe Cys Ala Asp Ser Val Phe Pro Leu Leu Asn Phe Gln Ile
65                  70                  75                  80

Asp Pro Pro Val Gln Lys Leu Tyr Val Thr Asp Ile His Gly Ala Val
                85                  90                  95

Trp Asp Phe Arg His Ile Tyr Arg Gly Thr Pro Arg Arg His Leu Leu
            100                 105                 110

Thr Thr Gly Trp Ser Lys Phe Val Asn Ser Lys Lys Leu Ile Ala Gly
            115                 120                 125

Asp Ser Val Val Phe Met Arg Lys Ser Ala Asp Glu Met Tyr Ile Gly
130                 135                 140

Val Arg Arg Thr Pro Ile Ser Ser Ser Asp Gly Gly Ser Ser Tyr Tyr
145                 150                 155                 160

Gly Gly Asp Glu Tyr Asn Gly Tyr Tyr Ser Gln Ser Ser Val Ala Lys
                165                 170                 175

Glu Asp Asp Gly Ser Pro Lys Lys Thr Phe Arg Arg Ser Gly Asn Gly
            180                 185                 190

Lys Leu Thr Ala Glu Ala Val Arg Ser Ile Asn Arg Ala Ser Gln Gly
        195                 200                 205

Leu Pro Phe Glu Val Val Phe Tyr Pro Ala Ala Gly Trp Ser Glu Phe
    210                 215                 220

Val Val Arg Ala Glu Asp Val Glu Ser Ser Met Ser Met Tyr Trp Thr
225                 230                 235                 240

Pro Gly Thr Arg Val Lys Met Ala Met Glu Thr Glu Asp Ser Ser Arg
                245                 250                 255

Ile Thr Trp Phe Gln Gly Ile Val Ser Ser Thr Tyr Gln Glu Thr Gly
            260                 265                 270

Pro Trp Arg Gly Ser Pro Trp Lys Gln Leu Gln Ile Thr Trp Asp Glu
        275                 280                 285

Pro Glu Ile Leu Gln Asn Val Lys Arg Val Asn Pro Trp Gln Val Glu
    290                 295                 300
```

-continued

```
Ile Ala Ala His Ala Thr Gln Leu His Thr Pro Phe Pro Pro Ala Lys
305                 310                 315                 320

Arg Leu Lys Tyr Pro Gln Pro Gly Gly Phe Leu Ser Gly Asp Asp
            325                 330                 335

Gly Glu Ile Leu Tyr Pro Gln Ser Gly Leu Ser Ser Ala Ala Ala Pro
            340                 345                 350

Asp Pro Ser Pro Ser Met Phe Ser Tyr Ser Thr Phe Pro Ala Gly Met
            355                 360                 365

Gln Gly Ala Arg Gln Tyr Asp Phe Gly Ser Phe Asn Pro Thr Gly Phe
370                 375                 380

Ile Gly Gly Asn Pro Pro Gln Leu Phe Thr Asn Asn Phe Leu Ser Pro
385                 390                 395                 400

Leu Pro Asp Leu Gly Lys Val Ser Thr Glu Met Met Asn Phe Gly Ser
            405                 410                 415

Pro Pro Ser Asp Asn Leu Ser Pro Asn Ser Asn Thr Thr Asn Leu Ser
            420                 425                 430

Ser Gly Asn Asp Leu Val Gly Asn Arg Gly Pro Leu Ser Lys Lys Val
            435                 440                 445

Asn Ser Ile Gln Leu Phe Gly Lys Ile Ile Thr Val Glu Glu His Ser
450                 455                 460

Glu Ser Gly Pro Ala Glu Ser Gly Leu Cys Glu Glu Asp Gly Ser Lys
465                 470                 475                 480

Glu Ser Ser Asp Asn Glu Thr Gln Leu Ser Leu Ser His Ala Pro Pro
            485                 490                 495

Ser Val Pro Lys His Ser Asn Ser Asn Ala Gly Ser Ser Ser Gln Gly
            500                 505                 510
```

(2) INFORMATION FOR SEQ ID NO: 22:

(i) SEQUENCE CHARACTERISTICS:
        (A) LENGTH: 123 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..123
        (D) OTHER INFORMATION:/note= "Figure 9, sequence of
            OSS2204"

(xi) SEQUENCE DESCRIPTION: SEQ ID NO: 22:

```
Ala Val Lys Arg Leu Ala Arg Ile Pro His Met Phe Cys Lys Thr Leu
1               5                   10                  15

Thr Ala Ser Asp Thr Ser Thr His Gly Gly Phe Ser Val Pro Arg Arg
            20                  25                  30

Ala Ala Glu Asp Cys Phe Pro Pro Leu Asp Tyr Ser Leu Gln Arg Pro
            35                  40                  45

Phe Gln Glu Leu Val Ala Lys Asp Leu His Gly Thr Glu Trp Arg Phe
50                  55                  60

Arg His Ile Tyr Arg Gly Gln Pro Arg Arg His Leu Leu Thr Thr Gly
65                  70                  75                  80

Trp Ser Gly Phe Ile Asn Lys Lys Leu Val Ser Gly Asp Cys Ser
            85                  90                  95

Ala Ile Pro Gln Glu Val Lys Met Glu Asn Phe Asp Trp Gly Val Arg
            100                 105                 110
```

Arg Ala Ala Gln Leu Lys Asn Ala Ile Ser Phe
        115                 120

(2) INFORMATION FOR SEQ ID NO: 23:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..107
        (D) OTHER INFORMATION:/note= "Figure 9, sequence of
            Zm41a"

(xi) SEQUENCE DESCRIPTION: SEQ ID NO: 23:

Asp Gly Ser Ala Glu Asp Gly Val Arg Lys Gly Glu Thr Val Lys Gln
1               5                   10                  15

Arg Phe Ser Arg Met Pro His Met Phe Cys Lys Thr Leu Thr Ala Ser
            20                  25                  30

Asp Thr Ser Thr His Gly Gly Phe Ser Val Pro Arg Arg Ala Ala Glu
        35                  40                  45

Asp Cys Phe Pro Pro Leu Asp Tyr Ser Gln Gln Arg Pro Ser Gln Glu
    50                  55                  60

Leu Val Ala Lys Asp Leu His Gly Thr Glu Trp Arg Phe Arg His Ile
65                  70                  75                  80

Tyr Arg Gly Gln Pro Arg Arg His Leu Leu Thr Thr Gly Trp Ser Ala
                85                  90                  95

Phe Val Asn Lys Lys Lys Leu Val Ser Gly Asp
                100                 105

(2) INFORMATION FOR SEQ ID NO: 24:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..72
        (D) OTHER INFORMATION:/note= "Figure 9, sequence of
            T21748"

(xi) SEQUENCE DESCRIPTION: SEQ ID NO: 24:

Leu Asn Arg Leu Val Ile Pro Lys Gln His Ala Glu Lys His Phe Pro
1               5                   10                  15

Leu Pro Ser Pro Ser Pro Ala Val Thr Lys Gly Val Leu Ile Asn Phe
            20                  25                  30

Glu Asp Val Asn Arg Lys Val Trp Arg Phe Arg Tyr Ser Tyr Trp Asn
        35                  40                  45

Ser Ser Gln Ser Tyr Val Leu Thr Lys Gly Trp Ser Arg Phe Val Lys
    50                  55                  60

Glu Lys Asn Leu Arg Ala Gly Asn
65                  70

(2) INFORMATION FOR SEQ ID NO: 25:

(i) SEQUENCE CHARACTERISTICS:
    (A) LENGTH: 461 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Peptide
    (B) LOCATION:1..461
    (D) OTHER INFORMATION:/note= "Figure 9, sequence of ATTS1074"

(xi) SEQUENCE DESCRIPTION: SEQ ID NO: 25:

```
Gly Phe Ser Gly Phe Leu Arg Asp Asp Glu Ser Thr Thr Thr Thr Ser
1               5                   10                  15

Lys Leu Met Met Met Lys Arg Asn Gly Asn Asn Asp Gly Asn Ala Ala
            20                  25                  30

Ala Thr Gly Arg Val Arg Val Glu Ala Val Ala Glu Ala Val Ala Arg
        35                  40                  45

Ala Ala Cys Gly Gln Ala Phe Glu Val Val Tyr Tyr Pro Arg Ala Ser
    50                  55                  60

Thr Pro Glu Phe Cys Val Lys Ala Ala Asp Val Arg Ser Ala Met Arg
65                  70                  75                  80

Ile Arg Trp Cys Ser Gly Met Arg Phe Lys Met Ala Phe Glu Thr Glu
                85                  90                  95

Asp Ser Ser Arg Ile Ser Trp Phe Met Gly Thr Val Ser Ala Val Gln
                100                 105                 110

Val Ala Asp Pro Ile Arg Trp Pro Asn Ser Pro Trp Arg Leu Leu Gln
            115                 120                 125

Val Ala Trp Asp Glu Pro Asp Leu Leu Gln Asn Val Lys Arg Val Ser
130                 135                 140

Pro Trp Leu Val Glu Leu Val Ser Asn Met Pro Thr Ile His Leu Ser
145                 150                 155                 160

Pro Phe Ser Pro Arg Lys Lys Ile Arg Ile Pro Gln Pro Phe Glu Phe
                165                 170                 175

Pro Phe His Gly Thr Lys Phe Pro Ile Phe Ser Pro Gly Phe Ala Asn
            180                 185                 190

Asn Gly Gly Gly Glu Ser Met Cys Tyr Leu Ser Asn Asp Asn Asn Asn
        195                 200                 205

Ala Pro Glu Gly Ile Gln Gly Ala Arg Gln Ala Gln Gln Leu Phe Gly
    210                 215                 220

Ser Pro Ser Pro Ser Leu Leu Ser Asp Leu Asn Leu Ser Ser Tyr Thr
225                 230                 235                 240

Gly Asn Asn Lys Leu His Ser Pro Ala Met Phe Leu Ser Ser Phe Asn
                245                 250                 255

Pro Arg His His His Tyr Gln Ala Arg Asp Ser Glu Asn Ser Asn Asn
            260                 265                 270

Ile Ser Cys Ser Leu Thr Met Gly Asn Pro Ala Met Val Gln Asp Lys
        275                 280                 285

Lys Lys Ser Val Gly Ser Val Lys Thr His Gln Phe Val Leu Phe Gly
    290                 295                 300

Gln Pro Ile Leu Thr Glu Gln Gln Val Met Asn Arg Lys Arg Phe Leu
305                 310                 315                 320

Glu Glu Glu Ala Glu Ala Glu Glu Lys Gly Leu Val Ala Arg Gly
                325                 330                 335
```

```
Leu Thr Trp Asn Tyr Ser Leu Gln Gly Leu Glu Thr Gly His Cys Lys
            340                 345                 350

Val Phe Met Glu Ser Glu Asp Val Gly Arg Thr Leu Asp Leu Ser Val
            355                 360                 365

Ile Gly Ser Tyr Gln Glu Leu Tyr Arg Lys Leu Ala Glu Met Phe His
            370                 375                 380

Ile Glu Glu Arg Ser Asp Leu Leu Thr His Val Val Tyr Arg Asp Ala
385                 390                 395                 400

Asn Gly Val Ile Lys Arg Ile Gly Asp Glu Pro Phe Ser Asp Phe Met
                405                 410                 415

Lys Ala Thr Lys Arg Leu Pro Ile Lys Met Asp Ile Gly Gly Asp Asn
            420                 425                 430

Val Arg Lys Thr Trp Ile Thr Gly Ile Arg Thr Gly Glu Asn Gly Ile
            435                 440                 445

Asp Ala Ser Thr Lys Thr Gly Pro Leu Ser Ile Phe Ala
450                 455                 460

(2) INFORMATION FOR SEQ ID NO: 26:

(i) SEQUENCE CHARACTERISTICS:
        (A) LENGTH: 323 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:3..323

(xi) SEQUENCE DESCRIPTION: SEQ ID NO: 26:

AG GAC GGC AGC GCC GAG GAC GGC GTA CGG AAG GGG GAA ACC GTG AAG        47
   Asp Gly Ser Ala Glu Asp Gly Val Arg Lys Gly Glu Thr Val Lys
    1               5                  10                  15

CAG CGG TTC TCG CGG ATG CCG CAC ATG TTC TGC AAG ACG CTC ACG GCC        95
Gln Arg Phe Ser Arg Met Pro His Met Phe Cys Lys Thr Leu Thr Ala
                20                  25                  30

TCC GAC ACC AGC ACG CAC GGG GGT TTC TCC GTG CCG CGC CGC GCC GCC       143
Ser Asp Thr Ser Thr His Gly Gly Phe Ser Val Pro Arg Arg Ala Ala
            35                  40                  45

GAG GAC TGC TTC CCG CCT CTG GAC TAC AGC CAG CAG CGA CCG TCG CAG       191
Glu Asp Cys Phe Pro Pro Leu Asp Tyr Ser Gln Gln Arg Pro Ser Gln
        50                  55                  60

GAG CTT GTG GCC AAG GAT TTG CAC GGA ACC GAG TGG AGG TTC CGC CAC       239
Glu Leu Val Ala Lys Asp Leu His Gly Thr Glu Trp Arg Phe Arg His
65                  70                  75

ATT TAT CGA GGG CAG CCC CGC AGA CAC CTT TTA ACC ACT GGA TGG AGT       287
Ile Tyr Arg Gly Gln Pro Arg Arg His Leu Leu Thr Thr Gly Trp Ser
 80                  85                  90                  95

GCC TTT GTC AAC AAG AAG AAG CTT GTC TCA GGG GAC                       323
Ala Phe Val Asn Lys Lys Lys Leu Val Ser Gly Asp
                100                 105

(2) INFORMATION FOR SEQ ID NO: 27:

(i) SEQUENCE CHARACTERISTICS:
        (A) LENGTH: 107 amino acids
        (B) TYPE: amino acid
        (D) TOPOLOGY: linear (ii) MOLECULE TYPE: protein
```

(xi) SEQUENCE DESCRIPTION: SEQ ID NO: 27:

```
Asp Gly Ser Ala Glu Asp Gly Val Arg Lys Gly Glu Thr Val Lys Gln
 1               5                  10                  15
Arg Phe Ser Arg Met Pro His Met Phe Cys Lys Thr Leu Thr Ala Ser
                20                  25                  30
Asp Thr Ser Thr His Gly Gly Phe Ser Val Pro Arg Arg Ala Ala Glu
            35                  40                  45
Asp Cys Phe Pro Pro Leu Asp Tyr Ser Gln Gln Arg Pro Ser Gln Glu
        50                  55                  60
Leu Val Ala Lys Asp Leu His Gly Thr Glu Trp Arg Phe Arg His Ile
65                  70                  75                  80
Tyr Arg Gly Gln Pro Arg Arg His Leu Leu Thr Thr Gly Trp Ser Ala
                85                  90                  95
Phe Val Asn Lys Lys Lys Leu Val Ser Gly Asp
                100                 105
```

(2) INFORMATION FOR SEQ ID NO: 28:

(i) SEQUENCE CHARACTERISTICS:
        (A) LENGTH: 7815 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 28:

```
AAGCTTTAGT GACTAGTGAG AGTGATTTGT TGTGTTCTTT TGAGCTCTTG CGCTTGGATT    60
GCTTTCTTCT TTCTCATTCT TTCTTGAGAT CAATACTCAC TTGTAACCGA GGCAAGAGAC   120
ACCAATTGTG TGGTGGTCCT TGCGGGTAAG TTTTGTTCCC GGTTGATTTG AGAAGAGAAA   180
GCTCACTCGG TCCGAGGGAC CGTTTGAAAG AGGGAAGGGG TTGAAAAAGA CCCGGCCTTT   240
GTGGCCTCCT CAATGGGGAG TAGGTTTGCG AAAACCGAAC CTCGGTAAAA CAAATCCGCG   300
TGTCACACTT CTTATCTGCT TGCGATTTGT TTTTCACCCT CTCTCGCGGA CTCGATTATA   360
TTTCTAACGC TAACCCGACT TGTAGTTGTG ATTAACTTTG TAAATTTCAG TTTCGCCCTA   420
TTCACCCCCC TCTATGCGAC TTTCAGTAGT TCATCTATCC CATGTTTTAC CCCTATTTGC   480
TTGGATCTGA GCTGATTGCG ACTTAGAGAC TAAACTGCTG AACTTATGAA CCTGTGAATA   540
AAATACTAAG TAAACTAGTT AGTCCGAATG TTTGTGATAG TCATCAAGCA CCAAAATCAA   600
TATAAAAATG GTTTAAGGCC AATTTCCTTT CGCAAAGATA TGGAATGTCA TAACCCGTCA   660
ATCCTTCATG TAACAATGGT CGTGCGTTCC CTCAACCATA CAAAGGGACA TGGCCGCACT   720
GAAAAGGCAG ACACACATAG TTTTACATAT TTTCTACGCT AGCACAATAG CCTCGTTCTC   780
CACTCTGCAA CTCACGAAAA CAGTAACAAA AACTTCAACA ACATACTAGG CATATTTTCT   840
CTCCAAACTG GTCTAAAAAC TCTCTTCAAA CTCACTTCGA GCAAGGTAAT CGGGACATTA   900
GCACCGCAAT CCCTTTCCTA AACTCCAATC TACTTGTCAT GGGGTTGAAA TCACGATAGT   960
TAATGTGCTA GGTAAGGGGT ATGGCGCGTT GCATTTAGCT TTCGATGGGA TTCGATCGTT  1020
TTCCCATGAC GCCTTCACTC TCGAAACCAA TGTCACATTT TGAGATCTTG GACTTTGTTT  1080
CCACCAAGGG ATTGCGCCAT GCAGCTCCTC ACCCGCGTCC GGACGGTAGC ACACGAGAGG  1140
AACCATGAAG GCGCCTTCGA CATGCGGGCC TTGGATGGGT CGACGAAAAA GGTCCTAGGT  1200
TCGCGGCCTA ATGTCGCACG ACCCGATGCT TCGTACAAGG TCTATAGAAC GGTTAGGGCA  1260
```

```
TAAGGGCACC TAGTTCAAAA AACTCAAAAG GGCCCAACCG AGGGTAGGGT TGGCAGCGGG    1320

CGACGAAGCG AATATAGCCG CACGTGCCAC CACACAAAAT GAGGGCTAAT CTTCGATGTC    1380

GCACCGTCTA GGACCCATCA TGCATGTAGG ATCCATCTTC GATGTCAATC ACGATCCCTC    1440

ATGCTCTTAC GACCTCCTCG ACACGCCTTC GTGCGATTGC TAGAGGACAT TGTCGACGGA    1500

ATATCCCCTC TTTGCCCTGT GACTTGGATG ATTATACATT TATGGTAGGT GTTATGGATG    1560

TTATAAATGG ATGTATATGA ATGTGTGTGT ATCTATGTGT TGTGGATGAA TATAAATAAT    1620

TATTTTCTAA CTGGTAAGAA TCATTTCTGG TGACTAGGTT CAGTCGATAA AAATTAGTAT    1680

GTCTAATTTG TGTATTATGT CTATGAAAAT TAGTTAATTT TAGTTTATTA ATCTTCAAAA    1740

GTTACAGACC GACGAAAACT AGACTATCAG TCACAACTGG TAAGAAGGAA CAACGACAAC    1800

AGAGATGCCA AGTTACTGGC TTACTGCAGC AAGCTACCGT TTTCTGCCCG CGTGTACATT    1860

GAAGCACAGG TGCGTCTACA CTCTACGCTC TCGAGTCCAA TATAAAAATA GACTGTTGGG    1920

CACCTATTGT ACCCGTACCC CTGTTCCTGC TCCTGCCGCA GTACTGAATT CTGCTGCTGC    1980

TACACTCCTC TGTCCGCATC CATCCACGTC TCTCTCCTCT GCCGCCCGCC TGCGCCACCC    2040

ATCACTGTGC GCGTCTCCCG CATCGTCCGC TCTCTTTCTT TTTCACCCTT TCCCGGCCCA    2100

TCTTCTCTTT TTACATCTGC AACGGCAGGC CGGCTGCGGC AGCGGCAGCG GCAGCTGACC    2160

AGTGACCGAC CACCCCCACA CCACTCCGGC GCCCCAATCC TCCCCCTTCT TCTTTTTCAC    2220

TACTACTACT GTACTGCACG GTCGCCAAGC GCCAGAACGC AGTGGAGAAC GGGGGGCAGG    2280

ACTCCAACAA GCGTTGATTT CTGCCGGCAC GCACGGCACG GCACGGGCA CGGGCACGGG    2340

CGTCCCCCCT CACTCACGCA CCCTGCGTCT TTTCCGGCTG CCGCTGCTGG CTGGCTGGCT    2400

CTGGCTCACA GCTACAGGCT ACAGTGACCG CCACGCAACC CACACTGTCT CTGTCCTCGT    2460

CTCCCTCTCC CCTCCTAGCT CTAGCTGGAT AGGTGGGCTC TGGGGAGGAG GAGGAGGGTA    2520

GCTAGGTAGT AGCTGCCTAT AGGCCTCGGC CCCCATTCAT GGCCATTACC ACGATGTGTC    2580

ACCCCACCAC ACCGCCCTCT CCGATGCTGC CTCCCTCATG ATAACCCTCT CCCTGGTGGT    2640

TGTTCTTTGC CTTGTTGCCG TGCAGCCTCC ACCCCCACCC TCCTCATTAA TCACTTGCTA    2700

GCTCCCTGCC TCCCTCCCGG CTCCCGCTCC CCCTTCTCGT GCTTCGCGCC CCCGCAGCAG    2760

CCATGGCGGG GATCGACCTC AACGACACCG TGGAGGAGGA CGAGGAGGAG GCGGAGCCCG    2820

GCAACGCCTG CTCCCAGCAG AGCCGGACCA GCTCCGCGGC CACGTTCCCG CCGCCGCCGC    2880

CGAACCAGCC GAGGCCGAGC GCCGCGGTGT GCCTCGAGCT GTGGCACGCC TGCGCCGGCC    2940

CCGTCGCGCC GCTGCCGAGG AAAGGGAGCG TCGTGGTGTA CCTCCCGCAG GGACACATCG    3000

AGCACCTCGG CGACGCCGCG GCCGCCGGCG GAGGCGCGCC GCCGCCCGTC GCCCTGCCGC    3060

CCCACGTCTT CTGCCGCGTC GTCGACGTCA CTCTCCATGT GCGCGCGCCG GTTCCTACTC    3120

AATGCGTGCG TGTGTGGATT GCCCGTGCCG GTGTGCGGCT TCCACTGACT CTGTCCCTCT    3180

TGCGCTCGTT GCAGGCGGAC GCGTCCACGG ACGAGGTGTA CGCCCAGCTC GCCCTCGTCG    3240

CCGAGAACGA GGTGCGCGCA AGCCACAGTG CTCCACCGGC ATTGGATTCG GCTTGGTTTT    3300

CTCCTTGCGT CCACAGAGAC GAGATTTGGG CTGATTTGGT GTTTCTTGTG GCGCTTGCTT    3360

CGTGCAGGAT GTCGCGAGGC GGCTGCGCGG ACGGTCGGAG GACGGCAGCG CCGAGGACGG    3420

CGACGAAGGG GAAACCGTGA AGCAGCGGTT CTCGCGGATG CCGCACATGT TCTGCAAGAC    3480

GCTCACGGCC TCCGACACCA GCACGCACGG CGGCTTCTCC GTGCCACGCC GCGCCGCCGA    3540

GGACTGCTTC CCGCCTCTGG TACGCTTGCG TTGGCTTGGA AAGCTTCCAT CTTTTGGGTG    3600

CCCGGGTGCT GCTCTCAAGT GCGATTCTGA ATCATCTGCT CTTGGGGCGT GCAGGACTAC    3660
```

```
AGCCAGCAGC GACCGTCGCA GGAGCTTGTG GCCAAGGATT TGCACGGAAC CGAGTGGAGG    3720

TTCCGCCACA TTTATCGAGG TACATGAACA AATAATGAGA TACAAGACGA GCACATCTAC    3780

CTATTTCTTT AGCAAACTTA TGTGCTTGCT CGCCCTGAAT CATTCAGTGT CAGCGAATGA    3840

TGTCAATGGC TGCACTTCAG TTGGTGATTG TTAGCGTTTT TTTACAGGAT TTGCATTACT    3900

TGTTTGGATT GAGCACTTGG GAATGCTTCA TCTTTGCTCA CTTAAGTCCA GGATTTGAAG    3960

TCATTGTTCA GTCACTCTTT TGCTATATAT GTCACCATTA TGTGATCAGA ACTACTAATG    4020

GTTATATGTT GAGAGAGATA TACAAACTAT GTCAATGTTT CCTGCTGTCT GCATTTGCAA    4080

CCTTGTGCGC TATGCTCAGC ATTTCTCATG TCATTGGTTA GTTATTGTAG TCGTACTTAA    4140

AATTTACCAT TTTGTCCATG AAAAATCATC TGATTATATG TTCAGGAGTT CTGGTCCCGT    4200

TTTAAGGAAT GTAAAAGAAC AAACATGAGA AGCTATGTCA TGTGTGGTCC TTGGTTTCTG    4260

ATGAATCTGC ATCTGAATGT GATGCAGGGC AGCCCCGCAG ACACCTTTTA ACCACTGGAT    4320

GGAGTGCCTT TGTCAACAAG AAGAAGCTTG TCTCAGGGGA CGCCGTACTA TTTTTGAGGT    4380

AGGCCACAGC TAACATTGGA GATAATTATC ACATGTTGGT GTTGGCCCTT TCTGAAGATT    4440

CCTCATAATT TTCAGGGGTG ATAATGGGGA GCTAAGACTT GGAGTGCGCC GTGCAGCTCA    4500

GCTTAAAAAT GGATCTGCTT TTCCAGCTCT TTATAACCAG TGCTTAAATC TTGGTTCACT    4560

ACCTAATGTT GCACATGCTG TGGCCACCAA AAGTGTGTTC CACATCTACT ACAACCCCAG    4620

GTGATGATGA ATATAGCGGT TTCACTTTAA TGCTTTTGCA TGTTCAATTG TTCATGTTGT    4680

TGGCACTCTT TTAGATGATG TGAACTGAAA TGTGCTATTA ACTATACTCT TTCAATTGAC    4740

GGCGATTTGA AATTGTGTCA TTTTGTGTGA TATCATTTCC TGAGTTGTTT CGAACTATGT    4800

AATTCATGAT TCTTACTGCA ATTCAACATT AAGTGATATA TAATTACTTT TGAATTGAT    4860

ATTGTCACTT ACATTTGGAC CCTTCAATAT AATATAGTTC CACAGCTCTT TTTTTAGATA    4920

TCATGACAAG TACGCAAGTA GATCTTTGGT TCCTTATGTA TCTCATGTGC ATTTTTACCT    4980

TCTTGGACCC TGATGTGTTG CTGCAAGCCT TACCTTTTTA TCCACCAACA ATGATGGCCC    5040

TGATGGCAAT TATTGCTTTC CAAAAATCTT ACAGATTAAG CCAATCTGAA TTCATTATAC    5100

CATTTTCGAA GTTTATCAAG AGCTTCAGTC AACCATTTTC TGCTGGTTCG AGGTTCAAAG    5160

TGAAATATGA GAGTGATGAT GCTTCTGAAA GAAGGTTGGT GTGCTACAGT TCTCATCTTT    5220

TACATAGATT TATGATGGTT GACACATGAG AGTATTATGC AGATGCACAG GGATCATAGC    5280

AGGAATTGGT GATGCTGACC CCATGTGGCG TGGTTCGAAA TGGAAATGTT TGATGGTATG    5340

TTGCCTTTTA AGCTTTAATG ATTCACTTTC TGTATAACTT TTCAGGTGGT AAATTTGTGT    5400

TACATATGAA AATAATCCAT GTTAGATACA TGTTGAATAT AACATGTTTC TTTATACAGA    5460

ACACTAGGCG TGTGCATCAT GTAGCTGCCG TTGCCATCTA TTTGCACTAT TGCTTGCTA    5520

ATAAACCAAT AAGCAATCTT GCATATCTAT CCAATAATAC AATGCACAAC AAATGTTGAA    5580

AATTGCAATT GAGAGCCTAC TATGCATCCC GTGCTCCCTG AGCTGTCTCT GTTTGATGTA    5640

CAAGTTTAAT TGTAATGACA CATTTTTTTT GCATGTAAGT AGTTCTCCTT CTCCAGAGCA    5700

CATTCTTTGA TGAGCCTCAT CTTAGAGGCA TGTTGTATCT TTATCTAAAA GAGACTGCCT    5760

TGTGCCAGCC TGGTTTCCTT GATCAGGGCT CTAAGTAAAT AAGTTCATTT CATTTTGGTT    5820

TCTTATTGCC CTGCCCCTGA GTGCACATTG TAGGGGTACA TAATACCCTC TTGACTTAGT    5880

AAGCCAGTTC TAAATTGCCG CAATCTTAAT CCTCTTGATG ACCTTACATA TTTTGTATAT    5940

AAACCAATGG TTCATTTTTG CAGGTTCGAT GGGATGACGA TGTAGATTTT CGTCAACCAA    6000
```

| | |
|---|---|
| ACAGGATTTC TCCTTGGGAG ATTGAGCTGA CTAGTTCAGT TTCAGGATCT CACATGTCTG | 6060 |
| CACCAAATGC AAAGAGACTG AAACCATGTC TTCCCCATGT TAATCCAGAC TACCTAGTTC | 6120 |
| CAAGTATGCC CTGTTCTGCC CAGATGTTCG CTTAATGATT ATTTTGTTAG CTTCCGTCAT | 6180 |
| GAATAATATT TTCATTTTGA TAGATGGAAG CGGTCGTCCT GATTTTGCGG AATCTGCCCA | 6240 |
| ATTCCACAAG GTCTTGCAAG GTCAAGAATT ACTGGGTTAT AGAACTCATG ACAATGCTGC | 6300 |
| TGTTGCAACT TCTCAGCCAT GCGAAGCAAC GAACATGCAG TACATTGATG AACGAAGTTG | 6360 |
| CTCCAACGAT GCGAGTAACA TTATCCCGGG GGTTCCAAGA ATTGGTGTCA GAACACCACT | 6420 |
| CGGAAGCCCT AGGTTTTCCT ACCGTTGCTC AGGCTTTGGG GAGTCTCCAA GATTCCAAAA | 6480 |
| GGTCTTGCAA GGTCAAGAAG TATTTCATCC CTACAGAGGA ACTCTGGTCG ATGCAAGCTT | 6540 |
| GAGTAATAGT GGCTTCCATC AGCAAGATGG TTCTCATGTG CCTACTCAGG CCAGCAAGTG | 6600 |
| GCACGCACAG CTACATGGAT GTGCTTTTCG TGGCCAACAA GCACCAGCTG TTCCATCTCA | 6660 |
| ATCCTCATCC CCACCATCTG TCCTGATGTT TCAACGAGGT GATCCAAAGA TGTCCCCATT | 6720 |
| TGAATTTGGG CATTTCCACG TGAATAAGAA AGAGGATAGA CGCGCAATGT TTGTCCATGC | 6780 |
| TGGAGGCATC GGAGGAACTG AGCAAACGAC GATGCTCCAG GCTCATCATG TTTCTGGAGG | 6840 |
| AACGGGAAAC AGAGATGTGA CCGTTGAGAA ATCTCATCCC GCTGTTGCCG CTGCTTCAGA | 6900 |
| CAACAGGGAA GTTAGCAAAA ACAGTTGCAA AATATTTGGC ATATCTTTGA CCGAGAAGGT | 6960 |
| TCCAGCAATG AAAGAAAAGG GCTGTGGTGA CATCAACACC AACTATCCAT CCCCCTTCCT | 7020 |
| GTCTTTGAAG CAACAAGTGC CGAAATCGCT GGGCAACAGC TGTGCCACCG TGAGTGTCCT | 7080 |
| ACACCATGTA GCACCCTTGA TGTCTTTCTC GAGTGAAGTA ACTCTTAACT ATTATAAAAT | 7140 |
| CCTGCACGTT CATGAGCAGA GGCCTGTTGT TGCTAGGGTG ATTGACGTTT CAACAGTGGA | 7200 |
| TATGATGATC TGATGTATTG GAAAACTGTC CTGGAGGTGA AGTCATGCTA GTACCACCTC | 7260 |
| TGTCTTCATG CTAGTGACCA TGAACAGCAT CAAAGCATTT TAAGCTGACT GTTCTTAAGC | 7320 |
| ACATCGCTTA TTGTTGTTGC CTTGTGTTTT TGCAGGCTGT GTTGCGTAGT GTGGACAGTG | 7380 |
| TCGGTTTGAT GGTTCGGTAT CGTGAAGACG GGATTTGATT GAGGATCTGG CCAGATTTGT | 7440 |
| ATCCTAGTTG TAGCTGTTAG AGCACTTTGT ATGACAACCG TGAGTGCTCC GTGTTATCAG | 7500 |
| CACTAGTTGC TGCTCACAAC TTGCCTCTAT GTTCATAATC TGTATGCCAT GTCAGACCCA | 7560 |
| TTTATAGAGG GTTTGTTTGC TTGGCATAGT TCTAGACTTA AAGCATTATT ATGAGAACAA | 7620 |
| ATTTGCTCTG CACCGTATCT TTCTTACTTT CAAGTTGGCA ACGGATTAAC GGTGGAGGAG | 7680 |
| ATGATCTGAG AGGTTAGTTG TGCGACGTAT TAATGGTGTT ACATATATTA TGCTTAGGAG | 7740 |
| CATTCTGCCA GCTCATTTAT CATATACATG TCAGCACTTG ATTTGTTAAG TGTAGTTAGT | 7800 |
| AGCCTTGCAC TTTGG | 7815 |

(2) INFORMATION FOR SEQ ID NO: 29:

(i) SEQUENCE CHARACTERISTICS:
        (A) LENGTH: 736 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..736
        (D) OTHER INFORMATION:/note= "Figure 14, sequence of Z31"

(xi) SEQUENCE DESCRIPTION: SEQ ID NO: 29:

-continued

```
Met Ala Gly Ile Asp Leu Asn Asp Thr Val Glu Glu Asp Glu Glu Glu
1               5                   10                  15

Ala Glu Pro Gly Asn Ala Cys Ser Gln Gln Ser Arg Thr Ser Ser Ala
            20                  25                  30

Ala Thr Phe Pro Pro Pro Pro Asn Gln Pro Arg Pro Ser Ala Ala
        35              40                  45

Val Cys Leu Glu Leu Trp His Ala Cys Ala Gly Pro Val Ala Pro Leu
    50              55                  60

Pro Arg Lys Gly Ser Val Val Tyr Leu Pro Gln Gly His Ile Glu
65              70                  75                  80

His Leu Gly Asp Ala Ala Ala Gly Gly Gly Ala Pro Pro Val
                85                  90                  95

Ala Leu Pro Pro His Val Phe Cys Arg Val Val Asp Val Thr Leu His
            100                 105                 110

Ala Asp Ala Ser Thr Asp Glu Val Tyr Ala Gln Leu Ala Leu Val Ala
            115                 120                 125

Glu Asn Glu Asp Val Ala Arg Arg Leu Arg Gly Arg Ser Glu Asp Gly
        130                 135                 140

Ser Ala Glu Asp Gly Asp Glu Gly Thr Val Lys Gln Arg Phe Ser
145                 150                 155                 160

Arg Met Pro His Met Phe Cys Lys Thr Leu Thr Ala Ser Asp Thr Ser
                165                 170                 175

Thr His Gly Gly Phe Ser Val Pro Arg Arg Ala Ala Glu Asp Cys Phe
            180                 185                 190

Pro Pro Leu Asp Tyr Ser Gln Gln Arg Pro Ser Gln Glu Leu Val Ala
            195                 200                 205

Lys Asp Leu His Gly Thr Glu Trp Arg Phe Arg His Ile Tyr Arg Gly
210                 215                 220

Gln Pro Arg Arg His Leu Leu Thr Thr Gly Trp Ser Ala Phe Val Asn
225                 230                 235                 240

Lys Lys Lys Leu Val Ser Gly Asp Ala Val Leu Phe Leu Arg Gly Asp
                245                 250                 255

Asn Gly Glu Leu Arg Leu Gly Val Arg Arg Ala Ala Gln Leu Lys Asn
            260                 265                 270

Gly Ser Ala Phe Pro Ala Leu Tyr Asn Gln Cys Leu Asn Leu Gly Ser
    275                 280                 285

Leu Pro Asn Val Ala His Ala Val Ala Thr Lys Ser Val Phe His Ile
    290                 295                 300

Tyr Tyr Asn Pro Arg Leu Ser Gln Ser Glu Phe Ile Ile Pro Phe Ser
305                 310                 315                 320

Lys Phe Ile Lys Ser Phe Ser Gln Pro Phe Ser Ala Gly Ser Arg Phe
                325                 330                 335

Lys Val Lys Tyr Glu Ser Asp Ala Ser Glu Arg Arg Cys Thr Gly
            340                 345                 350

Ile Ile Ala Gly Ile Gly Asp Ala Asp Pro Met Trp Arg Gly Ser Lys
        355                 360                 365

Trp Lys Cys Leu Met Val Arg Trp Asp Asp Val Asp Phe Arg Gln
    370                 375                 380

Pro Asn Arg Ile Ser Pro Trp Glu Ile Glu Leu Thr Ser Ser Val Ser
385                 390                 395                 400

Gly Ser His Met Ser Ala Pro Asn Ala Lys Arg Leu Lys Pro Cys Leu
            405                 410                 415
```

Pro His Val Asn Pro Asp Tyr Leu Val Pro Asn Gly Ser Gly Arg Pro
            420                 425                 430

Asp Phe Ala Glu Ser Ala Gln Phe His Lys Val Leu Gln Gly Gln Glu
            435                 440                 445

Leu Leu Gly Tyr Arg Thr His Asp Asn Ala Ala Val Ala Thr Ser Gln
            450                 455                 460

Pro Cys Glu Ala Thr Asn Met Gln Tyr Ile Asp Glu Arg Ser Cys Ser
465                 470                 475                 480

Asn Asp Ala Ser Asn Ile Ile Pro Gly Val Pro Arg Ile Gly Val Arg
                485                 490                 495

Thr Pro Leu Gly Ser Pro Arg Phe Ser Tyr Arg Cys Ser Gly Phe Gly
            500                 505                 510

Glu Ser Pro Arg Phe Gln Lys Val Leu Gln Gly Gln Glu Val Phe His
            515                 520                 525

Pro Tyr Arg Gly Thr Leu Val Asp Ala Ser Leu Ser Asn Ser Gly Phe
            530                 535                 540

His Gln Gln Asp Gly Ser His Val Pro Thr Gln Ala Ser Lys Trp His
545                 550                 555                 560

Ala Gln Leu His Gly Cys Ala Phe Arg Gly Gln Gln Ala Pro Ala Val
                565                 570                 575

Pro Ser Gln Ser Ser Ser Pro Pro Ser Val Leu Met Phe Gln Arg Gly
            580                 585                 590

Asp Pro Lys Met Ser Pro Phe Glu Phe Gly His Phe His Val Asn Lys
            595                 600                 605

Lys Glu Asp Arg Arg Ala Met Phe Val His Ala Gly Gly Ile Gly Gly
610                 615                 620

Thr Glu Gln Thr Thr Met Leu Gln Ala His His Val Ser Gly Gly Thr
625                 630                 635                 640

Gly Asn Arg Asp Val Thr Val Glu Lys Ser His Pro Ala Val Ala Ala
                645                 650                 655

Ala Ser Asp Asn Arg Glu Val Ser Lys Asn Ser Cys Lys Ile Phe Gly
            660                 665                 670

Ile Ser Leu Thr Glu Lys Val Pro Ala Met Lys Glu Lys Gly Cys Gly
            675                 680                 685

Asp Ile Asn Thr Asn Tyr Pro Ser Pro Phe Leu Ser Leu Lys Gln Gln
            690                 695                 700

Val Pro Lys Ser Leu Gly Asn Ser Cys Ala Thr Val His Glu Gln Arg
705                 710                 715                 720

Pro Val Val Ala Arg Val Ile Asp Val Ser Thr Val Asp Met Met Ile
                725                 730                 735

(2) INFORMATION FOR SEQ ID NO: 30:

(i) SEQUENCE CHARACTERISTICS:
        (A) LENGTH: 587 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..587
        (D) OTHER INFORMATION:/note= "Figure 14, sequence of
        Zm41-A"

(xi) SEQUENCE DESCRIPTION: SEQ ID NO: 30:

-continued

```
Asp Gly Ser Ala Glu Asp Gly Asp Gly Glu Thr Val Lys Gln Arg
1               5                   10                  15

Phe Ser Arg Met Pro His Met Phe Cys Lys Thr Leu Thr Ala Ser Asp
            20                  25                  30

Thr Ser Thr His Gly Gly Phe Ser Val Pro Arg Arg Ala Ala Glu Asp
            35                  40                  45

Cys Phe Pro Pro Leu Asp Tyr Ser Gln Gln Arg Pro Ser Gln Glu Leu
50                  55                      60

Val Ala Lys Asp Leu His Gly Thr Glu Trp Arg Phe Arg His Ile Tyr
65                  70                  75                  80

Arg Gly Gln Pro Arg Arg His Leu Leu Thr Thr Gly Trp Ser Ala Phe
                85                  90                  95

Val Asn Lys Lys Lys Leu Val Ser Gly Asp Ala Val Leu Phe Leu Arg
            100                 105                 110

Gly Asp Asn Gly Glu Leu Arg Leu Gly Val Arg Arg Ala Ala Gln Leu
            115                 120                 125

Lys Asn Gly Ser Ala Phe Pro Ala Leu Tyr Asn Gln Cys Ser Asn Leu
130                 135                 140

Gly Ser Leu Pro Asn Val Ala His Ala Val Ala Thr Lys Ser Val Phe
145                 150                 155                 160

His Ile Tyr Tyr Asn Pro Arg Leu Ser Gln Ser Glu Phe Ile Ile Pro
                165                 170                 175

Phe Ser Lys Phe Ile Lys Ser Phe Ser Gln Pro Phe Ser Val Gly Ser
                180                 185                 190

Arg Phe Lys Val Arg Tyr Glu Ser Asp Asp Ala Ser Glu Arg Arg Cys
            195                 200                 205

Thr Gly Ile Ile Ala Gly Ile Gly Asp Ala Asp Pro Met Trp Arg Gly
210                 215                 220

Ser Lys Trp Lys Cys Leu Met Val Arg Trp Asp Asp Val Asp Phe
225                 230                 235                 240

Arg Gln Pro Asn Arg Ile Ser Pro Trp Glu Ile Glu Leu Thr Ser Ser
                245                 250                 255

Val Ser Gly Ser His Met Ser Ala Pro Asn Ala Lys Arg Leu Lys Pro
            260                 265                 270

Cys Leu Pro His Val Asn Pro Asp Tyr Leu Val Pro Asn Gly Ser Gly
            275                 280                 285

Arg Pro Asp Phe Ala Glu Ser Ala Gln Phe His Lys Val Leu Gln Gly
            290                 295                 300

Gln Glu Leu Leu Gly Tyr Arg Thr His Asp Asn Ala Ala Val Ala Thr
305                 310                 315                 320

Ser Gln Pro Cys Glu Ala Thr Asn Met Gln Tyr Ile Asp Glu Arg Ser
                325                 330                 335

Cys Ser Asn Asp Ala Ser Asn Ile Ile Pro Gly Val Pro Arg Ile Gly
            340                 345                 350

Val Arg Thr Pro Leu Gly Ser Pro Arg Phe Ser Tyr Arg Cys Ser Gly
            355                 360                 365

Phe Gly Glu Ser Pro Arg Phe Gln Lys Val Leu Gln Gly Gln Glu Ile
370                 375                 380

Phe His Pro Tyr Arg Gly Thr Leu Val Asp Ala Ser Leu Ser Asn Thr
385                 390                 395                 400

Gly Phe His Gln Gln Asp Gly Ser His Val Pro Thr Gln Ala Ser Lys
            405                 410                 415

Trp His Ala Gln Leu His Gly Cys Ala Phe Arg Gly Pro Gln Ala Pro
```

```
                    420              425              430
Ala Val Pro Ser Gln Ser Ser Pro Pro Ser Val Leu Met Phe Gln
            435              440              445

Arg Gly Asp Pro Lys Met Ser Pro Phe Glu Phe Gly His Phe His Val
    450              455              460

Asn Lys Lys Glu Asp Arg Arg Pro Met Phe Val His Ala Gly Gly Ile
465              470              475              480

Gly Gly Thr Glu Gln Thr Thr Met Leu Gln Ala His His Val Ser Gly
            485              490              495

Gly Thr Gly Asn Arg Asp Val Thr Val Glu Lys Ser His Pro Ala Val
            500              505              510

Ala Thr Ala Ser Asp Asn Arg Glu Phe Ser Lys Asn Ser Cys Lys Ile
        515              520              525

Phe Gly Ile Ser Leu Thr Glu Lys Val Pro Ala Met Lys Glu Lys Gly
        530              535              540

Cys Gly Asp Ile Asn Thr Asn Ile Asn Thr Asn Tyr Pro Lys Ser Leu
545              550              555              560

Gly Asn Ser Cys Ala Thr Val His Glu Gln Arg Pro Val Val Gly Arg
            565              570              575

Val Ile Asp Val Ser Thr Val Asp Met Met Ile
            580              585
```

(2) INFORMATION FOR SEQ ID NO: 31:

(i) SEQUENCE CHARACTERISTICS:
        (A) LENGTH: 2582 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 31:

```
GAATTCAAGG GAGAAGATGA TTTATCAGCA GGCTCTATGA GCACAGCTGC AAAGTCAAGA      60

CATAATTCTT GGGCCTCTGC AGGTGATTCT CACCCCTACT CTGACATTGC TTGCCCTTCA     120

AAAATATTCA GTCAAGACAA AAAAGAACTT ACTAATCAAA TGTCATTATC AGTCAATACT     180

TTAAGATAAG TAGAATCGAT GTCCCATACG ACATTCTAGC CACGCACTTA AACATGTGCC     240

AGATATGTTC AGATCTTGTG ATTCAACAGA CCCTCGACGC CGACTTTCATG TATATCTTTT    300

AGGTTGAAGC TTTTGCTTAG TTCAGTGTTG CTATCAGAAA GCTAAAATTA TTTTCTTGCC     360

ACCTCCTCTG CATTTTTTAC TGCTTCAGCT CCTGGTGCTT CTAATCGAGT ACTATAGAAA     420

GCATCTCCCT TGATAAATCG TTGTGTGCAA ATATAGGGTG CTTATATAAT CCATCATTAG     480

AGTATGAGGC GTGCTTTATT CTATGTGCTT CCCACAAAAA GAGTAGCCTA TTATAAACTT     540

TGTATTAGAG CACATGACGT TCTAAGTTTT GACCACATTT CTCTACTATT ATATTGCAGC     600

CATAAAGATT CAATTTTTAT GTTGGGCACC ATAAAGATGT TTGGCACCAT TCTTCCCAAA     660

CATTTATCTA CTATTATAAT GCATGCTTTA TTCAATTTTT AGTATTGTTA GGGGTGAAGT     720

CTTAGTCTCA AGATAGCATA TTGTTGTTTG CCTACTCCGA CGACTCTGAC GAGGCTGCTG     780

CCCCGCGCCA GGAGGGAGGT CAAGAAGCCT AAGAAGCCCA AGGTGAAGCA ACGATTCTCG     840

CGGATGCCGC ACATGTTCTG TAAGACGCTC ACGGCCTCCG ACACCAGCAC ACACGTCGGC     900

TTCTCCGTGT CGCGCAAGGA CAGAGCAAGC TATGTCATGT GAAGCTATGT CATGTGTGGT     960

CCTTGGTTTC TGATGAATAT GCATATGAAT GTGATGCAGG GCAGCCCCGC AGACACCTTT    1020
```

-continued

```
TAACCACTGG ATGGAGTGCC TTTGTCAACA AGAAGAAGCT TGTCTCAAGG GACGCCGTAC      1080

TATTTTTGAG GTAGGCCACA ACTAACATTG GAGATAATTA TCACATGTTG GTGTTGGCCC      1140

TTTCTGAAGG TTCCTCATAA TTTTCAGGGG TGATAATGGG GAGCTAAGAC TTGGAGTGCG      1200

CCGTGCAGCT CAGCTTAAAA ATGGATCTGC TTTTCCAGCT CTTTATAACC AGTGCTCAAA      1260

TCTTGGTTCA CTACCTAATG TTGCACATGC TGTGGCCACC AAAAGTGTGT TCCACATCTA      1320

CTACAACCCT AGGTGATGAT GAATATAGCG GTTTCACTTT AATGTTTTTG CATGTTCAAT      1380

TGTTCATGTG GTTGGCACTC TTTTAGATGA TGTGAATTGA AATGTGCTTA TTAACTACTC      1440

TTTCAATTGA CGGGGAATTT GAAATTGTGT CATTGTGTGT GATATCATTT CCTGAGTTGT      1500

TTCGAGCTAT GTAATTCATG ATTCTTACTG CAATTCAACA TTAAGTGATA TATAATTACT      1560

TTTTGAATTG ATATTGTCAC TTACATTTGG ACCCTTCAAT ATAAATCTTT CCAATTAATG      1620

CTCTTTTTAT CCACTCTTTG TTGTCAAGTT TCTGCAATTT AGAAGTATGC TTTCTTTTGT      1680

ATTTAATTCT TTTTAGGCCA CAGATTGTTA TTTCTTCATG CCATAATTTC TCTGTTTTAT      1740

TAGTCATAGT AACAGAAATA TTTTTCAATT GTTGTGGCGG CTGGCCTTGA CTGCTATGGC      1800

GGTGGCCGGA CTGGCCAGCG ATGGCGGTGG CCGGATAGCA CCGCGAGAGC AACGTCCAGA      1860

GGCTAGCAGT TCGTTGGTTG TTGAGATTTG TACCAATGAT TATCTATATT TAGAGTTGTT      1920

GTTGGATACA CCCATCCATT TAGTCCTTGT CTATCTTTTA CACAACCATC TAAACTATAA      1980

ATTTAGCTAG GATTATAAAT AAGCTGTTGG AGTTGCTCTT AGGTGGCTCC TCCAATATAG      2040

GATTAGTCCA TTTTTCTACA AACTTTGATG TGAATTGAGT TTCTGCCAAT CATGTTATAT      2100

ATGCATATGT GATGTGAATT GAGATTCATT GAGCAACACA AGGATTCTGT GTTGGAGATG      2160

GGGTCTTAAT ATTTCTATCA TGTAATATCT TTTGGTAGCT TGCATCATAT TAATAAAATA      2220

TCTTTGGTGG CCTCAGGTCT GGTGGTAATG CTTATGTGAT TGGTGATTCT GCAAAGCCTG      2280

AGCAGAAGTG GCACGCCTAC TATGCCACTA CTGAGCACCC CTGAGGAGCT TGTTGTTACT      2340

CTTAACATGT GCATGACTGG GCTGGACAAG AAGAGAGCTT CTGTCTTCTT CTAGGCTTCT      2400

GCTGATGGTT ACACATCTTG TGCTAAGGAG ATGACCAAGC TCTCAGGTAT CTCGGACATT      2460

ATCCTATAGA CAGAGATCTG CGACTAATTT GTTAGGTTGG TTCTTCATCA TTTTGTAGAT      2520

GCCCTTCCTT CTCGCTACAT GAACTAACTA ATGACAGAGG GTGGAAGTGA CCCATGAAGC      2580

TT                                                                     2582
```

(2) INFORMATION FOR SEQ ID NO: 32:

(i) SEQUENCE CHARACTERISTICS:
        (A) LENGTH: 5872 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 32:

```
GTCGACCTGC AGGTCAACGG ATCTATTGAA CCAGCAGTCT TTGCAATTGA GATTTGACTG        60

CCGGATTTGG TTTCAGCATG GATGCACCAC CCCACATCAT GTGGTTCTAG AGCATATAGT       120

GGTCTTGTAG CGCCTAAAAG TTTTAGTAGC ATCAAATGTC AGAAATATAT CTTCATCTCC       180

AGAAAATATT AGTACTTCAT AGGATGAAAA TTGTTCAACC TGAAATAATT TATTTCTTGC       240

ATCCTTCAGG TTGTATGCGA AACCACTAGA TTGAATAATT CAAGAAATCT ACAGAGGCAG       300

TCGTGAACAA CTATATATGC GCAAGATTGA GCCTAAGGTT TGTAGACCCT TTAATTCATA       360
```

```
CAAGGGCATT GCCATTTCCC CCGTAATTTC GATGCAGCTC CTTTAGCCAT ATAACAATGA    420

AAACCAACGA TCCTGCAATC CTGAAAGGGT GAATTTATGG GAGAAGCGTA CAACTCCTTT    480

AGCCAATGAT TCCAATGAAG CACCAGCCTA CAAGAATAAA ATAGATAAAT TAACAGGGTA    540

TAAAAATGAT ACTAATCACA TGTAGTAAAA GAAACTTAAT CCTTCCACTG CATCACGTAT    600

ATGTGAGTGC TCCCTGGTTT TTCATTACAG TCTTGTGATT TCCATTTTAT GCTCGATGTA    660

GGTATAGGCA TCTGATGGAG GACGTTTTGT CTCTACTCCC GCATGTGAAG AAGGACAACC    720

AGGACAAGGT CGAGTCCAAG CAGAGCAAGG GGAACACGCT GAACAAGTTG CTTGAGTTCA    780

GGAGCTGCTT CAGCTGCCTT TCTTCGAGGT ATAGATATTC TACTGTGCCT CCACACAGCT    840

GGTGGAAATT TTGTTATCAT AGATACGATG GCGGCTGCTT ACATGTGGGA ATCTTACACT    900

GTATAAGTCA GTGGCGCAAA TCAAATCTCC AACTTGGGTT TGGTCCACCT TTCGTGAAAT    960

GAATGTTTTC TGGGCTTTCA GGTATTGAGT AAGGAGCTCC CATTTTGCTC TGGTGCCAAA   1020

TTCTCTACTA GGCAATTGAC GTTTTTACTG CATTTGTGAC ATCTGCCTTC CCACAATTAT   1080

AATTGTTCAA TATATGTATG CATTAGACTT ATCAATTTTA TTAACTTATT GAATTGTATG   1140

TGCATGAAGT TTTTTCTTTC ATGTATTACA CCACATGACA TAGTTCTTTA ACTAATGGCA   1200

GTGTACCTTT TTTAACCTTT AGATGGCTAA ATTCAAGGGA GAAGATGATT TATTAGCAGG   1260

CTCTATGAGC ACAGCTGCAC AGTCAAGACA TAATTCTTGG GCCTCTGCAG GTGATTCTCA   1320

CCCCTACGCT GACATTGCTT GGCCTTCAAA ATATTCAGT CAAGACAAAA AGAACTTACT   1380

AATCAAATGT CATTATCAGT CAATACTTTA AGATAAGTAG AATCGATGTC CCATACGACA   1440

TTCTAGCCAC GCACTTAAAC ATGTGCCAGA TATGTTCAGA TCTTGTGATT CAGCAGACCT   1500

TGACGCCGAG CGGGCCTCCG CGGAGGCAGT AGCCAGATCT GGCCATTGAG TGCCCCGACG   1560

CCGCTGCTTA CTCATCCATC GCCGCGGTGA CCTGCTCCCC CTCGGGCATA TCTGTCCATT   1620

GACACCAAGC ATGTTCTTTC CTGAACTGTT CTAAAAGTTC AGTTTCATGG TTGTTTATTC   1680

TTTTGATCAG GAAGGAGAGA AAGGGAGAAT CAGTTAGAAG AAAGAAGAGT CTGAAAGCTG   1740

AGTAATTTAC CTCAACTTTA CTACCCATGT TATTAAGATC TATTGATGAT CGTCCCACTT   1800

ACTCCTATGA TGCACAGACT TAATGGATCA TGGACTGACA TATTTATCAC GGGTTTTGGG   1860

TTGTCTTCCT TCCCAGTTTT GTTTTACCAG TGGAGACACG AAGATTGGAG GACATAAGGG   1920

CGCAACACAG GACTACAGCG AGGGGAAGG CCAGATCAAG CAGGAGACAA CAAGAGGTGG   1980

GTTGCTGCTC ATTCACAATT TGATATGTTT GTTTTTTCGT TGTTATAGCT GAACTGCACA   2040

TGCAGTTTGA AACATGTTGT TACTGATGTG TTTGTCTATT ACAGGATGTG ATAGATGGTG   2100

ATCTCTGTGA GCAGTATCCC TCCCTCCTAG CTGATATGCA GAGGAAGATT GCTGATGAGC   2160

TGGACAGAAG TCCGACGCCT GCAGCACTGC TTGGTGAGGA TTGCCAAGGA GGAAGACTAG   2220

AACAAGCAAG AGCAGCGTTA ATCAGTGACA GAGCATGATG CCATCCAGAT GGGACAAGAT   2280

AAGTAAGCAG TCTTATATAG TCTGCCCACT CGAGTTTTGT ATATATTTTA GGTTGAAGCT   2340

TTTGCTTAGT TCAGTGTTGC TATCGGAAAG CTAAAATTAT TTTCTTGCCA CCTCCTCTGC   2400

ATTGTTTTGC TGCTTCAGCT CCTGGTGCTT CTAATCGAGT ACTATAGAAA GCATCTCTCT   2460

TGATAAATCG TTGTGTGCAA ATATAGGGTG CTTATATAAT CCATCATTAG AGTATGAGGC   2520

GTGTTTATT CTGTGTGCTT CCCACAAAAA AGAGTAGCCT ATTATAAACT TTGTATTAGA   2580

GCACATGACG TTCTAAGTTT TGACCACATT TCTCTACTAT TATAATGCAG CCATAAAGAT   2640

TCAATTTTTA TGTTGGGCAC CATAAAGATG TTTGGCACCA TTCTTCCCAA ACATTTATCT   2700

ACTATTATAA TGTGTGCTTT ATTCAATTTT TAGTATTGTT AGGGGTGAAG TCTTAGTCTC   2760
```

```
AAGATAGCAT ATTGTTGTTT GCCTACTCCG ACGACTCTGA CGAGGCTGCT GCCCCGCGCC    2820

AGGAGGGAGG TCAAGAAGCC TAAGAAGCCC AAGGTGAAGA AGCCCAAGGT GAAGCAACGA    2880

TTCTCGTGGA TGCCGCACAT GTTCTGCAAG ACGCTCATGG CCTCCGACAC CAGCATGCAC    2940

GTCGGCTTCT CTGTGCTGNG CCGCTCCGCC GAGGACTGCT TCCCGCCTCT AGTACGCTTG    3000

CGTTGGNTTG GAAAGCTTCC ATCTTTTCGG TGCCCGGGTG CTGCTCTCAA GGTGTGATTC    3060

TGAATCATCT GCTCTTGGGG CGTGCAGGAC TACAGCCAGC AGCGATCGTC GCAGGAGCTT    3120

GTGGCCAAGG ATTTGCACGG AACCGAGTGG AGGTTCCGCC ACATTTATCG AGGTACATGA    3180

ACAAATACTG AGATACAAGC CGAGCACATC TACCTATTTC TTTAGCAAAC TTATGTGCTT    3240

GCTCGCCCTG AATCATTCAG TGTCAGCGAA TGATGTCAAT GGCTGCACTT CAGTTGATGA    3300

CTGTTAGCGC TTTTTACAGG ATTTGCATTA CTTGTTTGGA TTGAGCACTT AGGAATGCTT    3360

CATCTTTGCT CACTTAAGTC CAGGATTTGA AGTCATTGTT CAGCCACTCT TTTGCTATAT    3420

ATGTCACCAT TATGTGATCA GAACTAATAA TGGTTATATG TCGAGAGAGA TATACAAACT    3480

ATGTCAATGT TTCCTGTTGT CTGCATTTGC AGCCTTGTGC GCTATGCTCA GCATTTCTCA    3540

TGTCATTGGT TAGTTATTGT AGTTGTACTT AAAAATTACC ATTTTGTCCA TGAAAAATCA    3600

TCTGATTATA TGTTCAGGAG TTCTGGTCCC GTTTAAAGGA ATGTAAAAGA ACAAACATGA    3660

GAAGCTATGT CATGTGTGGT CCTTGGTTTC TGATGAATAT GCATCTGAAT GTGATGCAGG    3720

GCAGCCCCAC AGACACCTTT TAACCACTGG ATGGAGTGCC TTTGTCAACA AGAAGCTTGT    3780

CTCAAGGGAC GCCGTACTAT TTTTGAGGTA GGCCACAACT AACATTGGAG ATAATTATCA    3840

CATGTTGGTG TTGGCCCTTT CTGAAGGTTC CTCGTAATTT TCAGGGGTGA TAATGGGGAG    3900

CTAAGACTTG GAGTGCGCCG TGCAGCTCAG CTTAAAAATG GATCTGCTTT TCCAGCTCTT    3960

TATAACCAGT GCTCAAATCT TGGTTCACTA CCTAATGTTG CACATGCTGT GGCCACCAAA    4020

AGTGTGTTCC ACATCTACTA CAACCCCAGG TGATGATGAA TATAGCGGTT TCACTTTAAT    4080

GCTTTTGCAT GTTCAATTGT TCATGTTGTT GGCACTCTTT TAGATGATGT GAACTGAAAT    4140

GTGCTTATTA ACTACTCTTT CAATTGACGG GGATTTGAAA TTGTGTCATT GTGTGTGATA    4200

TCATTTCCTG AGTTGTTTCG AGCTATGTAA TTCATGATTC TTACTGCAAT TCAACATTAA    4260

GTGATATATA ATTACTTTTT GAATTGATAT TGTCACTTAC ATTTGGACCC TTCAATATAA    4320

ATCTTTCCAA TTATTGCTCT TTTTATCCAC TCTTTGTTGT CAAGTTTCTG CAATTTAGAA    4380

GTATGCTTTC TTTTGTATTT AATTCTTTTT AGGCCACAAA TTGTTATTTC TTCATGCCAT    4440

AATTTCTCTG TTTTATTAGT CATAGTAACA GAAATATTTT TCAATTGTTG TGGCGGCTAG    4500

CCTTGACTGC TATGGCGGTG GCCGGACTGG CCTGAGATGG CGGTGGCCGG ATAGCACCGC    4560

GAGAGCAACG TCCAGAGGCT AGCAGTTCAT TGGTTGTTGA GATTTGTACC AATGATTATC    4620

TATATTTAGA GTTGTTGTTG GATACACCCA TCCATTTAGT CCTTGTTTAT CTTTTACACA    4680

GCCATCTAAA CTCTAAATTT AGCTAGGATT ATAAATAAGC TGTTGGATGC TCTTAGGTGG    4740

CTCCTCCAAT ATAGGATTAG TCCATTTTTC TACAGATGGG GTGATAGCAT GCACATTCTA    4800

GCATACACAT GCCCTTGGCC TGGTAATGCT TGGATTTTTT TCTCACGCAA AAGAATATAC    4860

CGGTTCGTTG AATTATGTGA TGTCATTTTC TACTTTTCTG TTTTTTAGCC GATCATCCGA    4920

AGGCTAATGA ATATTACCCT GACCCAAGAT TAGTAGCATA TGTTGTACCC TATGCACCTA    4980

TCCTATCGTG GTATCACTAA TCCTTCTAAA TTTGATATCA TCTTATCTGA TTCAGCTTGT    5040

TACTTGATTT AATTTGGCTC CTTGTTAACA GTACGGATGC TGCAAAAAAT TCCCTGAGGA    5100
```

-continued

| | | | | |
|---|---|---|---|---|
| GAAAGGTTGA | AATCTTAAAA | TTGAAGCCTC | ATTGGTCCAA | AGCTTACTTC TATTTGTGGG 5160 |
| ATGAGGTGCG | TTATTTTACC | TTTTCTGCTA | TGTCCTGATT | TCAGGGGACA CCAGTGCAGA 5220 |
| TGCATGTAGG | GAGAAACTTG | TTGCAGTTAC | AGAAATGGTT | TCCAATATCT ACTCTTGCAA 5280 |
| TTGAAGATAT | GGAGTTACTC | CTTGGGTTCT | CCTTTTAGTT | TTATTATGCT CGTCCAGTAG 5340 |
| ACATGCTCCT | GTAGTAAACT | TATATTCATG | CTTGTAATTC | CATTTACAAT GTGAATATTG 5400 |
| TGTATAGTAG | CCATGACATG | ATAATAGATT | GTTAGGGTCA | CTCATCAAAT ATTACTATGT 5460 |
| GCCGTCACAA | ATATGGGCAC | TCCACTAGGG | TTTAGGGTTT | TACCTGTTGT GCCCAGTTAG 5520 |
| GGTCACTCAT | CAAATATTAC | AGAGGGTATG | TTCCATTTAC | AGTTGGAGTA GATACGCATG 5580 |
| ACGGGGCGC | ACATGAGTTA | TTAGTCTTGT | CGGGATCTCA | TGAGTCTGAT TGACGTATTT 5640 |
| CGGATGGCTC | TCGACGTGCG | GGTCGACGAC | GGAACACTTG | CAGCGCCCAT GTTCGGATGC 5700 |
| AGCGACAGCC | TCCTTGTGTC | TTCGAACTCG | CGACGAGAGA | GAGTGGTATT CAGGACTGCT 5760 |
| TGCTTACAGG | AGAGAAATAA | GCTAATTTCT | CAGAATCTTA | GAAGCTGATT TTACAACAGG 5820 |
| ATTGCTTGCT | TACAGAGTTG | ATCAACTAAA | AAAGCGCTAT | GGTTCAGAAT TC 5872 |